US009730925B2

(12) United States Patent
Creasy et al.

(10) Patent No.: US 9,730,925 B2
(45) Date of Patent: Aug. 15, 2017

(54) METHODS OF TREATING CANCER

(71) Applicant: GLAXOSMITHKLINE LLC, Wilmington, DE (US)

(72) Inventors: Caretha L. Creasy, Collegeville, PA (US); Gopinath Ganji, Collegeville, PA (US); Michael T McCabe, Collegeville, PA (US); Kimberly N. Smitheman, Collegeville, PA (US)

(73) Assignee: GLAXOMITHKLINE LLC, Wilmington, DE (US)

( * ) Notice: Subject to any disclaimer, the term of this patent is extended or adjusted under 35 U.S.C. 154(b) by 178 days.

(21) Appl. No.: 14/346,359

(22) PCT Filed: Sep. 30, 2012

(86) PCT No.: PCT/US2012/058188
§ 371 (c)(1),
(2) Date: Mar. 21, 2014

(87) PCT Pub. No.: WO2013/049770
PCT Pub. Date: Apr. 4, 2013

(65) Prior Publication Data
US 2014/0378470 A1  Dec. 25, 2014

Related U.S. Application Data

(60) Provisional application No. 61/541,304, filed on Sep. 30, 2011.

(51) Int. Cl.
A61P 35/00    (2006.01)
A61K 31/496  (2006.01)
A61K 45/06    (2006.01)
C12Q 1/68       (2006.01)
G01N 33/574  (2006.01)

(52) U.S. Cl.
CPC ............ *A61K 31/496* (2013.01); *A61K 45/06* (2013.01); *C12Q 1/6886* (2013.01); *G01N 33/57407* (2013.01); *G01N 33/57496* (2013.01); *C12Q 2600/106* (2013.01); *C12Q 2600/154* (2013.01); *C12Q 2600/156* (2013.01); *G01N 2333/91017* (2013.01)

(58) Field of Classification Search
None
See application file for complete search history.

(56) References Cited

U.S. PATENT DOCUMENTS 9,334,527 B2 *  5/2016 Kuntz ................. C07D 473/34
2009/0012031 A1  1/2009 Chinnaiyan et al.
2009/0082359 A1  3/2009 Guzzo et al.

FOREIGN PATENT DOCUMENTS

WO    WO 2011/140324 A1    11/2011
WO    WO 2011/140325 A1    11/2011
WO    WO 2012/034132 A2     3/2012
WO    WO 2012/118812 A2     9/2012
WO    WO 2012/142504 A1    10/2012

OTHER PUBLICATIONS

Sneeringer et al. PNAS 2010 (107) 20980-20985.*
McCabe et al. (109(8) Proceedings of the National Academy of Sciences USA 2989-2994 (Feb. 21, 2012)).*
Pollock et al. (6(2) Drug Discovery Today: Therapeutic Strategies 71-79 (2009)).*
Copeland (8 Nature Reviews Drug Discovery 724-732 (Sep. 2009)).*
Gura (278 Science 1041-1042 (1997)).*
Neidle, ed. Boston: Elsevier (2006) 424-435)).*
International Search Report, which was completed on Dec. 28, 2012 in International Application No. PCT/US2012/058188.
Gugloelmelli, et al., "EZH2 mutational status predicts poor survival in myelofibrosis", Blood, 118:5227-5234, 2011.
Kubicek, et al., "Reversal of H3K9me2 by a small-molecule inhibitor for the G9a Histone Mythyltransferase", Molecular Cell, 25:473-481, 2007.
S.K. Knutson et al: "A selective inhibitor of EZH2 blocks H3K27 methylation and kills mutant lymphoma cells", Nature Chemical Biology, vol. 8, Jan. 1, 2012 (Jan. 1, 2012), pp. 890-896.
D. B. Yap et al: "Soma tic mutations at EZH2 Y641 act dominantly through a mechanism of selectively altered PRC2 catalytic activity, to increase H3K27 trimethylation", Blood, vol, 117, No. 8. Dec. 29, 2010 (Dec. 29, 2010), pp. 2451-2459.
Yap; "Soma tic mutations at EZH2 Y641 act dominantly throwzh a mechanism of selectively altered PRC2 catalytic activity, to increase H3K27 trimethylation", Blood, Feb. 24, 2011 (Feb. 24, 2011), Retrieved from the Internet: URL:http://www.bloodjournal.org/content/bloodjournal/suppl/2010/12/27/blood-2010-11321208. DC1/Document1,pdf [retrieved on Feb. 13, 2015].
C. J. Sneeringer et al: Coordinated activities of wild-type plus mutant EZH2 drive tumor-associated hypertrimethylation of lysine 27 on histone H3 (H3K27) in human B-cell lymphomas II , Proceedings of the National Academy of Sciences, vol. 107, No. 49, Dec. 7, 2010 (Dec. 7, 2010), pp. 20980-20985.
Richon Victoria Met al: Lymphoma-Associated Mutations of EZH2 Result In a Change-of-Function II , Blood, American Society of Hematology, US, vol. 116, No. 21, Nov. 1, 2010 (Nov. 1, 2010), p. 312.

(Continued)

Primary Examiner — Jeffrey S Lundgren
Assistant Examiner — Michael Schmitt
(74) Attorney, Agent, or Firm — Leah M. Octavio; Andrea V. Lockenour

(57) ABSTRACT

This invention relates to methods of treating cancer in a subject such as a human and determining at least one of the following in a sample from the subject, such as a human: (a) the presence or absence of a mutation at the alanine 677 (A677) residue in EZH2; or (b) the presence or absence of a mutation at the tyrosine 641 (Y641) residue in EZH2; or (c) the presence or absence of an increased level of H3K27me3 as compared to a control, and administering to said human an effective amount of an EZH2 inhibitor or a pharmaceutically acceptable salt thereof if at least one of the A677 mutation, Y641 mutation, or increased level of H3K27me3 is present in the sample.

10 Claims, 26 Drawing Sheets

(56) References Cited

OTHER PUBLICATIONS

M. T. McCabe et al; Mutation of A677 in histone methyl transferase EZH2 in human B-cell lymphoma promotes hypertrimethylation of histone H3 on lysine 27 (H3K2 7) II, Proceedings of the National Academy of Sciences, vol. 109, No. 8, Feb. 2012, pp. 2989-2994.
P. Guglielmelli et al: "EZH2 mutational status predicts poor survival in myelofibrosis", Blood, vol. 118, No. 19, Sep. 14, 2011, pp. 5227-5234.
McCabe MT et al: "EZH2 inhibition as a therapeutic strategy for lymphoma with EZH2-activating mutations", Nature, Nature Publishing Group, United Kingdom, vol. 492, No. 7427, Dec. 6, 2012, pp. 108-112.

* cited by examiner

Figure 2.
A.
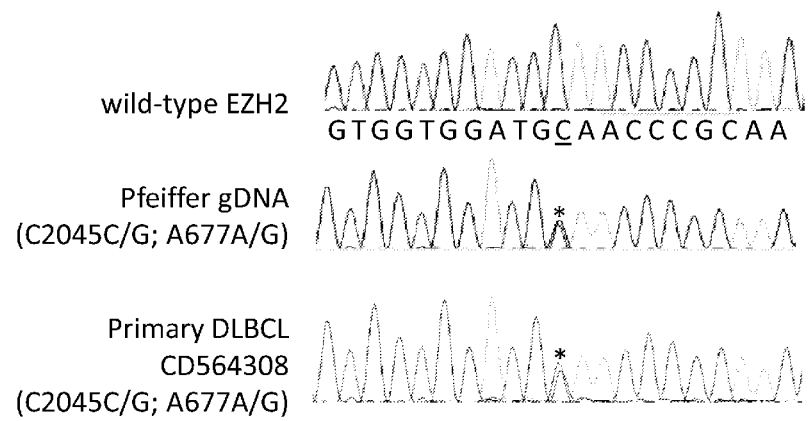
B.
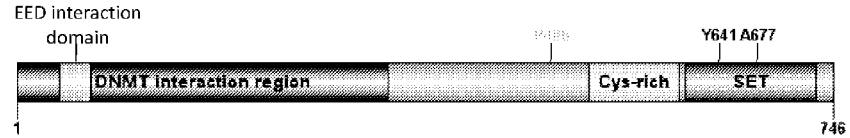
C.
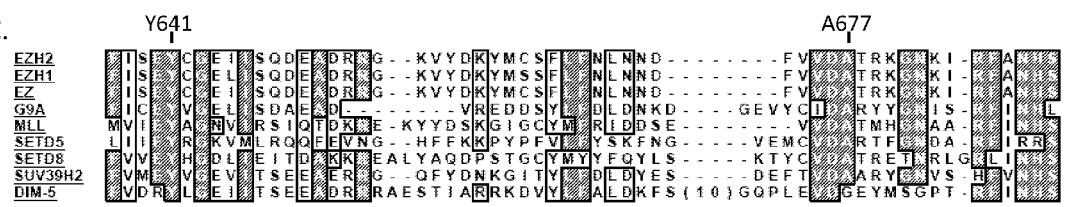

Figure 8.
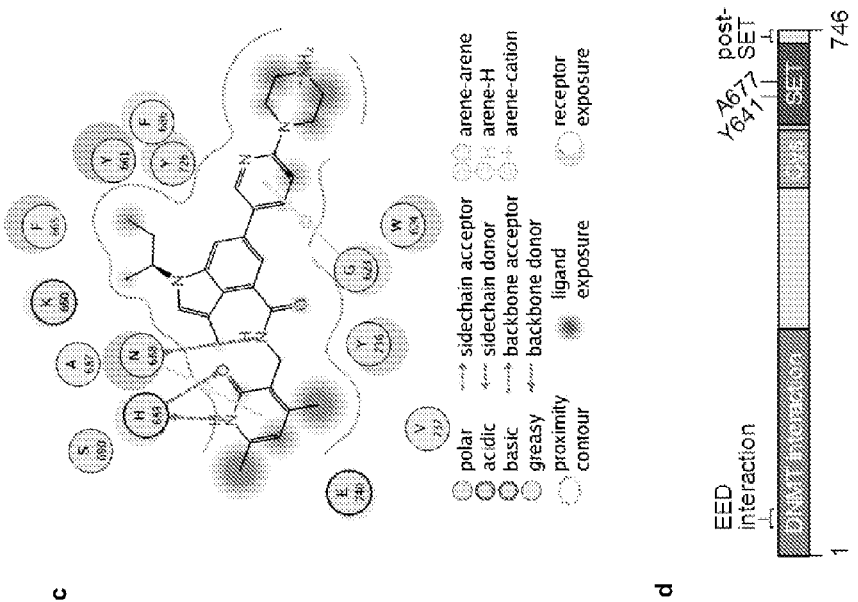
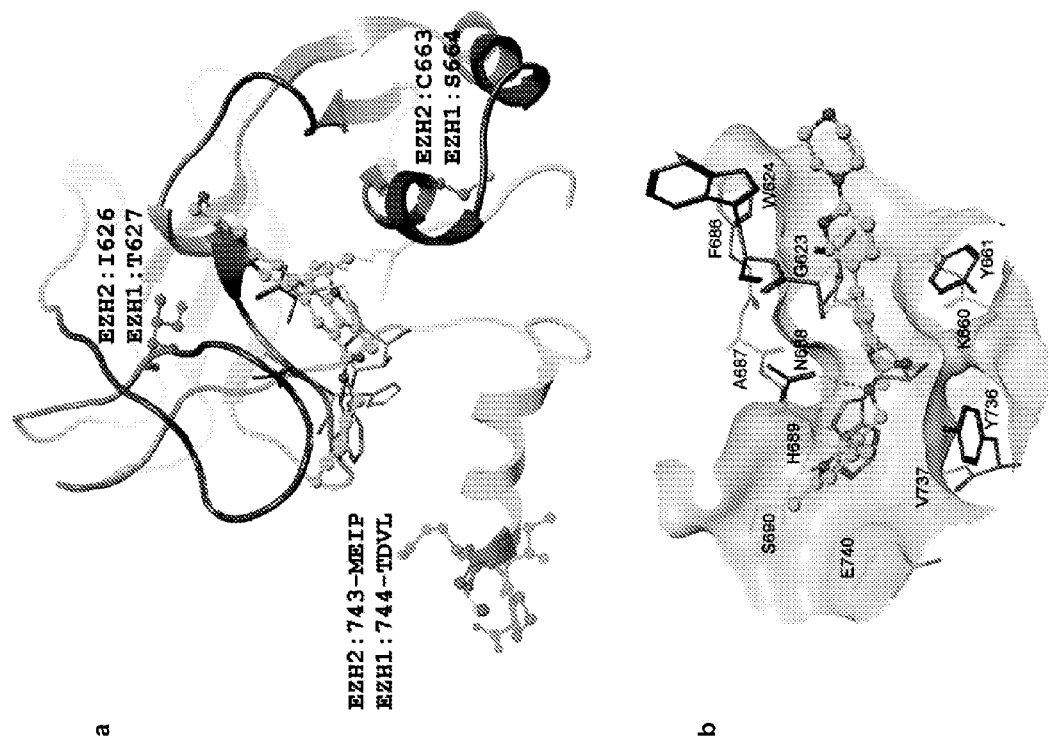

Figure 9.

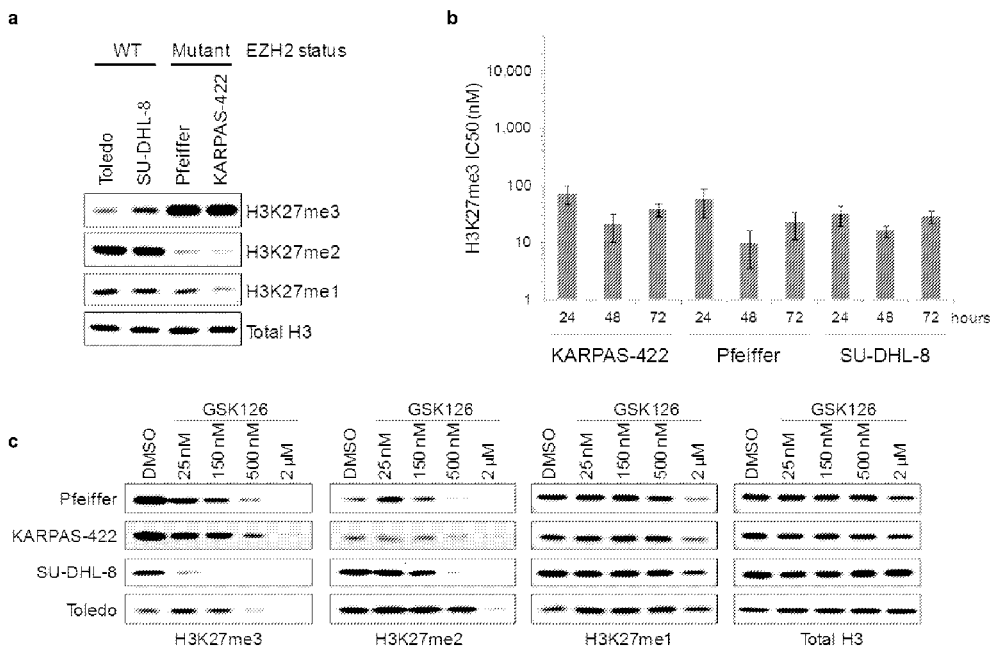

Supplementary Figure 3 | Analysis of H3K27 methylation in cell lines treated with GSK126. a Comparison of global H3K27me3, H3K27me2, and H3K27me1 levels across EZH2 WT (Toledo and SU-DHL-8) and mutant (Pfeiffer and KARPAS-422) lymphoma cell lines. b Potency of GSK126 over time as measured by reduction of global H3K27me3 levels in KARPAS-422, Pfeiffer, and SU-DHL-8 B-cell lymphoma cell lines. Cells were treated with a 3-fold dilution series of GSK126. The concentration of GSK126 required to reduce H3K27me3 levels by 50% (H3K27me3 $IC_{50}$) was determined by ELISA (n≥2; mean values ± s.d. are shown). c Evaluation of H3K27me3, H3K27me2, and H3K27me1 following treatment for 72 hours. Total histone H3 is shown as a loading control.

Supplementary Figure 4 | Western blot analysis of EZH2, SUZ12, and EED following treatment of EZH2 mutant (a,b) or WT (c,d) lymphoma cell lines with 0.1% DMSO (vehicle control), 25 nM, 150 nM, 500 nM, or 2 µM GSK126 for 72 hrs. Actin is included as a loading control.

Figure 11.
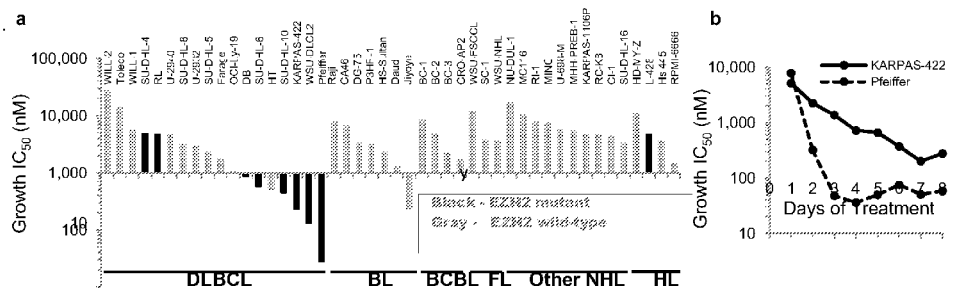 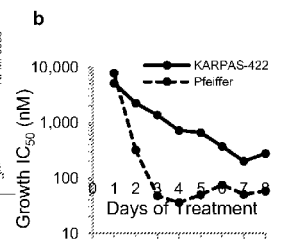
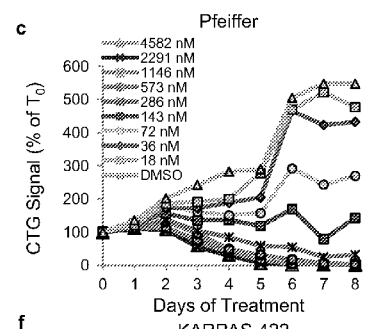 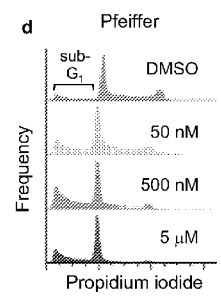 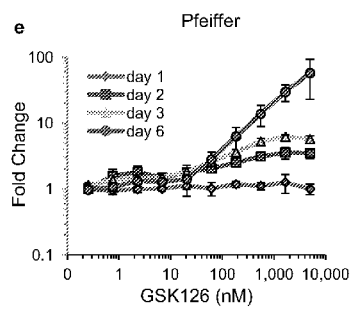
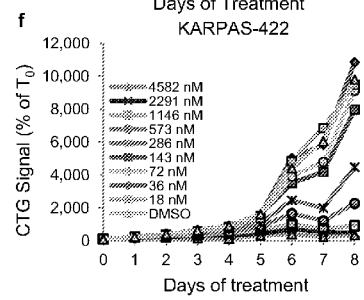 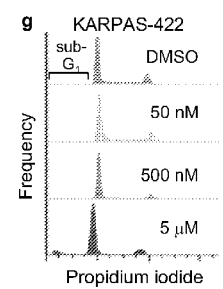 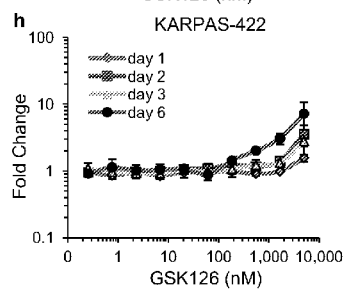

Supplementary Figure 5 | Composite dose-response curves demonstrating the effect of GSK126 on the growth of 18 DLBCL cell lines. Cell lines were treated with varying concentrations of GSK126 for 6 days before cell growth was evaluated with CellTiter-Glo (Promega). The y-axis represents the percent of growth relative to the vehicle control (0.15% DMSO).

Figure 13.

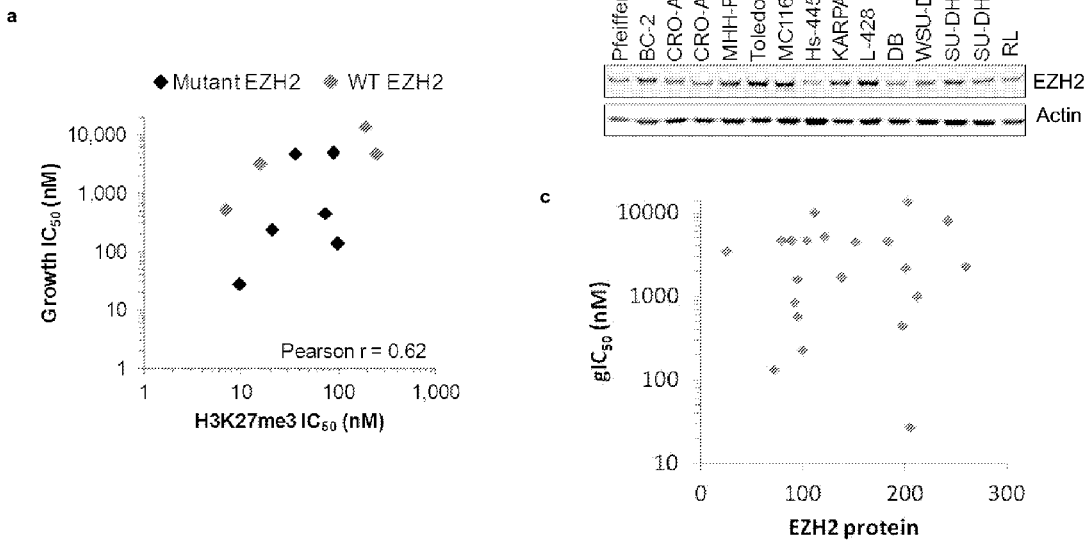

Supplementary Figure 6 | Correlation analysis between inhibition of H3K27me3, cell growth and EZH2 levels. a Cell growth $IC_{50}$ values for GSK126 from supplementary table 5 plotted against H3K27me3 $IC_{50}$ values for GSK126 from fig. 1c. Pearson correlation value is indicated. b A representative western blot of EZH2 and actin from whole cell extracts of lymphoma cell lines. Western blot signal intensities for EZH2 and actin were quantified using Li-Cor Odyssey software. c EZH2 signal intensities were normalized for total actin levels and plotted against cell growth $IC_{50}$ values for GSK126 in a 6-day proliferation assay from supplementary table 5.

Figure 14.

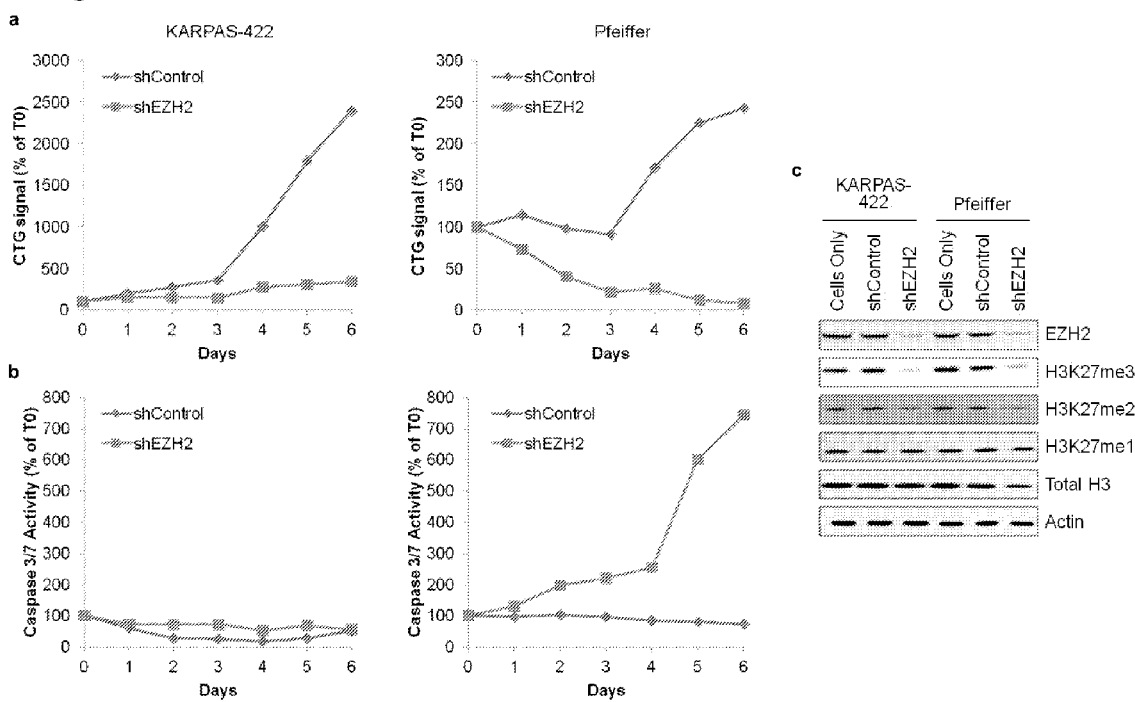

Supplementary Figure 7 | Phenotypic effects of EZH2 knockdown by shRNA. a Cell proliferation over a 6 day period of KARPAS-422 (left) and Pfeiffer (right) expressing an shRNA to EZH2 (blue) or a non-targeting control shRNA (orange). CTG signal at each time point is represented as a percentage of cells at day 0 ($T_0$). b Caspase 3/7 activity over time in KARPAS-422 (left) and Pfeiffer (right) expressing an shRNA to EZH2 (blue) or a non-targeting control shRNA (orange). Caspase 3/7 activity at each time point is represented as a percentage of activity at day 0 ($T_0$). c Western blot analysis of EZH2, H3K27me3, H3K27me2, H3K27me1, and total histone H3 following shRNA knockdown of EZH2. Actin is included as a loading control.

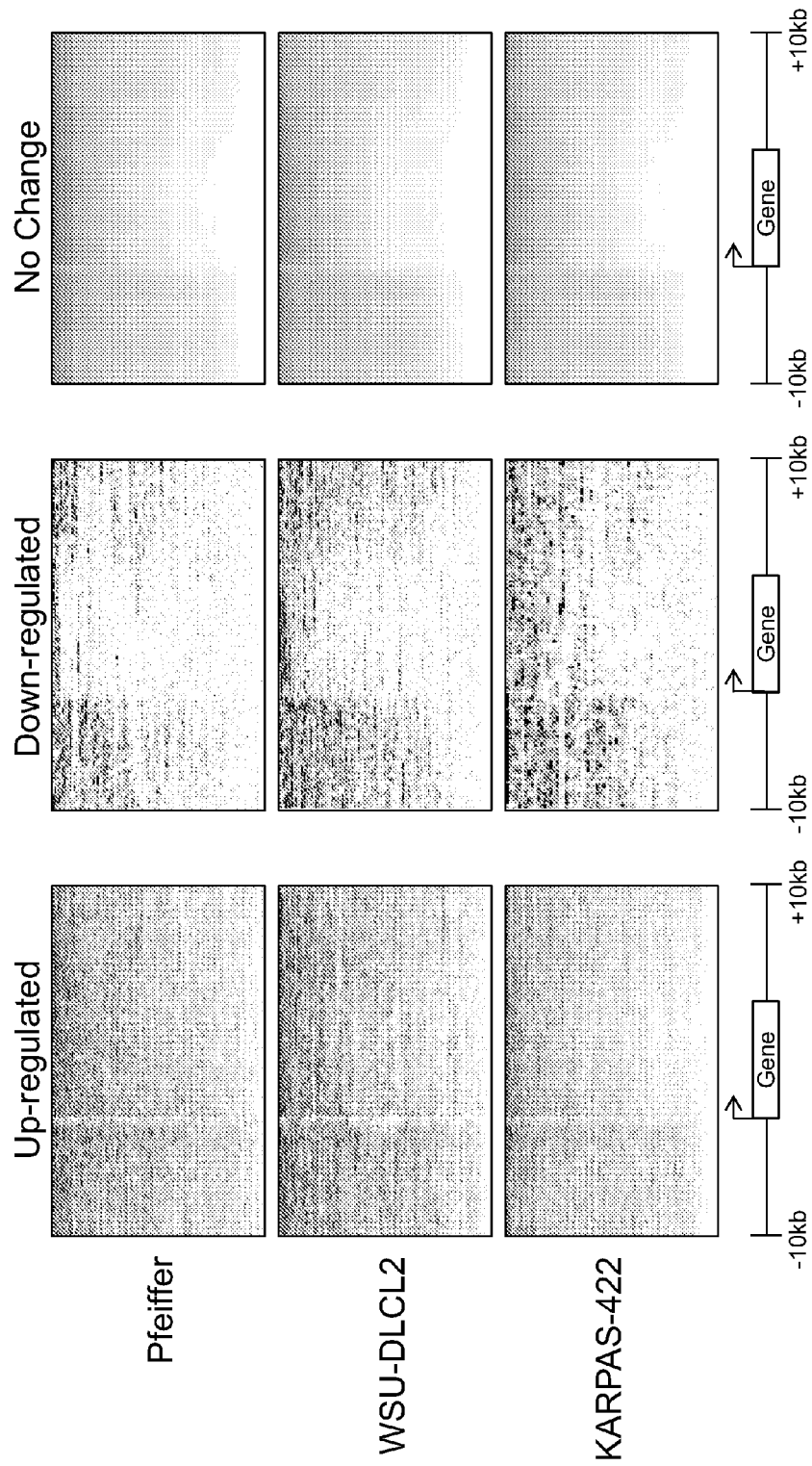

Supplementary Figure 11 | Genes up-regulated in response to GSK126 are enriched for H3K27me3. Probe sets that were significantly up-regulated, down-regulated, or unchanged identified in Pfeiffer, WSU-DLCL2, and KARPAS-422 cells following 72 hours with 500 nM GSK126 were mapped to individual genes and H3K27me3 enrichment determined for each gene and ±10kb from H3K27me3 ChIP-seq data. Relative H3K27me3 enrichment is represented as a white to red gradient with white representing no enrichment and red representing the highest enrichment. Each row represents a unique gene.

Figure 18.

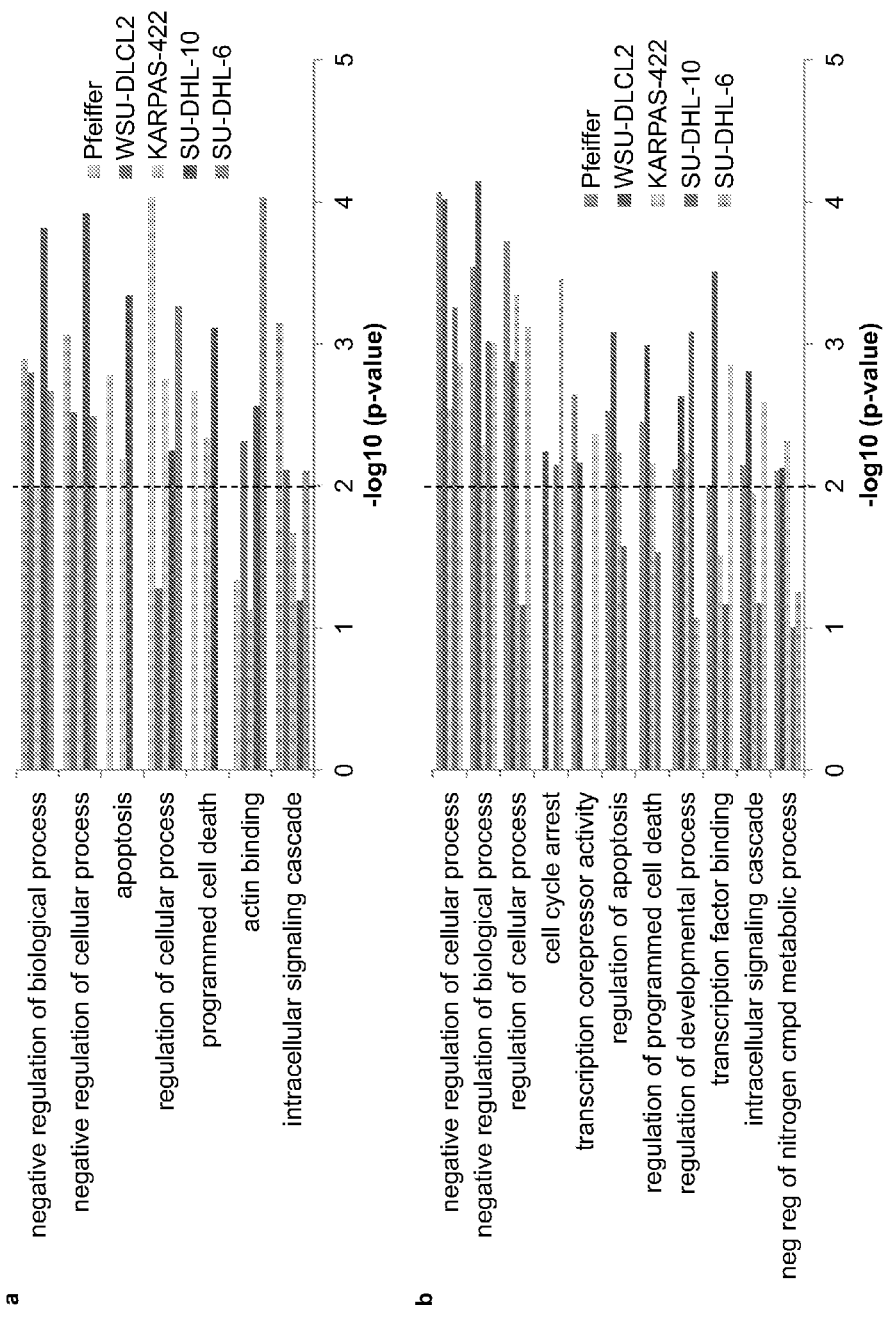

Supplementary Figure 12 | Gene ontology enrichment analysis. a GO enrichment analysis for probe sets significantly up-regulated with 500 nM GSK126 in Pfeiffer, WSU-DLCL2, KARPAS-422, SU-DHL-10, or SU-DHL-6. b GO enrichment analysis for probe sets either significantly up- or down-regulated with 500 nM GSK126 in Pfeiffer, WSU-DLCL2, KARPAS-422, SU-DHL-10, or SU-DHL-6. Over-represented biological process and molecular function terms were filtered for p-value < 0.01 (dashed lines), at least 5 genes per term, and those that were common across ≥ 3 cell lines.

Figure 20

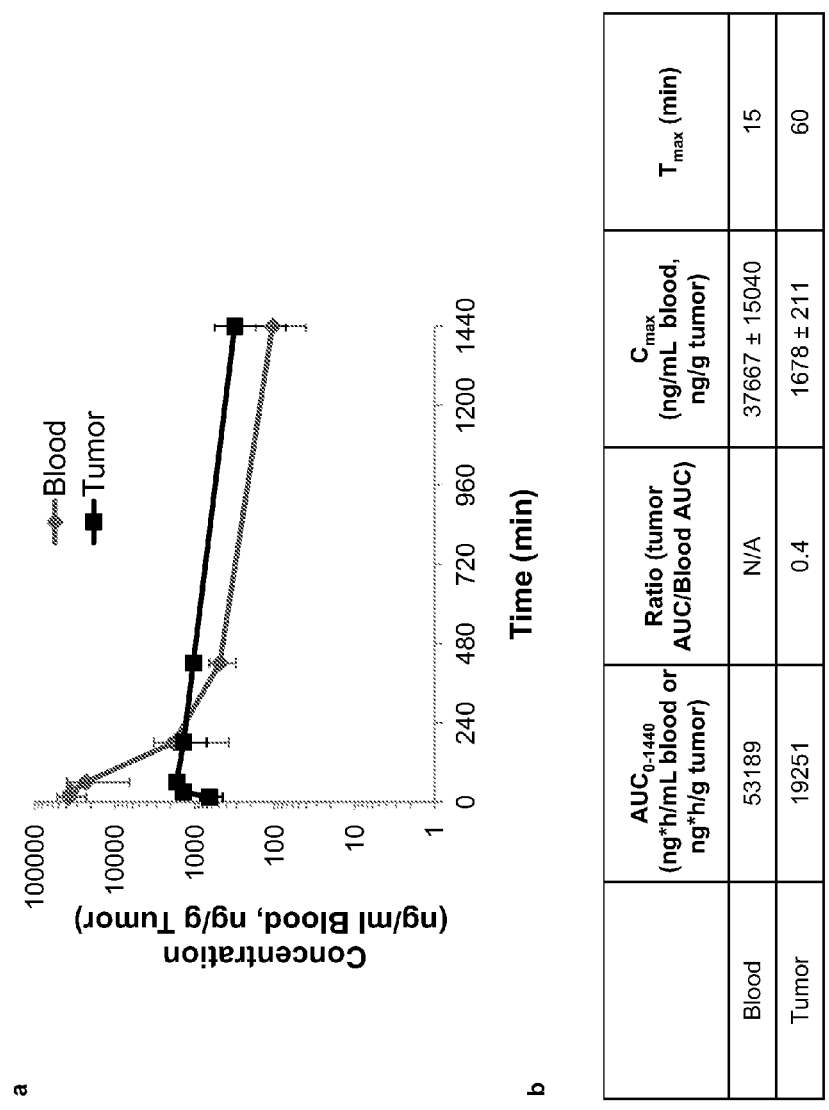

Supplementary Figure 13 | Pharmacokinetic analysis of GSK126. a Blood and tumor distribution following intraperitoneal administration of 50 mg/kg GSK126 to female beige SCID mice bearing Pfeiffer xenografts. Three mice were evaluated at each time point. b Area under the curve ($AUC_{0-1440}$), tumor/blood AUC ratio, maximum concentration achieved ($C_{max}$), and time of maximum concentration ($T_{max}$) for the data presented in a. N/A, not applicable.

Figure 21.

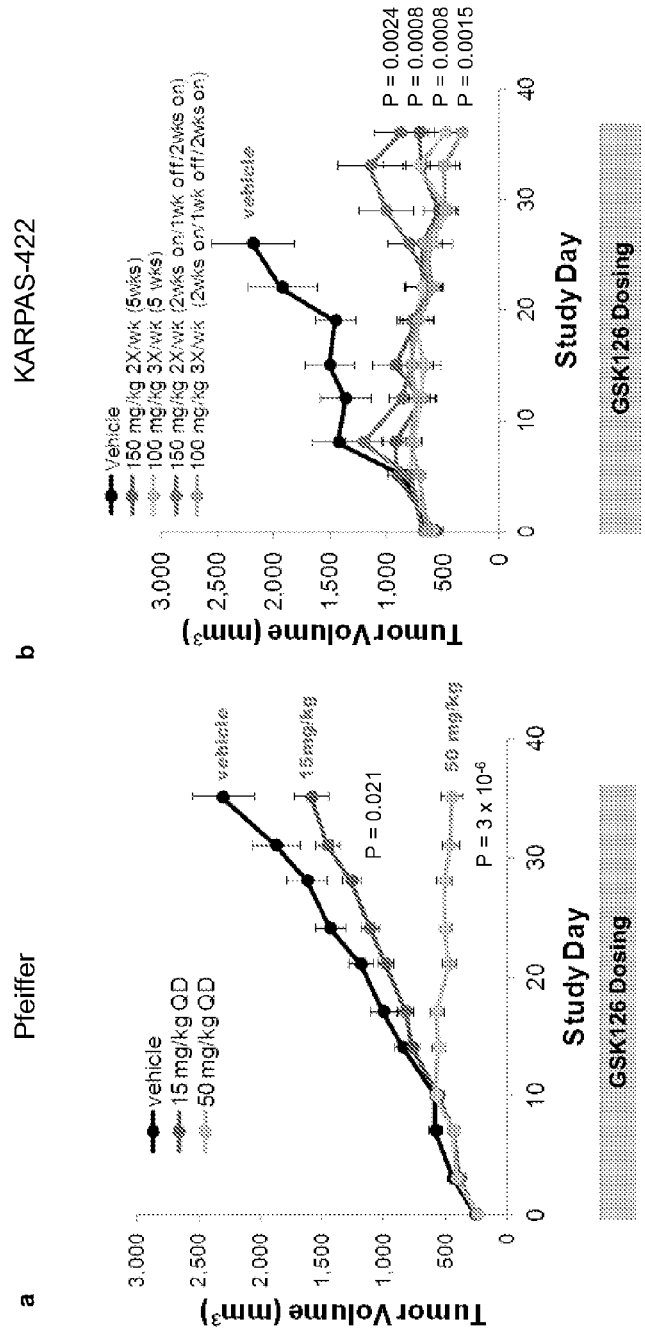

Supplementary Figure 14 | GSK126 inhibits tumor growth *in vivo*. a Efficacy of GSK126 on the growth of subcutaneous Pfeiffer xenografts. b Efficacy of intermittent dosing of GSK126 on the growth of subcutaneous KARPAS-422 xenografts with or without a 1 week drug holiday. Values are the mean tumor volume ± standard error (n=10). P values were calculated using a nonparametric log-rank test comparing vehicle and each treatment group.

Supplementary Figure 16 | Principal component and correlation analysis of gene expression profiling data. a PCA plot of data from biological replicates of 10 DLBCL cell lines treated for 72 hours with vehicle or 500 nM GSK126. b Correlation of biological replicates of DLBCL cell lines with robust transcriptional changes. K, KARPAS-422; P, Pfeiffer; W, WSU-DLCL2; S10, SU-DHL-10; S6, SU-DHL-6.

Figure 24

Table 5: H3K27me3 levels, EZH2 mutation status and growth IC50 values in a panel of lymphoma cell lines

| Cell Line | Ratio of H3K27m3:H3 as % of Pfeiffer | Compound A gIC50(nM) | Status at Y641 pr A677 |
|---|---|---|---|
| L428 | 185 | 3101 | Y641S |
| SU-DHL-10 | 134 | 324 | Y641F |
| Karpass422 | 106 | 1316 | Y641N |
| WSU-DLCL-2 | 105 | 3100 | Y641F |
| Pfeiffer | 100 | 189 | A677G |
| SU-DHL-4 | 70 | 13959 | Y641S |
| DB | 63 | 9501 | Y641N |
| Daudi | 55 | 13371 | WT |
| RL | 55 | 4660 | Y641N |
| 1A2 | 55 | 9264 | WT |
| DOHH2 | 49 | 6431 | WT |
| JM1 | 46 | 6658 | WT |
| MJ | 46 | 3278 | WT |
| RCK8 | 40 | 5563 | WT |
| CROAP5 | 39 | 6156 | WT |
| Jiyoye | 39 | 2466 | WT |
| SU-DHL-5 | 39 | 3440 | WT |
| Ramos | 37 | 3508 | WT |
| BC-3 | 36 | 5281 | WT |
| Toledo | 34 | 21817 | WT |
| RPMI-6666 | 33 | 3096 | WT |
| P3HR1 | 32 | 7797 | WT |
| Farage | 32 | 4786 | WT |
| REC1 | 32 | 2906 | WT |
| Hs445 | 32 | 1567 | WT |
| HDMyZ | 30 | 7207 | WT |
| DG75 | 30 | 6234 | WT |
| Raji | 30 | 6136 | WT |
| CROAP2 | 29 | 11337 | WT |
| NAMALWA | 28 | 6223 | WT |
| CA46 | 28 | 8631 | WT |
| U937 | 27 | 7898 | WT |
| HsSultan | 26 | 3939 | WT |
| BC-2 | 24 | 2176 | WT |
| OCI-LY-19 | 23 | 4484 | Y641N |
| HT | 21 | 3711 | WT |
| BC-1 | 20 | 8822 | WT |
| SKM1 | 6 | 6164 | Y641C |

Figure 25

TABLE 5 | GROWTH IC50 VALUE, BASELINE H3K27ME3 LEVELS, MUTATION STATUS, AND TUMOR SUBTYPE FOR LYMPHOMA CELL LINES.

| CELL LINE | AVERAGE GROWTH IC50[a] (nM) | BASELINE H3K27ME3 LEVEL[b] | EZH2 MUTATION STATUS[c] | TUMOR TYPE[d] | SUB-TYPE[e] | t(14;18) STATUS[f] | P53 STATUS[g] | CYTOSTATIC/ CYTOTOXIC[h] |
|---|---|---|---|---|---|---|---|---|
| WILL-2 | 27458 | ND | WT | B-NHL | DLBCL | N/A[j] | N/A | |
| TOLEDO | 13786 | 34 | WT | B-NHL | DLBCL | POSITIVE | MUTANT | |
| WILL-1 | 5527 | ND | D185H[k] (HET) | B-NHL | DLBCL | N/A | N/A | |
| SU-DHL-4 | 4828 | 70 | Y641S (HET); Y661N (HET) | B-NHL | DLBCL | POSITIVE | MUTANT | |
| RL | 4727 | 55 | Y641N, D185H (HET) | B-NHL | DLBCL | N/A | N/A | |
| U-2940 | 4558 | ND | WT | B-NHL | DLBCL | N/A | N/A | |
| SU-CHL-8 | 3190 | ND | WT | B-NHL | DLBCL | NEGATIVE | MUTANT | |
| U-2932 | 2935 | ND | WT | B-NHL | DLBCL | N/A | N/A | |
| SU-DHL-5 | 2299 | 39 | WT | B-NHL | DLBCL | NEGATIVE | WT | |
| FARAGE | 1715 | 32 | D185H (HET) | B-NHL | DLBCL | NEGATIVE | MUTANT | |
| OCI-LY-19 | 1019 | 23 | WT | B-NHL | DLBCL | N/A | WT | |
| DB | 861 | 63 | Y641N (HET) | B-NHL | DLBCL | POSITIVE | MUTANT | CYTOSTATIC |
| SU-DHL-6 | 582 | ND | Y641N (HET) | B-NHL | DLBCL | POSITIVE | MUTANT | CYTOSTATIC |
| HT | 516 | 21 | WT | B-NHL | DLBCL | NEGATIVE | MUTANT | CYTOSTATIC |
| SU-DHL-10 | 448 | 134 | Y641F (HET) | B-NHL | DLBCL | NEGATIVE | MUTANT | CYTOSTATIC |
| KARPAS-422 | 232 | 106 | Y641F (HET) | B-NHL | DLBCL | POSITIVE | MUTANT | CYTOSTATIC |
| WSU-DLCL2 | 134 | 105 | Y641F (HET) | B-NHL | DLBCL | N/A | MUTANT | CYTOSTATIC |
| PFEIFFER | 28 | 108 | A677G (HET) | B-NHL | DLBCL | POSITIVE | WT | |
| RAJI | 7868 | 30 | WT | B-NHL | BURKITT | N/A | N/A | |
| CA46 | 6585 | 26 | D185H (HET) | B-NHL | BURKITT | N/A | N/A | |
| DG-75 | 3254 | 30 | WT | B-NHL | BURKITT | N/A | N/A | |
| P3H4-1 | 3207 | 32 | WT | B-NHL | BURKITT | N/A | N/A | |
| HS-SULTAN | 2275 | 26 | WT | B-NHL | BURKITT | N/A | N/A | |
| DAUDI | 1265 | 55 | WT | B-NHL | BURKITT | N/A | N/A | |
| JIYOYE | 232 | 39 | WT | B-NHL | BURKITT | N/A | N/A | CYTOSTATIC |
| BC-1 | 8292 | 20 | WT | B-NHL | AIDS-BCBL | N/A | N/A | |
| BC-2 | 4752 | 24 | WT | B-NHL | AIDS-BCBL | N/A | N/A | |
| BC-3 | 2217 | 36 | D185H (HET) | B-NHL | PEL, AIDS-BCBL | N/A | N/A | |
| CRO-AP2 | 1643 | ND | WT | B-NHL | PEL, AIDS-BCBL | N/A | N/A | |
| WSU-FSCCL | 11966 | ND | D185H (HET) | B-NHL | FL | N/A | N/A | |
| SC-1 | 3727 | ND | D185H (HET) | B-NHL | FL | N/A | WT | |
| WSU-NHL | 3537 | ND | D185H (HET) | B-NHL | FL | POSITIVE | MUTANT | |
| NU-DUL-1 | 17060 | ND | WT | B-NHL | N/A | N/A | MUTANT | |
| MC116 | 10168 | 39 | WT | B-NHL | N/A | N/A | MUTANT | |
| RI-1 | 7556 | ND | WT | B-NHL | MCL | N/A | MUTANT | |
| MINO | 7340 | ND | D185H (HET) | B-NHL | N/A | N/A | N/A | |
| U-698-M | 5699 | ND | WT | B-NHL | N/A | N/A | MUTANT | |
| M-H-PREB-1 | 5300 | 33 | WT | B-NHL | N/A | N/A | MUTANT | |
| KARPAS-1106P | 4536 | ND | E744A (HET) | B-NHL | MLBCL | N/A | WT | |
| RC-K8 | 4528 | 40 | D185H (HET) | B-NHL | N/A | N/A | WT | |
| CI-1 | 4282 | ND | D185H (HET) | B-NHL | N/A | N/A | N/A | |
| SU-DHL-16 | 3282 | ND | D185H (HET) | B-NHL | N/A | N/A | MUTANT | |
| HD-MY-Z | 10717 | 30 | WT | HODGKIN'S | N/A | N/A | N/A | |
| L-428 | 4704 | 185 | Y641S (HET) | HODGKIN'S | N/A | N/A | N/A | |
| HS 445 | 3528 | 32 | WT | HODGKIN'S | N/A | N/A | N/A | |
| RPMI-6656 | 1429 | 33 | WT | HODGKIN'S | N/A | N/A | N/A | | a GROWTH IC50 VALUES REPRESENT THE AVERAGE OF AT LEAST 2 INDEPENDENT REPLICATE EXPERIMENTS
b BASELINE H3K27ME3 LEVELS ARE REPRESENTED RELATIVE TO THE LEVEL OBSERVED IN THE PFEIFFER CELL LINE.
c AMINO ACID RESIDUE NUMBER BASED ON NP_001190176.
d B-NHL, B CELL NON-HODGKIN LYMPHOMA. HODGKIN'S, HODGKIN'S LYMPHOMA.
e DLBCL, DIFFUSE LARGE B-CELL LYMPHOMA. BURKITT, BURKITT LYMPHOMA. PEL, PRIMARY EFFUSION LYMPHOMA. AIDS-BCBL, ACQUIRED IMMUNODEFICIENCY SYNDROME BODY CAVITY-BASED LYMPHOMA. MLBCL, MEDIASTINAL LARGE B CELL LYMPHOMA. MCL, MANTLE CELL LYMPHOMA. FL, FOLLICULAR LYMPHOMA. N/A, NOT AVAILABLE.
f DENG ET AL., CANCER CELL 12: 171-185 (2007).
g DORNAN ET AL., BLOOD 114: 2721-29 (2009).
h DOSE-RESPONSE CURVES FROM CELL LINES WITH GROWTH IC50 VALUES < 1 μM WERE EVALUATED FOR EVIDENCE OF CYTOSTASIS OR CYTOTOXICITY (VALUES BELOW 1)
i NOT DETERMINED.
j NOT AVAILABLE.
k D185H IS A KNOWN SNP (RS2302427).

METHODS OF TREATING CANCER

FIELD

This invention relates to methods of treating cancer in a subject in need thereof.

BACKGROUND

The expanding development and use of targeted therapies for cancer treatment reflects an increasing understanding of key oncogenic pathways, and how the targeted perturbation of these pathways corresponds to clinical response. Difficulties in predicting efficacy to targeted therapies is likely a consequence of the limited global knowledge of causal mechanisms for pathway deregulation (e.g. activating mutations, amplifications). Pre-clinical translational research studies for oncology therapies focuses on determining what tumor type and genotypes are most likely to benefit from treatment. Treating selected patient populations may help maximize the potential of a therapy. Pre-clinical cellular response profiling of tumor models has become a cornerstone in development of novel cancer therapeutics. Efforts to predict clinical efficacy using cohorts of in vitro tumor models have been successful (e.g. EGFR inhibitors are selectively useful in those tumors harboring EGFR mutations). Thus, expansive panels of diverse tumor derived cell lines could recapitulate an 'all comers' efficacy trial; thereby identifying which histologies and specific tumor genotypes are most likely to benefit from treatment. Numerous specific molecular markers are now used to identify patients most likely to benefit in a clinical setting.

EZH2 (enhancer of zeste homolog 2; human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

EZH2 inhibitors that are useful in treating cancer have been reported in PCT applications PCT/US2011/035336, PCT/US2011/035340, and PCT/US2011/035344, which are incorporated by reference herein. It is desirable to identify genotypes that are more likely to respond to these compounds.

SUMMARY OF THE INVENTION

The present invention provides methods of treating cancer in a human in need thereof, comprising determining at least one of the following in a sample from said human:
 a. the presence or absence of a mutation at the alanine 677 (A677) residue in EZH2 in a sample from said human; or
 b. the presence or absence of a mutation at the tyrosine 641 (Y641) residue in EZH2; or
 c. the presence or absence of an increased level of H3K27me3 as compared to a control, and
administering to said human an effective amount of an EZH2 inhibitor or a pharmaceutically acceptable salt thereof if at least one of said A677 mutation, Y641 mutation, or increased level of H3K27me3 is present in said sample.

BRIEF DESCRIPTION OF THE DRAWINGS

FIG. 2. The Pfeiffer lymphoma cell line harbors a heterozygous A677G mutation in EZH2. (A) Sequence traces from Sanger sequencing of EZH2 in the Pfeiffer DLBCL cell line and a primary DLBCL patient sample. Heterozygous non-synonymous missense mutation of C2045C/G (asterisks) translates to A677A/G (residue numbering based on NM_001203247). (B) EZH2 domain architecture (Uniprot Q15910). Mutations identified in Pfeiffer cells and primary tumors are highlighted. (C) Alignment of human EZH2 with human EZH1, the fly ortholog EZ, and six other related SET domain containing histone lysine methyltransferases showing that Y641 and A677 are highly conserved. Dark Grey shading with white letters represents identical residues and boxed amino acids represent conserved residues. In order for a column to be shaded there has to be 7 out of 9 conserved/identical residues in the alignment.

FIG. 8. Homology model of EZH2 and predicted binding mode of Compound B (GSK126). (A) A homology model of EZH2 and predicted binding mode of Compound B (GSK126). GSK126 bound in the SAM binding site is overlaid with SAH. The H3K27me2 peptide substrate, the SET domain, and the post-SET domain, and the residue differences between EZH2 and EZH1 within 10 Å of the predicted binding mode of GSK126 are indicated. (B) A zoomed in view of the binding mode of GSK126 is depicted. Specific hydrogen bond and arene-H interactions are represented as dashed lines. The binding site surface contributed by residues from the post-SET domain is shown. (C) A 2D ligand interaction diagram highlighting specific interactions between residues of EZH2 and GSK126. (D) Diagram of EZH2 functional domains (UniProt Q15910) with the position of the A677 and Y641 activating mutations highlighted within the SET domain.

FIG. 9 Analysis of H3K27 methylation in cell lines treated with GSK126. (A) Comparison of global H3K27me3, H3K27me2, and H3K27me1 levels across EZH2 WT (Toledo and SU-DHL-8) and mutant (Pfeiffer and KARPAS-422) lymphoma cell lines. (B) Potency of GSK126 over time as measured by reduction of global H3K27me3 levels in KARPAS-422, Pfeiffer, and SU-DHL-8 B-cell lymphoma cell lines. Cells were treated with a 3-fold dilution series of GSK126. The concentration of GSK126 required to reduce H3K27me3 levels by 50% (H3K27me3 IC50) was determined by ELISA (n≥2; mean values±s.d. are shown). (C) Evaluation of H3K27me3, H3K27me2, and H3K27me1 following treatment for 72 hours. Total histone H3 is shown as a loading control.

Figure 10:
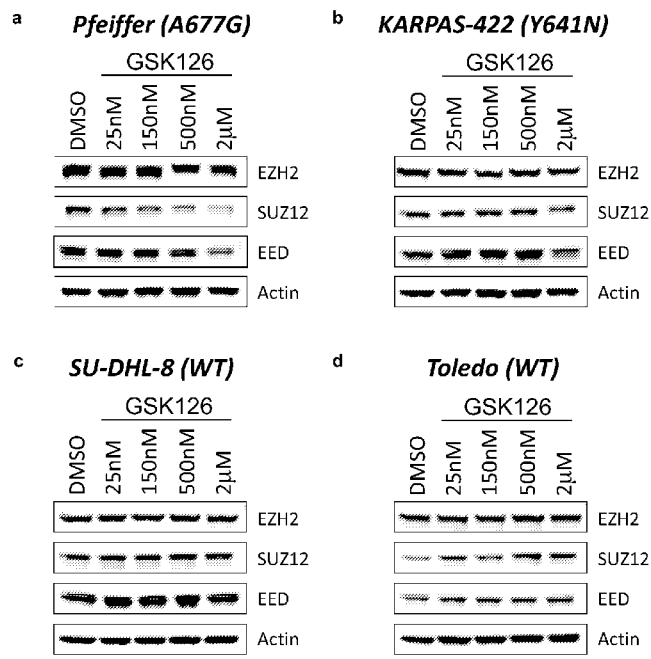

FIG. 10 Western blot analysis Western blotting of EZH2, SUZ12, and EED following treatment of EZH2 mutant (a,b) or WT (c,d) lymphoma cell lines with 0.1% DMSO (vehicle control), 25 nM, 150 nM, 500 nM, or 2 µM GSK126 for 72 hrs. Actin is included as a loading control.

FIG. 11 GSK126 inhibits the proliferation of several EZH2 mutant lymphoma cell lines. (A) The effect of GSK126 on the growth of 46 lymphoma cell lines after 6 days represented as the concentration of GSK126 required to inhibit 50% of growth (growth $IC_{50}$). DLBCL, diffuse large B-cell lymphoma. BL, Burkitt lymphoma. BCBL, AIDS body cavity-based lymphoma. FL, follicular lymphoma. HL, Hodgkin's lymphoma. NHL, Non-Hodgkin's lymphoma. (B) Potency of GSK126 on growth of Pfeiffer and KARPAS-422 over time represented as growth $IC_{50}$. (C,F) Dose-dependent effects of GSK126 on cell proliferation over time in Pfeiffer or KARPAS-422. Growth is expressed as a percentage of CTG at time zero ($T_0$). (D,G) DNA content histograms showing the effect of GSK126 on the cell cycle after 72 hours. (E,H) Mean fold-change in caspase 3/7 activity over vehicle control±s.d. is shown (n=4).

Figure 12:
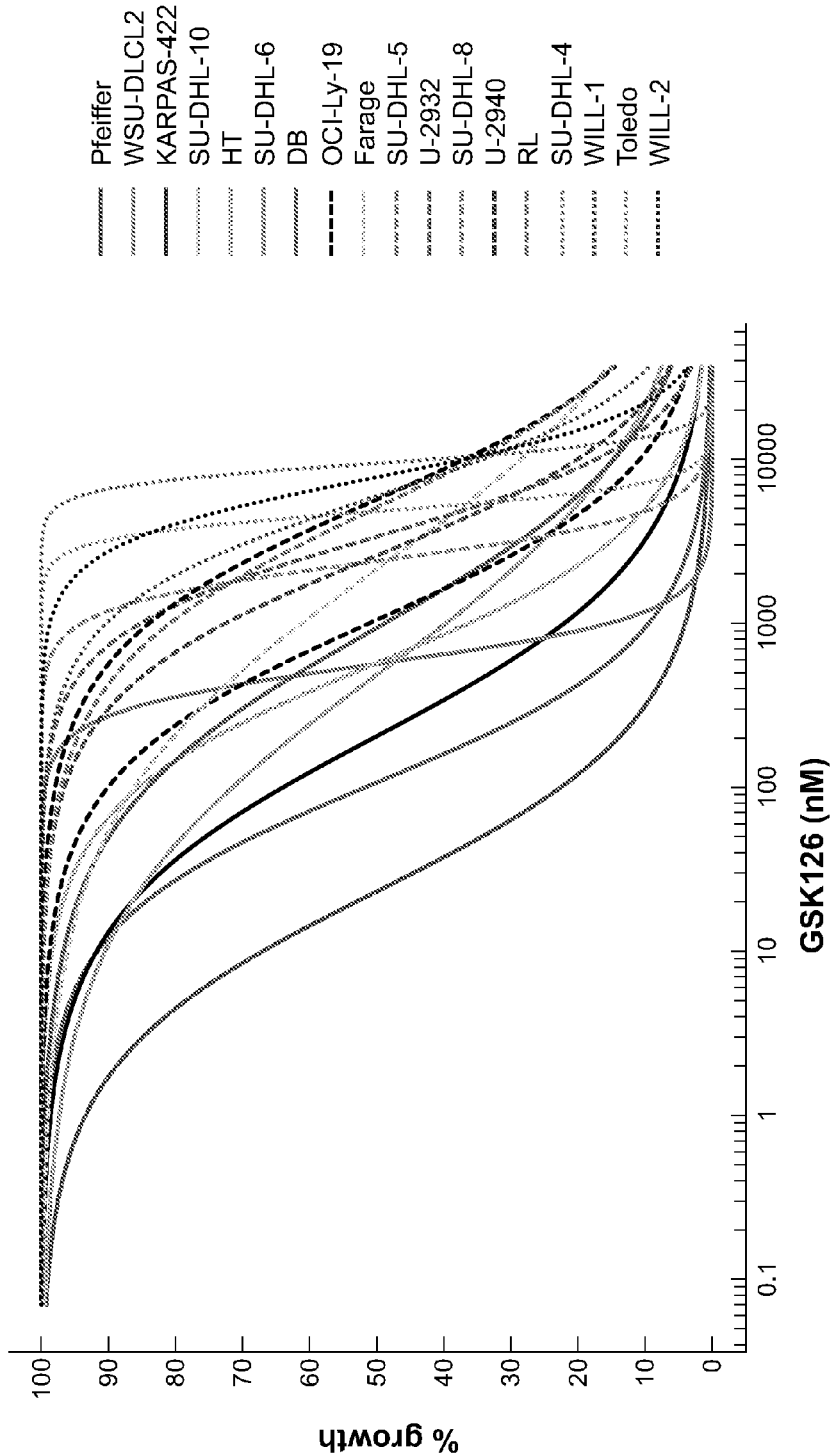

FIG. 12. Composite dose-response curves demonstrating the effect of GSK126 on the growth of 18 DLBCL cell lines. Cell lines were treated with varying concentrations of GSK126 for 6 days before cell growth was evaluated with Cell Titer-Glo (Promega) The y-axis represents the percent of growth relative to the vehicle control (0.15% DMSO).

FIG. 13 Correlation analysis between inhibition of H3K27me3, cell growth and EZH2 levels (A) Cell growth IC50 values for GSK126 from Table 6 in FIG. 25 plotted against H3K27me3 IC50 values for GSK126 from FIG. 7c. Pearson correlation value is indicated. (B) A representative western blot of EZH2 and actin from whole cell extracts of lymphoma cell lines. Western blot signal intensities for EZH2 and actin were quantified using Li-Cor Odyssey software. (C) EZH2 signal intensities were normalized for total actin levels and plotted against cell growth IC50 values for GSK126 in a 6 day proliferation assay from Table 6 in FIG. 25.

FIG. 14 Phenotypic effects of EZH2 knockdown by shRNA. (A) Cell proliferation over a 6 day period of KARPAS-422 (left) and Pfeiffer (right) expressing an shRNA toEZH2 or an on-targeting control shRNA. CTG signal at each timepoint is represented as a percentage of cells at day0 (T0). (B) Caspase3/7 activity over time in KARPAS-422 (left) and Pfeiffer (right) expressing an shRNA to EZH2 or a non-targeting control shRNA. Caspase3/7 activity at each time point is represented as a percentage of activity at day 0 (T0). (C) Western blot analysis of EZH2, H3K27me3, H3K27me2, H3K27me1, and total histone H3 following shRNA knockdown of EZH2. Actin is included as a loading control.

Figure 15:
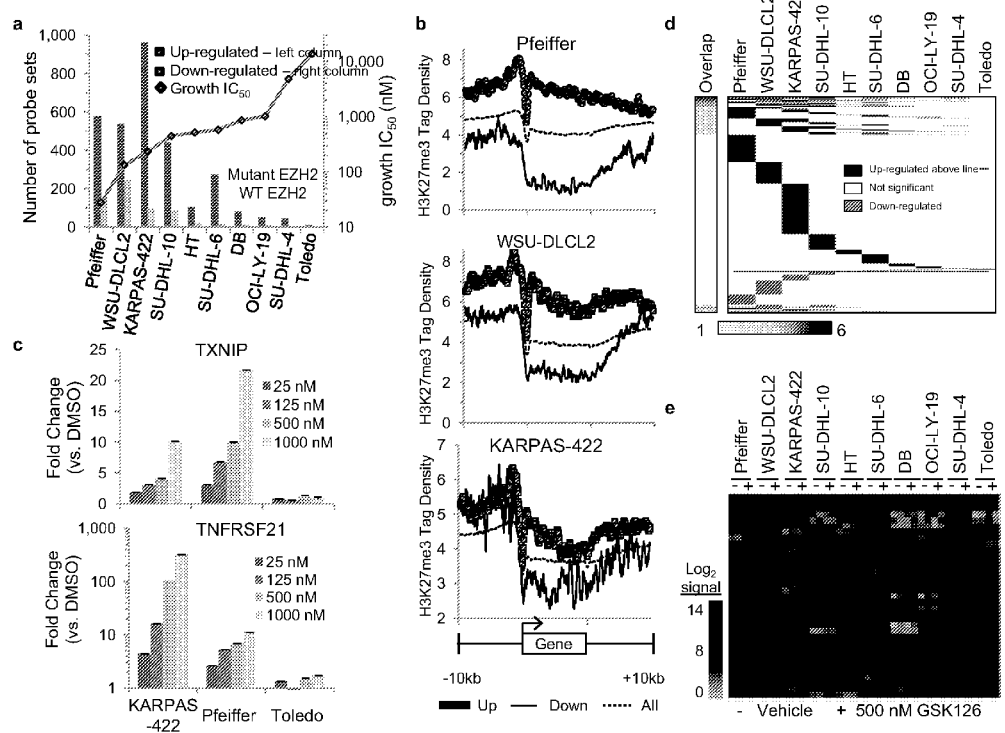

FIG. 15 GSK126 induces transcriptional activation in sensitive cell lines. (A) The number of probe sets exhibiting significantly altered gene expression (FDR<0.1 and fold-change>2 or <−2) following 72 hour treatment with 500 nM GSK126 (n=2). (B) Basal H3K27me3 ChIP-seq enrichment profiles of genes up-regulated, down-regulated, or all human transcripts following GSK126 treatment. (C) qRT-PCR analysis of TXNIP and TNFRSF21 following 72 hour treatment with GSK126 (n=3; mean values±s.d. are shown). (D) The overlap of up- and down-regulated probe sets between 10 DLBCL cell lines using a 2-fold expression change cut-off. (E) Heatmap showing the average gene expression intensities of the 35 probe sets exhibiting significantly increased expression in at least 4 of the 5 most sensitive mutant DLBCL cell lines (Pfeiffer, KARPAS-422, WSU-DLCL2, SU-DHL-10, and SU-DHL-6).

Figure 16:
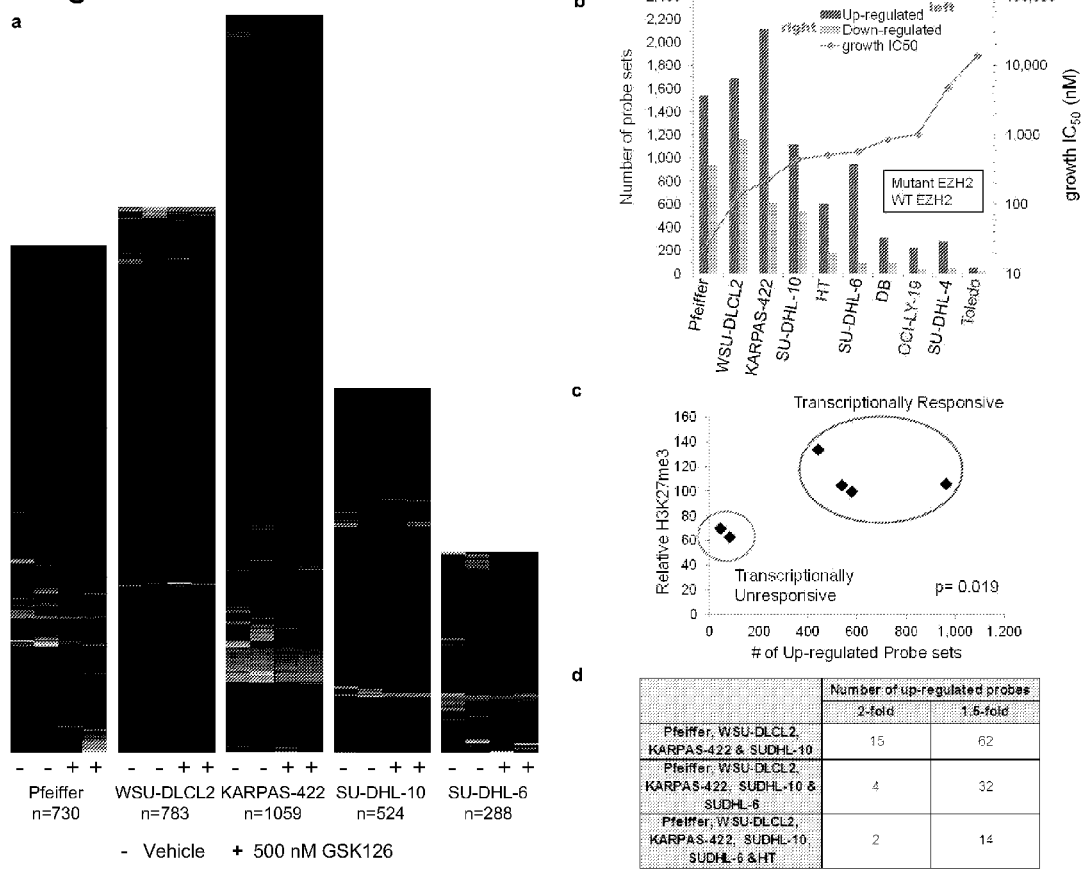

FIG. 16 Expression analysis of DLBCL cell lines. (A) Gene expression heatmaps of normalized gene expression data for differentially expressed probe sets following treatment with GSK126 for 72 hours. Darker coloring indicates higher expression. (B) The number of probe sets exhibiting significantly altered gene expression (>1.5 fold) following treatment of 10 DLBCL cell lines in duplicate for 72 hours with 500 nM GSK126 compared with 0.1% DMSO (vehicle control). (C) Correlation between the number of up-regulated probe sets and basal H3K27me3 levels intranscriptionally responsive and unresponsive mutantE ZH2 DLBCLcell lines (Pfeiffer, WSU-DLCL2, KARPAS-422, SU-DHL-10, DB, and SU-DHL-4). H3K27me3 levels are normalized to total histone H3 and are expressed as a percentage of those levels observed in the Pfeiffer cell line. Transcriptionally responsive and unresponsive cell lines are circled. (D) The number of common probe sets within indicated cell lines exhibiting a 1.5 or 2-fold increase in expression with GSK126 treatment.

FIG. 17 Genes up-regulated in response to GSK126 are enriched for H3K27me3. Probe sets that were significantly up-regulated, down-regulated, or unchanged identified in Pfeiffer, WSU-DLCL2, and KARPAS 422 cells following 72 hours with 500 nM GSK126 were mapped to individual genes and H3K27me3 enrichment determined for each gene and ±10 kb from H3K27me3 ChIP-seqdata. Relative H3K27me3 enrichment is represented as a white to gray gradient with white representing no enrichment and gray representing the highest enrichment. Each row represents a unique gene.

FIG. 18 Geneontology enrichment analysis. A GO enrichment analysis for probe sets significantly up-regulated with 500 nM GSK126 in Pfeiffer, WSU-DLCL2, KARPAS-422, SU-DHL-10, or SU-DHL-6. B GO enrichment analysis for probe sets either significantly up- or downregulated with 500 nM GSK126 in Pfeiffer, WSU-DLCL2, KARPAS-422, SU-DHL-10, or SU-DHL-6 cell lines. Over-represented biological process and molecular function terms were filtered for p-value<0.01 (dashedlines), at least 5 genes per term, and those that were common across ≥3 cell lines.

Figure 19:
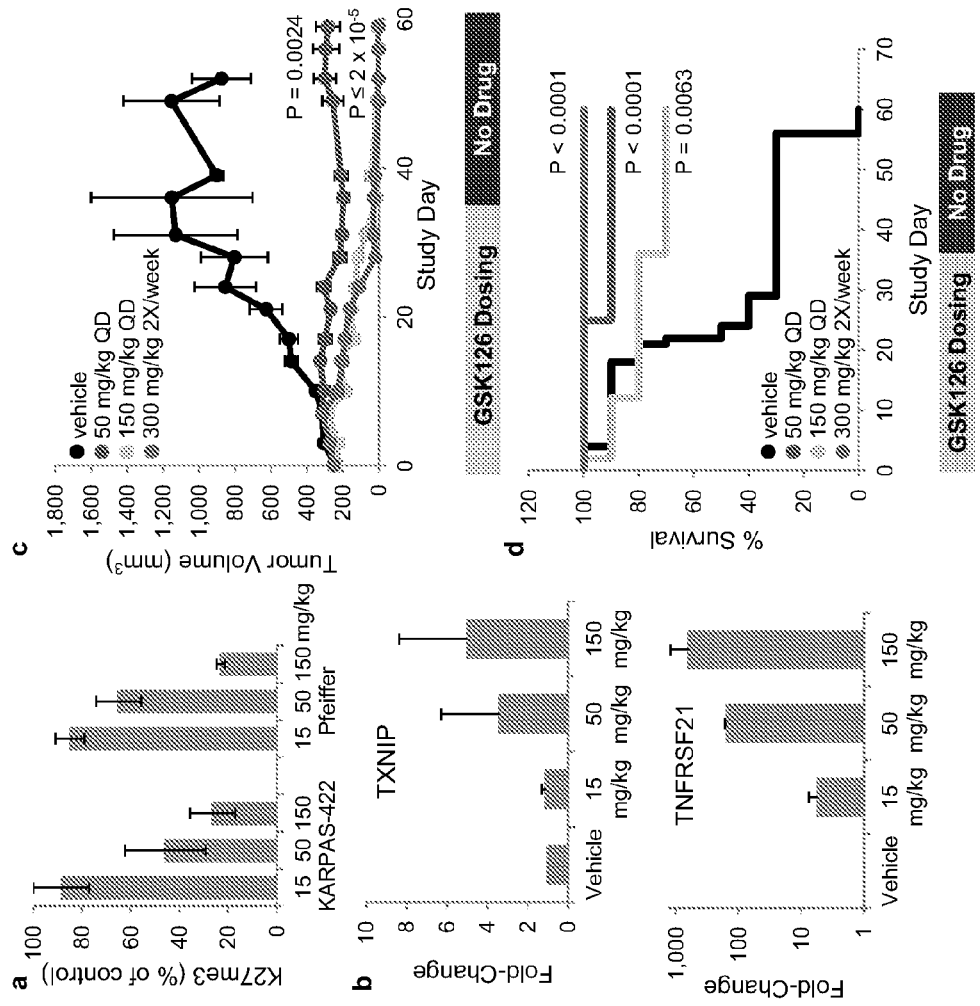

FIG. 19 In vivo inhibition of H3K27me3 and tumor growth response with GSK126. (A) Response of H3K27me3 in tumor xenografts following 10 days of QD dosing with GSK126. b qRT-PCR analysis of EZH2 target genes in KARPAS-422 tumor xenografts. Mean values±s.d. (n=3) are shown (A,B). (C) Activity of GSK126 on the growth of subcutaneous KARPAS-422 xenografts. Mean tumor volume±s.e.m. is shown (n=10). (D) Kaplan-Meier survival curve of mice treated in (C). Significant P values, calculated using a nonparametric log-rank test, between vehicle and treatment groups are indicated. No significant differences were observed between treatment groups (p value=0.07-0.32).

FIG. 20 Pharmacokinetic analysis of GSK126. (A) Blood and tumor distribution following intraperitoneal administration of 50 mg/kg GSK126 of female beige SCID mice bearing Pfeiffer xenografts. Three mice were evaluated at each timepoint. (B) Are a under the curve (AUC0-1440), tumor/blood AUC ratio, maximum concentration achieved (Cmax), and time of maximum concentration (Tmax) for the data presented in a. N/A, not applicable.

FIG. 21 GSK126 inhibits tumor growth in vivo. (A) Efficacy of GSK126 on the growth of subcutaneous Pfeiffer xenografts. (B) Efficacy of intermittent dosing of GSK126 on the growth of subcutaneous KARPAS-422 xenografts with or without a 1 week drug holiday. Values are the mean tumor volume±standard error (n=10). P values were calculated using a nonparametric log-rank test comparing vehicle and each treatment group.

Figure 22:
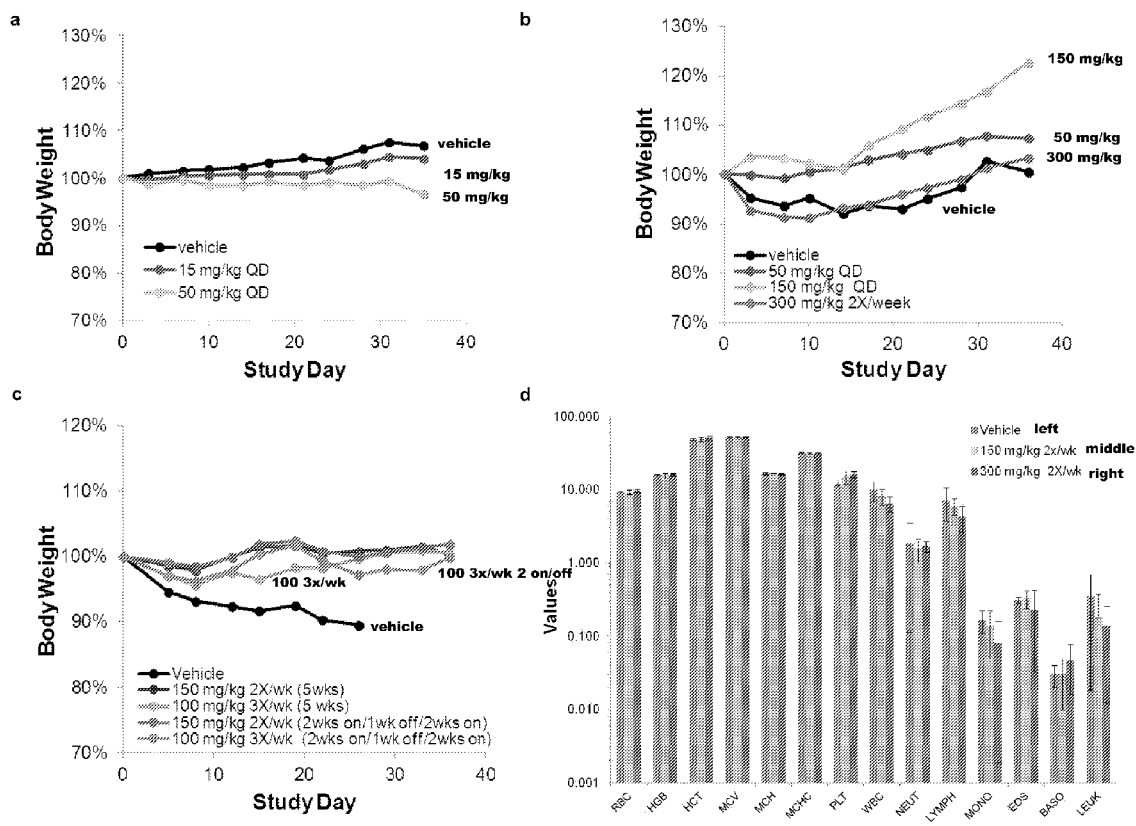

FIG. 22 Effect of GSK126 on bodyweight and peripheral blood. (A-C) Average body weight measurements of mice bearing Pfeiffer (A) or KARPAS-422 (B,C) subcutaneous xenografts during treatment with vehicle or GSK126. Values are represented as a percentage of the average weight at the start of dosing. (D) Complete blood count analysis of CD-1 mice following twice weekly dosing over 18 days. RBC, red blood cells (×106 cells/μl); HGB, hemoglobin (g/dl); HCT, hematocrit (percent); MCV, mean corpuscle volume (fl); MCH, mean corpuscle hemoglobin (pg); MCHC, mean corpuscle hemoglobin concentration (g/dl); PLT, platelets (×105 platelets/μl); WBC, white blood cells (×103 cells/μl); NEUT, neutrophils (×103 cells/μl); LYMPH, lymphocytes (×103 cells/μl); MONO, monocytes (×103 cells/μl); EOS, eosinophils (×103 cells/μl); BASO, basophils (×103 cells/μl); LEUK, leukocytes (×103 cells/μl).

Figure 23:
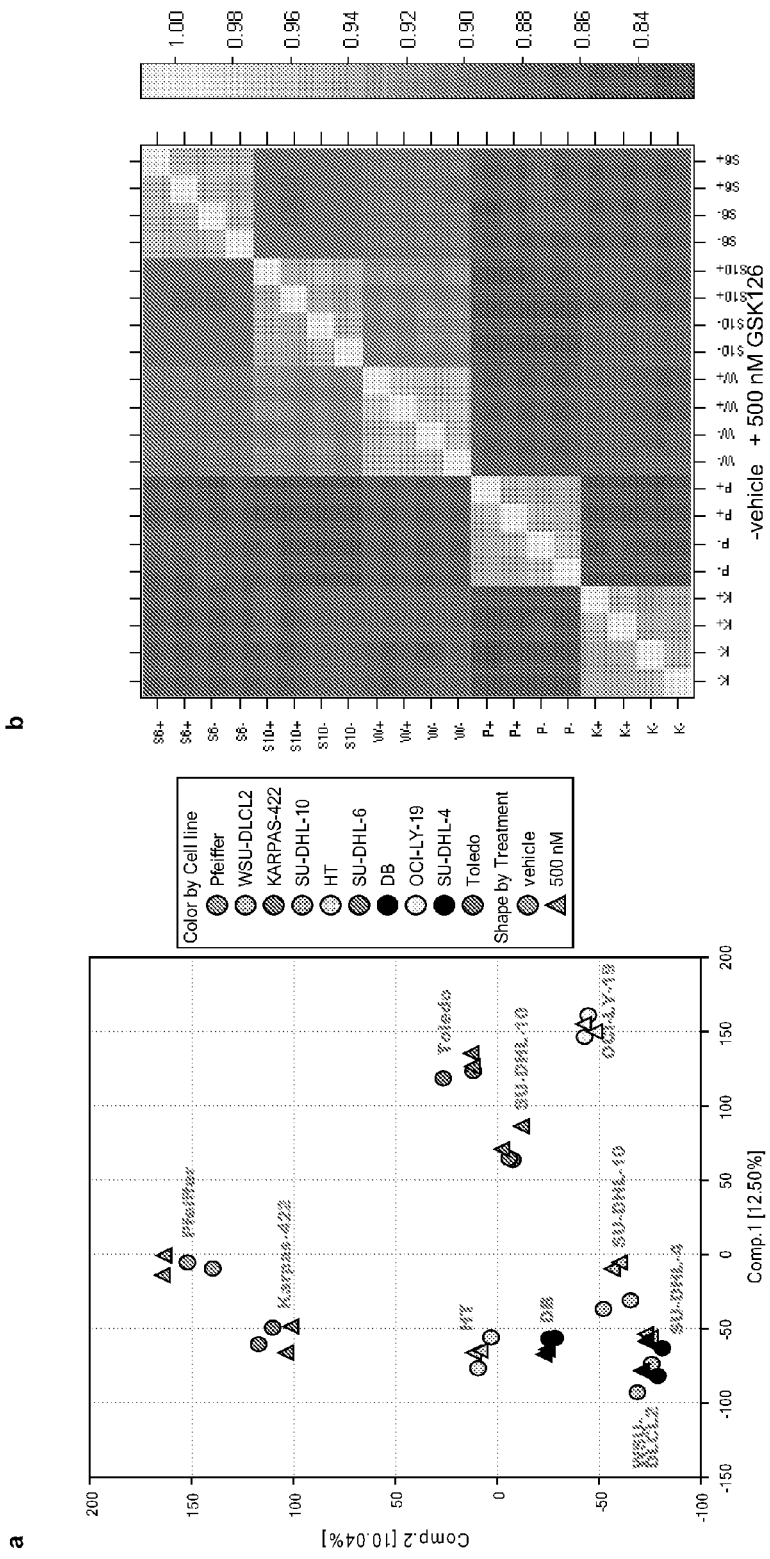

FIG. 23 Principal component and correlation analysis of gene expression profiling data. (A) PCA plot of data from biological replicates of 10 DLBCL cell lines treated for 72 hours with vehicle or 500 nM GSK126. (B) Correlation of biological replicates of DLBCL cell lines with robust transcriptional changes. K, KARPAS-422; P, Pfeiffer; W, WSU-DLCL2; S10, SU-DI-IL-10; S6, SU-DHL-6.

FIG. 24 Table 5: H3K27me3 levels, EZH2 mutation status and growth IC50 values in a panel of lymphoma cell lines FIG. 25 Table 6: Growth IC50 value, baseline H3K27me3 levels, mutation status, and tumor subtype for lymphoma cell lines FIG. 26 Table 7: Common upregulated genes in at least 4 out of 5 sensitive mutant cell lines

DETAILED DESCRIPTION OF THE INVENTION

Recent genome-wide sequencing studies have revealed several genes that are frequently altered in non-Hodgkin's lymphomas, including EZH2, MLL2, MEF2B, CREBBP, and TP53 among others (1-3). Many of these genes mediate, either directly or indirectly through the recruitment of co-factors, the array of post-translational modifications observed on the amino-terminal tails of histones. In addition, similar studies have also implicated these and other epigenetic factors in transitional cell carcinoma of the bladder (e.g. UTX, ARID1A, MLL, MLL3), head and neck squamous cell cancers (e.g. EZH2, MLL2), and myeloid malignancies (e.g. IDH1/2, TET2, DNMT3A, EZH2) (4-6). The prevalence of genetic changes affecting transcription factors and histone modifying genes highlights the importance of maintaining proper transcriptional regulation in tumorigenesis.

The EZH2 gene encodes a SET domain-containing lysine methyltransferase that along with EED, SUZ12, RbAp48, and AEBP2 forms the Polycomb Repressive Complex 2 (PRC2) (7, 8). EZH2 is responsible for methylation of the histone H3 lysine 27 (H3K27) residue which is generally associated with transcriptional repression when present in the di- or trimethylated states (7-9). EZH2 is highly expressed in pro-B cells and progressively decreases in expression as cells progress into pre-B cells, immature B cells, and re-circulating B cells (10). EZH2 expression is required in the bone marrow for progression of pro-B cells into pre-B cells and immature B cells as genetic inactivation of EZH2 leads to an accumulation of cells at the pro-B cell stage (10). However, if EZH2 is inactivated after the pro-B cell stage, additional maturation steps are not hindered suggesting that EZH2 functions early in B-cell differentiation (10). In fact, multiple groups have shown EZH2 to play an important role in the maintenance of hematopoietic stem and progenitor cells (11, 12). In particular, EZH2 over-expression in hematopoietic stem cells (HSC) leads to continued self-renewal capacity in serial transplantation models suggesting that EZH2 contributes to repopulating potential and helps cells resist replicative stress (11).

EZH2 is frequently amplified and/or over-expressed in most solid tumor types (13); however, this does not appear to be the case in lymphomas perhaps owing to the high basal expression of EZH2 in normal proliferating B-cells. Instead EZH2 has been reported to harbor recurrent mutation of the tyrosine 641 (Y641) residue in 22% of germinal center B-cell (GCB) diffuse large B-cell lymphoma (DLBCL) and in 7% of follicular lymphomas (FL) (3). Although initially reported to be a loss-of-function mutation (3), subsequent biochemical work demonstrated a novel gain-of-function activity for this Y641 mutant EZH2 (14, 15). While wild-type EZH2 exhibits a strong preference for unmethylated and mono-methylated H3K27 substrates, the Y641 EZH2 mutants observed in lymphomas (Y641F/N/S/H) exhibit profoundly increased activity for di-methylated substrates and a lack of activity for unmethylated and mono-methylated H3K27 (14, 15). Through the coordinated activities of wild-type and mutant EZH2 proteins there is a global increase in tri-methylation of H3K27 (H3K27me3) in Y641 mutant lymphomas concomitant with a decrease in mono- and di-methylated H3K27 (14).

These EZH2 Y641 mutations, along with EZH2 overexpression in many tumors, suggest that deregulation of H3K27me3 levels is important in human tumorigenesis. Indeed, H3K27me3 levels correlate with progression-free survival in renal cell carcinoma (16) and disease severity and poor tumor differentiation in esophageal squamous cell carcinoma (17). In addition to mutation of EZH2 Y641, additional mechanisms for deregulation of H3K27me3 include inactivating mutations of the H3K27 demethylase UTX (4, 18, 19) and over-expression of EZH2 due to multiple mechanisms including decreased miR-101 levels (20, 21), aberrant E2F activity (22), and chromosomal amplification (23).

Through the investigation of global H3K27me3 levels in more than 100 cell lines, we have identified a novel EZH2 mutation at the A677 residue that is responsible for increased H3K27me3 in some lymphoma cells. Characterization of this mutant protein revealed that similar to the Y641 EZH2 mutations, exchange of the alanine at position 677 for glycine (A677G) leads to increased activity with a di-methylated H3K27 substrate. Importantly, however, this substitution retains critical interactions present in wild-type EZH2 leading to efficient utilization of all H3K27 methylation states including un-, mono-, and di-methylation. This mutation presents a unique approach for cells to deregulate H3K27 methylation without requiring cooperation with wild-type EZH2 as is the case for Y641 EZH2 mutants.

The present invention provides methods for treating cancer in a human in need thereof, comprising determining at least one of the following in a sample from said human:
  a. the presence or absence of a mutation at the alanine 677 (A677) residue in EZH2 in a sample from said human; or
  b. the presence or absence of a mutation at the tyrosine 641 (Y641) residue in EZH2; or
  c. the presence or absence of an increased level of H3K27me3 as compared to a control,
and administering to said human an effective amount of an EZH2 inhibitor, e.g. a compound of the invention described herein, or a pharmaceutically acceptable salt thereof if at least one of said A677 mutation, Y641 mutation, or increased level of H3K27me3 is present in said sample.

In certain embodiments of the methods herein, at least two of a, b, and c are determined, e.g. a and b, a and c, or b and c, in any order. In a further embodiment, a, b, and c are each determined, and an EZH2 inhibitor, such as a compound of the invention as described herein, is administered if it is determined that any one of the A677 mutation, the Y641 mutation, or an increased level of H3K27me3 as compared to a control, is present.

In further embodiments, the presence or absence of a Y641 mutation is determined and the Y641 mutation is Y641F, Y641S, Y641H, Y641N, or Y641C. In other further embodiments, the presence or absence of an A677 mutation is determined and the A677 mutation is A677G.

In further embodiments, an increase in the level of global methylation of a cancer cell or tumor cell is determined. In other embodiments, the level of H3K27 methylation are determined. In other embodiments, the level of H3K27me0, H3K27me1, H3K27me2, and H3K27me3 are determined and an increase in the level of H3K27me3 suggests treatment with an EZH2 inhibitor. In further embodiments of the invention in this paragraph, the levels of methylation are compared to a control, and relative increase in methylation relative to a control suggests treatment with an EZH2 inhibitor.

Methods of detecting a mutation in EZH2 at Y641 or A677 are well known to one of skill in the art and are described herein in the detailed description and Examples. Methods of determining an increased level of methylation, e.g, H3K27me3, relative to a control are well known in the art and shown in the Examples, and include using an antibody specific for trimethylated lysine 27 of Histone 3. A control can be any one of skill in the art would choose, such as a matched cell from a human, a matched tissue from a human, a cell of the same origin as the tumor but known to have wild type EZH2, or a devised control that correlates with what is seen in non-cancerous cells of the same origin or in cells with wild-type EZH2.

In other embodiments of the invention, the sample comprises at least one cancer cell. In certain such embodiments, the sample is a biological sample.

In any one of the embodiments of the invention herein, the cancer is lymphoma. In further embodiments of the method of the invention, the lymphoma is selected from the group consisting of: germinal center B-cell (GCB), Diffuse Large B-cell Lymphoma (DLBCL), Splenic marginal zone lymphoma (SMZL), Waldenström's macroglobulinemia lymphoplasmacytic lymphoma (WM), Follicular lymphoma (FL), Mantle Cell Lymphoma (MCL), and Extra nodal marginal zone B-cell lymphoma of mucosa associated lymphoid tissue (MALT).

In embodiments of the methods of the methods of the invention herein, the A677 mutation and/or the Y641 mutation is a somatic mutation.

In other embodiments of the methods of treating cancer, treatment comprises an increased response rate and/or an improved progression free survival, as compared to an untreated human.

The present invention provides methods of treating cancer in a human which comprises the following steps: (a) detecting the level of H3K27me3 from at least one tumor cell from said human and (b) administering to said human an effective amount of an EZH2 inhibitor or a pharmaceutically acceptable salt thereof in a pharmaceutical composition if said at least one tumor cell has a high level of H3K27me3.

The present invention also relates to a method of treating cancer in a human which comprises the following steps: (a) performing a genotyping technique on a biological sample from the subject tumor to determine whether said tumor has somatic mutations of EZH2 at the tyrosine 641 (Y641) residue; and (b) correlating the detection of said mutations with increased likelihood of increased response rate and/or prolonged progression free survival when administered an EZH2 inhibitor.

The present invention also relates to a method of treating cancer in a human which comprises the following steps: (a) performing a genotyping technique on a biological sample from the subject tumor to determine whether said tumor has somatic mutations of EZH2 at the tyrosine 641 (Y641) residue; and (b) administer an effective amount of an EZH2 inhibitor or a pharmaceutically acceptable salt thereof to said human if said tumor has a mutation of EZH2 at the tyrosine 641 residue.

The present invention also relates to a method of treating cancer in a human which comprises the following steps: (a) performing a genotyping technique on a biological sample from the subject tumor to determine whether said tumor has somatic mutations of EZH2 at the tyrosine 641 (Y641) residue; and (b) administer an effective amount of an EZH2 inhibitor or a pharmaceutically acceptable salt thereof to said human if said tumor has a mutation of EZH2 at the tyrosine 641 residue, wherein such EZH2 mutation is Y641N, Y641F, Y641S, Y641H, or Y641C.

The present invention also relates to a method of treating cancer in a human which comprises the following steps: (a) performing a genotyping technique on a biological sample from the subject tumor to determine whether said tumor has somatic mutations of EZH2 at the A677 residue; and (b) correlating the detection of said mutations with increased likelihood of increased response rate and/or prolonged progression free survival when administered an EZH2 inhibitor.

The present invention also relates to a method of treating cancer in a human which comprises the following steps: (a) performing a genotyping technique on a biological sample from the subject tumor to determine whether said tumor has somatic mutations of EZH2 at the A677 residue; and (b) administering an effective amount of an EZH2 inhibitor or a pharmaceutically acceptable salt thereof to said human if said tumor has a mutation of EZH2 at the A677 residue.

The present invention also relates to a method of treating cancer in a human which comprises the following steps: (a) performing a genotyping technique on a biological sample from the subject tumor to determine whether said tumor has somatic mutations of EZH2 at the A677 residue; and (b) administering an effective amount of an EZH2 inhibitor or a pharmaceutically acceptable salt thereof to said human if said tumor has a mutation of EZH2 at the A677 residue; wherein such EZH2 mutation is A677G.

Definitions

The term "wild type" as is understood in the art refers to a polypeptide or polynucleotide sequence that occurs in a native population without genetic modification. As is also understood in the art, a "variant" includes a polypeptide or polynucleotide sequence having at least one modification to an amino acid or nucleic acid compared to the corresponding amino acid or nucleic acid found in a wild type polypeptide or polynucleotide, respectively. Included in the term variant is Single Nucleotide Polymorphism (SNP) where a single base pair distinction exists in the sequence of a nucleic acid strand compared to the most prevalently found (wild type) nucleic acid strand.

As used herein "genetic modification" or "genetically modified" or grammatical variations thereof refers to, but is not limited to, any suppression, substitution, amplification, deletion and/or insertion of one or more bases into DNA sequence(s). Also, as used herein "genetically modified" can refer to a gene encoding a polypeptide or a polypeptide having at least one deletion, substitution or suppression of a nucleic acid or amino acid, respectively. Genetic variants and/or SNPs can be identified by known methods. For example, wild type or SNPs can be identified by DNA amplification and sequencing techniques, DNA and RNA detection techniques, including, but not limited to Northern and Southern blot, respectively, and/or various biochip and array technologies. WT and mutant polypeptides can be detected by a variety of techniques including, but not limited to immunodiagnostic techniques such as ELISA and western Blot. As used herein, the process of detecting an allele or polymorphism includes but is not limited to serologic and genetic methods. The allele or polymorphism detected may be functionally involved in affecting an individual's phenotype, or it may be an allele or polymorphism that is in linkage disequilibrium with a functional polymorphism/allele. Polymorphisms/alleles are evidenced in the genomic DNA of a subject, but may also be detectable from RNA, cDNA or protein sequences transcribed or translated from this region, as will be apparent to one skilled in the art.

As is well known genetics, nucleotide and related amino acid sequences obtained from different sources for the same gene may vary both in the numbering scheme and in the precise sequence. Such differences may be due to numbering schemes, inherent sequence variability within the gene, and/or to sequencing errors. Accordingly, reference herein to a particular polymorphic site by number will be understood by those of skill in the art to include those polymorphic sites that correspond in sequence and location within the gene, even where different numbering/nomenclature schemes are used to describe them.

As used herein, "genotyping" a subject (or DNA or other sample) for a polymorphic allele of a gene(s) or a mutation in at least one polypeptide or gene encoding at least one polypeptide means detecting which mutated, allelic or polymorphic form(s) of the gene(s) or gene expression products (e.g., hnRNA, mRNA or protein) are present or absent in a subject (or a sample). Related RNA or protein expressed from such gene may also be used to detect mutant or polymorphic variation. As is well known in the art, an individual may be heterozygous or homozygous for a particular allele. More than two allelic forms may exist, thus there may be more than three possible genotypes. As used herein, an allele may be 'detected' when other possible allelic variants have been ruled out; e.g., where a specified nucleic acid position is found to be neither adenine (A), thymine (T) or cytosine (C), it can be concluded that guanine (G) is present at that position (i.e., G is 'detected' or 'diagnosed' in a subject). Sequence variations may be detected directly (by, e.g., sequencing) or indirectly (e.g., by restriction fragment length polymorphism analysis, or detection of the hybridization of a probe of known sequence, or reference strand conformation polymorphism), or by using other known methods.

As used herein, a "genetic subset" of a population consists of those members of the population having a particular genotype or a tumor having at least one somatic mutation. In the case of a biallelic polymorphism, a population can potentially be divided into three subsets: homozygous for allele 1 (1,1), heterozygous (1,2), and homozygous for allele 2 (2,2). A 'population' of subjects may be defined using various criteria.

As used herein, a human that is in need of treatment for cancer, may be "predisposed to" or "at increased risk of" a particular phenotypic response based on genotyping will be more likely to display that phenotype than an individual with a different genotype at the target polymorphic locus (or loci). Where the phenotypic response is based on a multi-allelic polymorphism, or on the genotyping of more than one gene, the relative risk may differ among the multiple possible genotypes.

A human that is in need of treatment for cancer may alternatively have a tumor or cancer cells with somatic mutations, and genotyping or other detection of the mutations can be performs.

As used herein "response" to treatment and grammatical variations thereof, includes but is not limited to an improved clinical condition of a patient after the patient received medication. Response can also mean that a patient's condition does not worsen upon that start of treatment. Response can be defined by the measurement of certain manifestations of a disease or disorder. With respect to cancer, response can mean, but is not limited to, a reduction of the size and or number of tumors and/or tumor cells in a patient. Response can also be defined by a other endpoints such as a reduction or attenuation in the number of pre-tumorous cells in a patient.

"Genetic testing" (also called genetic screening) as used herein refers to the testing of a biological sample from a subject to determine the subject's genotype; and may be utilized to determine if the subject's genotype comprises alleles that either cause, or increase susceptibility to, a particular phenotype (or that are in linkage disequilibrium with allele(s) causing or increasing susceptibility to that phenotype).

Samples, e.g. biological samples, for testing or determining of one or more mutations may be selected from the group of proteins, nucleotides, cellular blebs or components, serum, cells, blood, blood components, urine and saliva. Testing for mutations may be conducted by several techniques known in the art and/or described herein.

The sequence of any nucleic acid including a gene or PCR product or a fragment or portion thereof may be sequenced by any method known in the art (e.g., chemical sequencing or enzymatic sequencing). "Chemical sequencing" of DNA may denote methods such as that of Maxam and Gilbert (1977) (Proc. Natl. Acad. Sci. USA 74:560), in which DNA is randomly cleaved using individual base-specific reactions. "Enzymatic sequencing" of DNA may denote methods such as that of Sanger (Sanger, et al., (1977) Proc. Natl. Acad. Sci. USA 74:5463).

Conventional molecular biology, microbiology, and recombinant DNA techniques including sequencing techniques are well known among those skilled in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994

The Peptide Nucleic Acid (PNA) affinity assay is a derivative of traditional hybridization assays (Nielsen et al., Science 254:1497-1500 (1991); Egholm et al., J. Am. Chem. Soc. 114:1895-1897 (1992); James et al., Protein Science 3:1347-1350 (1994)). PNAs are structural DNA mimics that follow Watson-Crick base pairing rules, and are used in standard DNA hybridization assays. PNAs display greater specificity in hybridization assays because a PNA/DNA mismatch is more destabilizing than a DNA/DNA mismatch and complementary PNA/DNA strands form stronger bonds than complementary DNA/DNA strands.

DNA microarrays have been developed to detect genetic variations and polymorphisms (Taton et al., *Science* 289: 1757-60, 2000; Lockhart et al., *Nature* 405:827-836 (2000); Gerhold et al., *Trends in Biochemical Sciences* 24:168-73 (1999); Wallace, R. W., *Molecular Medicine Today* 3:384-89 (1997); Blanchard and Hood, *Nature Biotechnology* 149: 1649 (1996)). DNA microarrays are fabricated by high-speed robotics, on glass or nylon substrates, and contain DNA fragments with known identities ("the probe"). The microarrays are used for matching known and unknown DNA fragments ("the target") based on traditional base-pairing rules.

The terms "polypeptide" and "protein" are used interchangeably and are used herein as a generic term to refer to native protein, fragments, peptides, or analogs of a polypeptide sequence. Hence, native protein, fragments, and analogs are species of the polypeptide genus.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "G12S" with reference to the K-ras polypeptide indicates that there is a glycine at amino acid number 12 of the wild-type K-ras sequence, and that glycine is replaced with a serine in the mutant K-ras sequence.

A "mutation" in a polypeptide or a gene encoding a polypeptide and grammatical variations thereof means a polypeptide or gene encoding a polypeptide having one or more allelic variants, splice variants, derivative variants, substitution variants, deletion variants, and/or insertion variants, fusion polypeptides, orthologs, and/or interspecies homologs. By way of example, at least one mutation of EZH2 would include an EZH2 in which part of all of the sequence of a polypeptide or gene encoding the polypeptide is absent or not expressed in the cell for at least one of the EZH2 proteins produced in the cell. For example, an EZH2 protein may be produced by a cell in a truncated form and the sequence of the truncated form may be wild type over the sequence of the truncate. A deletion may mean the absence of all or part of a gene or protein encoded by a gene. An EZH2 mutation also means a mutation at a single base in a polynucleotide, or a single amino acid substitution. Additionally, some of a protein expressed in or encoded by a cell may be mutated, e.g., at a single amino acid, while other copies of the same protein produced in the same cell may be wild type.

Mutations may be detected in the polynucleotide or translated protein by a number of methods well known in the art. These methods include, but are not limited to, sequencing, RT-PCR, and in situ hybridization, such as fluorescence-based in situ hybridization (FISH), antibody detection, protein degradation sequencing, etc. Epigenetic changes, such as methylation states, may also result in mutations and/or lack of expression of part or all of a protein from the corresponding polynucleotide encoding it.

As used herein "genetic abnormality" is meant a deletion, substitution, addition, translocation, amplification and the like relative to the normal native nucleic acid content of a cell of a subject. As used herein "gene encoding an EZH2 protein" means any part of a gene or polynucleotide encoding any EZH2 protein. Included within the meaning of this term are exons encoding EZH2. Gene encoding EZH2 proteins include but are not limited to genes encoding part or all of EZH2.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes, although oligonucleotides may be double stranded, e.g. for use in the construction of a gene mutant. Oligonucleotides can be either sense or antisense oligonucleotides.

An oligonucleotide probe, or probe, is a nucleic acid molecule which typically ranges in size from about 8 nucleotides to several hundred nucleotides in length. Such a molecule is typically used to identify a target nucleic acid sequence in a sample by hybridizing to such target nucleic acid sequence under stringent hybridization conditions. Hybridization conditions have been described in detail above.

PCR primers are also nucleic acid sequences, although PCR primers are typically oligonucleotides of fairly short length which are used in polymerase chain reactions. PCR primers and hybridization probes can readily be developed and produced by those of skill in the art, using sequence information from the target sequence. (See, for example, Sambrook et al., supra or Glick et al., supra).

As used herein "overexpressed" and "overexpression" and grammatical variations thereof means that a given cell produces an increased number of a certain protein relative to a normal cell. For instance, some tumor cells are known to overexpress Her2 or Erb2 on the cell surface compared with cells from normal breast tissue. Gene transfer experiments have shown that overexpression of HER2 will transform NIH 3T3 cells and also cause an increase in resistance to the toxic macrophage cytokine tumor necrosis factor. Hudziak et al., "Amplified Expression of the HER2/ERBB2 Oncogene Induces Resistance to Tumor Necrosis Factor Alpha in NIH 3T3 Cells", Proc. Natl. Acad. Sci. USA 85, 5102-5106 (1988). Expression levels of a polypeptide in a particular cell can be effected by, but not limited to, mutations, deletions and/or substitutions of various regulatory elements and/or non-encoding sequence in the cell genome.

As used herein, "treatment" means any manner in which one or more symptoms associated with the disorder are beneficially altered. Accordingly, the term includes healing or amelioration of a symptom or side effect of the disorder or a decrease in the rate of advancement of the disorder.

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. Tumors may be hematopoietic tumor, for example, tumors of blood cells or the like. Specific examples of clinical conditions based on such a tumor include leukemia such as chronic myelocytic leukemia or acute myelocytic leukemia; myeloma such as multiple myeloma; lymphoma and the like.

The cancer may be any cancer in which an abnormal number of blast cells are present or that is diagnosed as a haematological cancer or dysplasia, such as leukemia, myeloid malignancy or myeloid dysplasia, including but not limited to, undifferentiated acute myelogenous leukemia, myeloblastic leukemia, myeloblastic leukemia, promyelocytic leukemia, myelomonocytic leukemia, monocytic leukemia, erythroleukemia and megakaryoblastic leukemia. In one aspect, the cancer is a myeloid malignancy cancer. In another aspect, the cancer is leukemia. The leukemia may be acute lymphocytic leukemia, acute non-lymphocytic leukemia, acute myeloid leukemia (AML), chronic lymphocytic leukemia, chronic myelogenous (or myeloid) leukemia (CML), and chronic myelomonocytic leukemia (CMML). In one embodiment, the human has agnogenic myeloid metaplasia and/or poor-risk myelodysplasia (MDS). In some aspects the cancer is relapsed or refractory.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphomas (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

In some embodiments, the sample is selected from the group consisting of cancer cells, tumor cells, cells, blood, blood components, urine and saliva.

Compounds of the Invention

In certain embodiments of the methods of treating cancer in a human in need thereof, the EZH2 inhibitor is of Formula I:

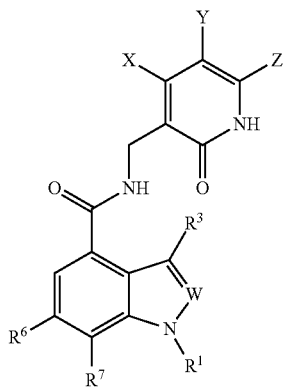

wherein:

W is N or $CR^2$;

X and Z are each independently selected from the group consisting of hydrogen, $(C_1-C_8)$alkyl, $(C_2-C_8)$alkenyl, $(C_2-C_5)$alkynyl, unsubstituted or substituted $(C_3-C_5)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, halogen, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is hydrogen or halogen;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C_{10})$bicycloalkyl, unsubstituted or substituted heterocycloalkyl or —$(C_2-C_8)$alkenyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, or —$CONR^aNR^aR^b$;

When present $R^2$ is hydrogen, $(C_1-C_8)$alkyl, trifluoromethyl, alkoxy, or halogen, in which said $(C_1-C_8)$alkyl may be substituted with one to two groups selected from amino and $(C_1-C_3)$alkylamino;

$R^7$ is hydrogen, $(C_1-C_3)$alkyl, or alkoxy; $R^3$ is hydrogen, $(C_1-C_8)$alkyl, cyano, trifluoromethyl, —$NR^aR^b$, or halogen;

$R^6$ is selected from the group consisting of hydrogen, halo, $(C_1-C_8)$alkyl, $(C_2-C_8)$alkenyl, —$B(OH)_2$, substituted or unsubstituted $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^C)_{1-2}$, —$S(C_1-C_6)$alkyl$(R^C)_{1-2}$, —$(C_1-C_6)$alkyl$(R^C)_{1-2}$, $(C_1-C_8)$alkyl-heterocycloalkyl, $(C_3-C_8)$cycloalkyl-heterocycloalkyl, halogen, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halogen, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

each $R^c$ is independently $(C_1-C_4)$alkylamino, —$NR^aSO_2R^b$, —$SOR^a$, —$SO_2R^a$, —$NR^aC(O)OR^a$, —$NR^aR^b$, or —$CO_2R^a$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from halogen, hydroxyl, $(C_1-C_4)$alkoxy, amino, $(C_1-C_4)$alkylamino, (($C_1-C_4$)alkyl)(($C_1-C_4$)alkyl)amino, —$CO_2H$, —$CO_2(C_1-C_4)$alkyl, —$CONH_2$, —$CONH(C_1-C_4)$alkyl, —$CON((C_1-C_4)$ alkyl)((C$_1$-C$_4$)alkyl), —SO$_2$(C$_1$-C$_4$)alkyl, —SO$_2$NH$_2$, —SO$_2$NH(C$_1$-C$_4$)alkyl, or —SO$_2$N((C$_1$-C$_4$)alkyl)((C$_1$-C$_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from (C$_1$-C$_4$)alkyl, (C$_1$-C$_4$)haloalkyl, amino, (C$_1$-C$_4$)alkylamino, ((C$_1$-C$_4$)alkyl)((C$_1$-C$_4$)alkyl)amino, hydroxyl, oxo, (C$_1$-C$_4$)alkoxy, and (C$_1$-C$_4$)alkoxy(C$_1$-C$_4$)alkyl, wherein said ring is optionally fused to a (C$_3$-C$_5$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring;

or a pharmaceutically acceptable salt thereof.

Compounds of Formula I, and methods of making the same are disclosed in WO2011/140324, which is incorporated by reference in its entirety herein.

In a further embodiment, EZH2 inhibitor is a compound of Formula (I) wherein W is CR$^2$, or a pharmaceutically acceptable salt thereof.

In yet a further embodiment, the EZH2 inhibitor is a Compound of Formula I having Formula B:

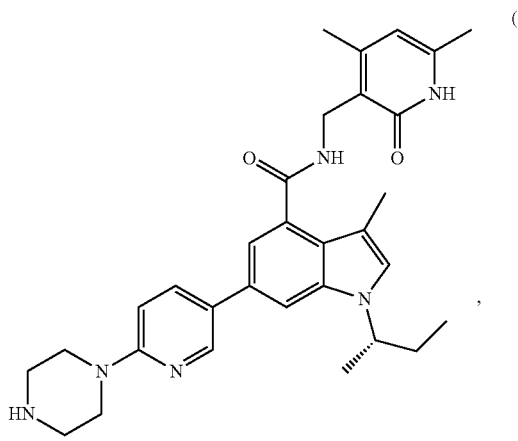

(B)

or a pharmaceutically acceptable salt thereof.

Compounds having Formula B and methods of making the same are disclosed in WO 2011/140324, e.g. Example 270.

In another embodiment, the EZH2 inhibitor is Compound A having formula 1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indazole-4-carboxamide;

Additional EZH2 inhibitors are well known in the art. For example, EZH2 inhibitors are disclosed in WO 2011/140324, WO 2011/140325 and WO 2012/075080, each of which is incorporated by reference herein in its entirety. In any of the embodiments herein, the EZH2 inhibitor may be a compound disclosed in WO 2011/140324, WO 2011/140325 or WO 2012/075080.

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "C$_1$C$_8$alkyl" refers to an alkyl group having at least 1 and up to 8 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, and n-octyl and branched analogs of the latter 5 normal alkanes.

The term "alkoxy" as used herein means —O(C$_1$C$_8$alkyl) including —OCH$_3$, —OCH$_2$CH$_3$ and —OC(CH$_3$)$_3$ and the like per the definition of alkyl above.

The term "alkylthio" as used herein is meant —S(C$_1$C$_8$alkyl) including —SCH$_3$, —SCH$_2$CH$_3$ and the like per the definition of alkyl above.

The term "acyloxy" means —OC(O)C$_1$C$_8$alkyl and the like per the definition of alkyl above.

"Acylamino" means —N(H)C(O)C$_1$C$_8$alkyl and the like per the definition of alkyl above.

"Aryloxy" means —O(aryl), —O(substituted aryl), —O(heteroaryl) or —O(substituted heteroaryl).

"Arylamino" means —NH(aryl), —NH(substituted aryl), —NH(heteroaryl) or —NH(substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group that is substituted with one or more halogen substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "C$_3$-C$_8$cycloalkyl" refers to a non-aromatic cyclic hydrocarbon ring having from three to eight carbon atoms. Exemplary "C$_3$-C$_8$cycloalkyl" groups useful in the present invention include, but are not limited to, cyclopropyl, cyclobutyl, cyclopentyl, cyclohexyl, cycloheptyl and cyclooctyl.

The term "C$_5$C$_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "C₃C₈heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples are given herein below.

"Aryl" refers to optionally substituted monocyclic or polycarbocyclic unfused or fused groups having 6 to 14 carbon atoms and having at least one aromatic ring that complies with Hückel's Rule. Examples of aryl groups are phenyl, biphenyl, naphthyl, anthracenyl, phenanthrenyl, and the like, as further illustrated below.

"Heteroaryl" means an optionally substituted aromatic monocyclic ring or polycarbocyclic fused ring system wherein at least one ring complies with Hückel's Rule, has the specified number of ring atoms, and that ring contains at least one heteroatom independently selected from N, O and S. Examples of "heteroaryl" groups are given herein below.

The term "optionally" means that the subsequently described event(s) may or may not occur, and includes both event(s), which occur, and events that do not occur.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

Pharmaceutical Formulations

While it is possible that, the compound of the present invention, as well as pharmaceutically acceptable salts and solvates thereof, may be administered as the raw chemical, it is also possible to present the active ingredient as a pharmaceutical composition. Accordingly, embodiments of the invention further provide pharmaceutical compositions, which include therapeutically effective amounts of a compound of Formula (I), or Compound A, or Compound B and one or more pharmaceutically acceptable carriers, diluents, or excipients. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of Formula I, Compound A, or Compound B with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 800 mg, of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known by one of skill in the art, e.g. in the pharmacy art Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

Dosage unit forms can also be in the form for i.v. delivery, of which one of skill in the art is capable of providing.

Dosage unit forms, e.g. for i.v. delivery, can also be in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines or other forms familiar to one of skill in the art.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of formula (I) or a pharmaceutically acceptable salt thereof will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) or a salt thereof for the treatment of a cancerous condition such as those described herein will generally be in the range of 0.1 to 100 mg/kg body weight of recipient (mammal) per day and more usually in the range of 1 to 12 mg/kg body weight per day. Thus, for a 70 kg adult mammal, the actual amount per day would usually be from 70 to 840 mg and this amount may be given in a single dose per day or more usually in a number (such as two, three, four, five or six) of sub-doses per day such that the total daily dose is the same. An effective amount of a salt or solvate thereof may be determined as a proportion of the effective amount of the compound of formula (I) per se. It is envisaged that similar dosages would be appropriate for treatment of the other conditions referred to above.

The amount of administered or prescribed compound according to these aspects of the present invention will depend upon a number of factors including, for example, the age and weight of the patient, the precise condition requiring treatment, the severity of the condition, the nature of the formulation, and the route of administration. Ultimately, the amount will be at the discretion of the attendant physician.

Combinations and Additional Anti-Neoplastic Agents

In certain embodiments, the methods of the present invention further comprise administering one or more additional anti-neoplastic agents.

When an EZH2 inhibitor such as, but not limited to, Formula I, Compound A, or Compound B, is administered for the treatment of cancer, the term "co-administering" and derivatives thereof as used herein is meant either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. If the administration is not simultaneous, the compounds are administered in a close time proximity to each other. Furthermore, it does not matter if the compounds are administered in the same dosage form, e.g. one compound may be administered topically or intravenously (i.v.) and another compound may be administered orally.

Typically, any anti-neoplastic agent that has activity versus a susceptible tumor or cancer (e.g. lymphoma) being treated may be co-administered in the treatment of cancer in the present invention. Examples of such agents can be found in Cancer Principles and Practice f Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, any treatment for lymphoma, such as: R-CHOP, the five component treatment for non-Hodgkin's lymphoma, comprising: Rituximab, Cyclophosphamide, a DNA alkylating cross-linking agent; Hydroxydaunorubicin (i.e. doxorubicin or Adriamycin), a DNA intercalating agent; Oncovin (vincristine), which inhibits cell division by binding to the protein tubulin, and the corticosteroids Prednisone or prednisolone; CHOP, R-CVP (similar to R-CHOP, comprises rituximab, cyclophosphamide, vincristine, and prednisolone/prednisone), CVP; bortezomib; bendamustin; alemtuzumab; and radioimmunotherapy (e. ibritumomab (Zevalin), tositumomab (Bexxar)).

Other typical anti-neoplastic agents useful in the present invention include, but are not limited to. Class I and Class II histone deacetylase (HDAC) inhibitors (e.g., vorinostat), DNA methylase inhibitors (e.g. decitabine or azacitidine), histone acetyltransferase (HAT) inhibitors (e.g. p300 and PCAF inhibitors), anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present EZH2 inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β, 10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-co-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1, 7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyl adenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula F following, currently under development, including the racemic mixture (R,S) form as well as the R and S enantiomers:

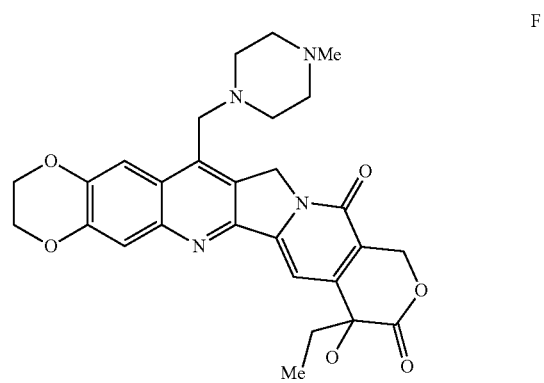 [SMILES: CCC1(O)C(=O)OCc2c1cc1n(c2=O)Cc2c-1nc1cc3c(cc1c2CN1CCN(C)CC1)OCCO3]

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Letrozole (trade name Femara) is an oral non-steroidal aromatase inhibitor for the treatment of hormonally-responsive breast cancer after surgery. Estrogens are produced by the conversion of androgens through the activity of the aromatase enzyme. Estrogens then bind to an estrogen receptor, which causes cells to divide. Letrozole prevents the aromatase from producing estrogens by competitive, reversible binding to the heme of its cytochrome P450 unit. The action is specific, and letrozole does not reduce production of mineralo- or corticosteroids.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and Bennett, C. F. and Cowsert, L. M. BioChim. Biophys. Acta, (1999) 1489(1):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Pazopanib which commercially available as VOTRIENT® is a tyrosine kinase inhibitor (TKI). Pazopanib is presented as the hydrochloride salt, with the chemical name 5-[[4-[(2,3-dimethyl-2H-indazol-6-yl)methylamino]-2-pyrimidinyl]amino]-2-methylbenzenesulfonamide monohydrochloride. Pazoponib is approved for treatment of patients with advanced renal cell carcinoma.

Bevacisumab which is commercially available as AVASTIN® is a humanized monoclonal antibody that blocks VEGF-A. AVASTIN® is approved form the treatment of various cancers including colorectal, lung, breast, kidney, and glioblastomas.

mTOR inhibitors include but are not limited to rapamycin (FK506) and rapalogs, RAD001 or everolimus (Afinitor), CCI-779 or temsirolimus, AP23573, AZD8055, WYE-354, WYE-600, WYE-687 and Pp121.

Everolimus is sold as Afinitor® by Novartis and is the 40-O-(2-hydroxyethyl) derivative of sirolimus and works similarly to sirolimus as an mTOR (mammalian target of rapamycin) inhibitor. It is currently used as an immunosuppressant to prevent rejection of organ transplants and treatment of renal cell cancer. Much research has also been conducted on everolimus and other mTOR inhibitors for use in a number of cancers. It has the following chemical structure (formula V) and chemical name:

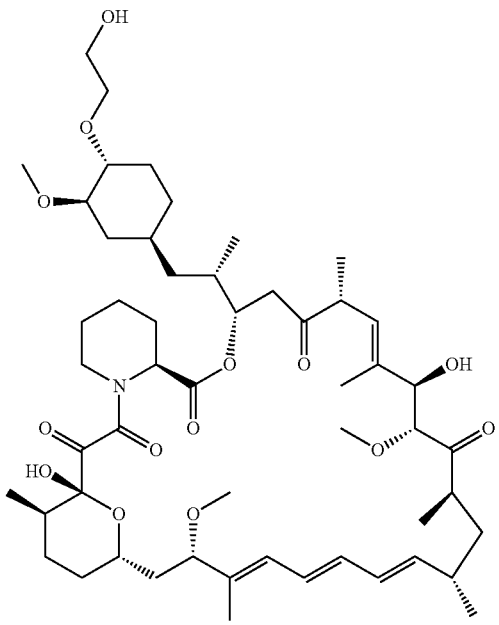

(V)

dihydroxy-12-[(2R)-1-[(1S,3R,4R)-4-(2-hydroxy-ethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone.

Bexarotene is sold as Targretin® and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl) ethenyl] benzoic acid. Bexarotene is used to treat cutaneous T-cell lymphoma (CTCL, a type of skin cancer) in people whose disease could not be treated successfully with at least one other medication.

Sorafenib marketed as Nexavar@ is in a class of medications called multikinase inhibitors. Its chemical name is 4-[4-[[4-chloro-3-(trifluoromethyl)phenyl]carbamoylamino]phenoxy]-N-methyl-pyridine-2-carboxamide.
Sorafenib is used to treat advanced renal cell carcinoma (a type of cancer that begins in the kidneys). Sorafenib is also used to treat unresectable hepatocellular carcinoma (a type of liver cancer that cannot be treated with surgery).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Examples of erbB inhibitors include lapatinib, erlotinib, and gefitinib. Lapatinib, N-(3-chloro-4-{[(3-fluorophenyl)methyl]oxy}phenyl)-6-[5-({[2-(methylsulfonyl)ethyl]amino}methyl)-2-furanyl]-4-quinazolinamine (represented by Formula VI, as illustrated), is a potent, oral, small-molecule, dual inhibitor of erbB-1 and erbB-2 (EGFR and HER2) tyrosine kinases that is approved in combination with capecitabine for the treatment of HER2-positive metastatic breast cancer.

gefitinib may be prepared according to the procedures of International Patent Application No. PCT/GB96/00961, filed Apr. 23, 1996, and published as WO 96/33980 on Oct. 31, 1996.

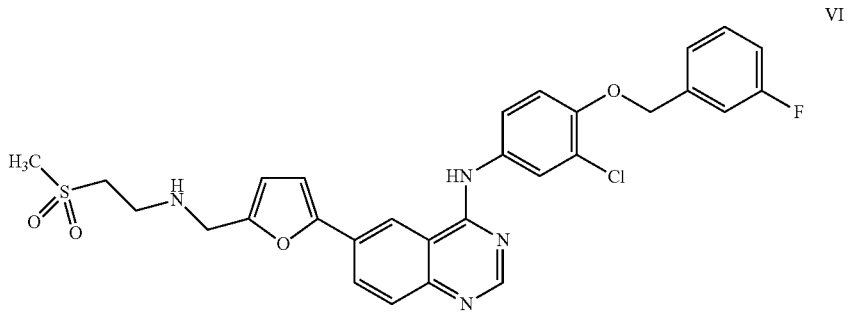 [SMILES: CS(=O)(=O)CCNCc1ccc(-c2ccc3ncnc(Nc4ccc(OCc5cccc(F)c5)c(Cl)c4)c3c2)o1]

VI

The free base, HCl salts, and ditosylate salts of the compound of formula (VI) may be prepared according to the procedures disclosed in WO 99/35146, published Jul. 15, 1999; and WO 02/02552 published Jan. 10, 2002.

Erlotinib, N-(3-ethynylphenyl)-6,7-bis{[2-(methyloxy)ethyl]oxy}-4-quinazolinamine Commercially available under the tradename Tarceva) is represented by formula VII, as illustrated:

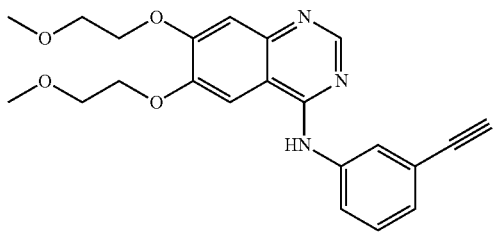

VII

The free base and HCl salt of erlotinib may be prepared, for example, according to U.S. Pat. No. 5,747,498, Example 20.

Gefitinib, 4-quinazolinamine,N-(3-chloro-4-fluorophenyl)-7-methoxy-6-[3-4-morpholin)propoxy] is represented by formula VIII, as illustrated:

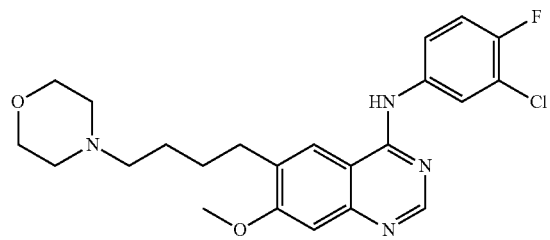

VIII

Gefitinib, which is commercially available under the trade name IRESSA® (Astra-Zenenca) is an erbB-1 inhibitor that is indicated as monotherapy for the treatment of patients with locally advanced or metastatic non-small-cell lung cancer after failure of both platinum-based and docetaxel chemotherapies. The free base, HCl salts, and diHCl salts of Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

Pertuzumab (also called 2C4, trade name Omnitarg) is a monoclonal antibody. The first of its class in a line of agents called "HER dimerization inhibitors". By binding to HER2, it inhibits the dimerization of HER2 with other HER receptors, which is hypothesized to result in slowed tumor growth. Pertuzumab is described in WO01/00245 published Jan. 4, 2001.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia (CLL; a type of cancer of the white blood cells) in adults who are refractory to treatment with fludarabine (Fludara) and alemtuzumab (Campath).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signaling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

Any of the cancer treatment methods of the claimed invention may further comprise treatment with at least one additional anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors if one of a mutation in EZH2 at Y641 or A677 or an increased level of H3K27me3 is detected.

EXAMPLES

Example 1: Cell Culture and Primary Tumor Specimens

The Pfeiffer DLBCL cell line (ATCC) was maintained in RPMI-1640 media (MediaTech) supplemented with 10% fetal bovine serum (FBS) (Sigma-Aldrich). All other cell line were obtained from either ATCC or DSMZ and maintained in the recommended cell culture media. Genomic DNA for 41 lymphoma patients was sourced from OriGene (Rockville, Md.). DNA was extracted from frozen blocks of pathology-verified tumor tissue with high tumor content (>40%). Tissues were collected for molecular analyses in accordance with IRB approval and patient informed consent. Detailed clinical characteristics of the tumor specimens are presented in Table 2.

Example 2 ELISA-Based Quantitation of Histone H3 and H3K27me3 Levels

Cell lines were harvested, rinsed with 1×PBS, and centrifuged. Cell pellets were lysed with 0.2N HCl for 30 minutes to extract histones. The acid insoluble portion was pelleted by centrifugation and the supernatant was neutralized with neutralization buffer (1M $Na_2HPO_4$, pH 12.5; ActiveMotif) containing protease inhibitors (Roche). Protein lysates and recombinant H3K27me3 (ActiveMotif) were titrated in neutralized lysis buffer and added to Maxisorp ELISA plates (Nunc) in duplicate on each of two plates. Blocking buffer (1% BSA) was added and plates were incubated for 1 hour prior to being washed 4 times with imidazole buffered saline containing Tween-20 (KPL). Plates were incubated with primary antibodies for H3K27me3 (Cell Signaling Technology) or total H3 (ActiveMotif), washed, and incubated with secondary anti-rabbit IgG HRP-linked antibody (Cell Signaling Technology). Luminata Forte substrate (Millipore) was added 5 minutes before quantifying chemiluminescence using an EnVision multi-label plate reader (PerkinElmer). H3K27me3 and total H3 levels per cell line were calculated using the recombinant H3K27me3 signals as a standard control and H3K27me3 values were normalized to total H3 values.

Example 3 Western Blot Analysis of H3K27 Methylation Status

Cell lines were rinsed with PBS and lysed on ice with RIPA buffer (Thermo Scientific) containing protease and phosphatase inhibitors (Roche). Lysates were then sonicated for 15 seconds using a Branson Sonifier 150 (setting=2) and protein concentrations were determined with a BCA protein assay (Thermo Scientific). Protein lysates (1-5□g) were then denatured and electrophoresed on Bis-Tris SDS-polyacrylamide gels (Invitrogen) before being transferred to PVDF membrane (Invitrogen). The membranes were blocked with Odyssey blocking buffer (Li-Cor) and probed with antibodies recognizing EZH2 (BD Transduction Labs), histone H3 (Abcam), H3K27me1, H3K27me3 (Cell Signaling Technology), or Actin (Sigma). After washing with PBS containing 0.1% Tween-20 (PBST), membranes were hybridized with fluorescent secondary antibodies (Li-Cor), washed with PBST, and imaged using an Odyssey infrared imaging system (Li-Cor).

Example 4 Full-Length Sanger Sequencing of EZH2

Genomic DNA (gDNA) was isolated from cell pellets using the Maxwell 16 Cell DNA Purification Kit (Promega). Total RNA was prepared using a modified RNeasy kit procedure (Qiagen) and converted into cDNA using the HiFi First Strand cDNA Synthesis Kit protocol (Roche Diagnostics). PCR reactions were carried out using primers (Table 3) tailed with the M13 universal sequencing primer sequences (Integrated DNA Technologies) and HotstarTaq DNA polymerase (Qiagen). DNA (50ng) was amplified and PCR products were purified using AmPure (Agencourt Bioscience). Direct sequencing of purified PCR products with M13 primers was performed with a 3730XL Genetic Analyzer (Applied Biosystems) using the v3.1 Big Dye-terminator cycle sequencing kit (Applied Biosystems). The sequencing reactions were analyzed and all sequences were assembled and analyzed using Codon Code Aligner (CodonCode Corporation).

Example 5 Transient Expression of Wild-Type and Mutant EZH2 Proteins in Cells MCF-7 breast cancer cells ($3 \times 10^5$; ATCC) were seeded into 6-well tissue culture plates in RPMI-1640 media supplemented with 10% FBS the day before transfection. Following the manufacturer's recommendations, 2 μg plasmid DNA and 6 μl Lipofectamine 2000 (Invitrogen) were combined in 500 μl Opti-MEM (Invitrogen) and incubated for 20 minutes at room temperature before being added to cells. Cells were then incubated at 37° C. with 5% $CO_2$ until harvested for protein lysates and western blot analysis as described above.

Example 6 Cloning, Expression, and Purification of EZH2 Wild-Type and Mutant 5-Member PRC2

Human EED1 (NM_003797), SUZ12 (NP_056170), RbAp48 (RBBP4; NP_005601), and AEBP2 (NP_694939) were cloned into pENTR/TEV/D-TOPO (Invitrogen) and sub-cloned into pDEST8 (Invitrogen). Human EZH2 (NP_001190176) was cloned into pENTR/TEV/D-TOPO and sub-cloned into pDEST8 containing an N-terminal FLAG epitope tag. Human EZH2 in pENTR/TEV/D-TOPO was mutagenized to introduce single amino acid changes of A677G, Y641N, Y641F, Y641C, Y641H, or Y641S by site-directed mutagenesis (QuikChange II XL, Agilent Technologies) (Table 4) and sub-cloned into pDEST8 containing an N-terminal FLAG epitope tag. The entire coding region of all mutants was confirmed by double stranded sequencing. For mammalian expression studies, wild-type human EZH2 was sub-cloned into pIRES2-ZsGreen1 (Clontech). Site-directed mutagenesis was then utilized as described above to obtain the A677 and Y641 mutants.

Individual baculovirus stocks were generated for expression of EED1, SUZ12, RbAp48, AEBP2, and FLAG-tev-EZH2 using the Bac-to-Bac® system (Invitrogen). All five PRC2 components were co-expressed in Sf9 insect cells by addition of $2\times10^7$ baculovirus infected insect cells per 10 L wave bag for each component. Cells were incubated at 27° C. and cell paste was harvested between 66-70 hours post-infection.

PRC2 complexes (EZH2, EED, SUZ12, AEBP2, RbAp48) containing flag-tagged wild-type EZH2 or mutant EZH2 (A677G, Y641F, Y641N, Y641S, Y641H, or Y641C) were purified from 1 L Sf9 cell paste lysate at 4° C. using 10 ml anti-FLAG M2 resin (Sigma). Resin was packed into a XK26 column and washed with Buffer A (50 mM Tris HCl pH7.5, 250 mM NaCl, 2 mM DTT). PRC2 complex was then eluted with Buffer A containing 100 μg/mL FLAG peptide (California Peptide Research). Fractions containing EZH2 were then pooled and applied to a Superdex 200 column (16/60) (GE Pharmacia) equilibrated with Buffer A. Monomer PRC2 complexes were collected, purity was assessed by SDS-PAGE, and all components and EZH2 mutations were confirmed by peptide mapping analysis.

Example 7 Biochemical Evaluation of Methyltransferase Activity

Unless stated otherwise, all reagents were obtained from Sigma and were at a minimum of reagent grade. Custom syntheses of histone H3 peptides (AA21-44; ATKAAR KSAPATGGVKKPHRYRPGG[K-Ahx-biotin]-amide) with lysine 27 unmodified, mono-methylated, or di-methylated were purchased from $21^{st}$ Century Biochemicals (Marlboro, Mass.). Peptides contained within the library were acquired from $21^{st}$ Century Biochemicals, AnaSpec (Fremont, Calif.) or Alta Bioscience (Birmingham, UK). MicroScint20, streptavidin SPA bead (RPNQ0261), and [$^3$H-]S-adenosyl-methionine (SAM) were purchased from PerkinElmer.

All reactions were evaluated at ambient temperature in assay buffer containing 50 mM Tris-HCl, (pH8.0), 2 mM MgCl$_2$, 4 mM DTT, and Tween-20 (0.001% for EZH2 peptide activity assays; 0.002% for nucleosome activity assays).

For the peptide assays, EZH2 (20 nM) was added to a 96-well reaction plate (Corning) containing varying concentrations of the H3K27 peptide and [$^3$H-]SAM. Reactions were quenched during the linear portion of their progress curves with the addition of 0.1 mM unlabeled SAM. The quenched reaction mixture was transferred to a 96-well multi-screen HTS filter plate (Millipore MSPHNXB50) that was pre-washed with 0.2 M NH$_4$HCO$_3$, pH 8.0 (wash buffer 1), and incubated for 30 minutes to allow for capture. Filter plates were then washed with four additional 150 L aliquots of wash buffer 1, and allowed to dry. MicroScint20 (60 μL/well) was added, sealed plates were incubated for 30 minutes, and quantitation of captured [$^3$H-]Me-peptide or [$^3$H-]Me-nucleosomes was monitored in a TopCount liquid scintillation counter. Output DPM's were normalized to reaction standards placed onto individual plates following filtration.

For the nucleosome assays, a similar procedure was used with the exception of the filter plates (Millipore MSDEN6B50) and wash buffer (50 mM potassium phosphate, pH7.6, wash buffer 2). Mono- and di-nucleosomes were purified from HeLa cells as described previously (35). The molecular weight of an individual mono-nucleosome unit within the heterogeneous native nucleosome preparation was estimated based on the cumulative weights of the individual histones [2×H2A (2×14.0 kDa)+2×H2B (2×13.8 kDa)+2×H3 (2×15.2 kDa)+2×H4 (2×11.2 kDa)+200 base pairs dsDNA (200×0.66 kDa)].

Rate data obtained from substrate co-titrations were fitted to Equation (1), which conforms to a sequential kinetic mechanism. For Equation (1), V is the maximal velocity, $k_{cat}$ represents V normalized to enzyme concentration, A and B represent substrate concentrations, $K_{ia}$ is the dissociation constant for A, and $K_a$ and $K_b$ are Michaelis constants for substrates A and B, respectively.

$$v = VAB/(K_{ia}K_b + K_aB + K_bA + AB) \tag{1}$$

Example 8 Structural Modeling of EZH2

A homology model of wild type EZH2 was built using GLP/EHMT1 bound to an H3K9me2 peptide substrate (PDB ID=2RFI) as a primary template and structurally compared to other related SET domain containing histone lysine methyltransferases with determined crystal structures. The homology model was constructed using the 2009 version of Molecular Operating Environment (MOE) from Chemical Computing Group (CCG). Residues were mutated in MOE and optimal orientations chosen from an exploration of rotamer geometries. For the model of the A677G mutant (FIG. 5C), the low energy rotamer of Y641 was selected after manually rotating the di-methylated lysine in an orientation optimal for tri-methylation.

Example 9 Assay Protocol to Evaluate Effects on Proliferation and Calculate Growth IC$_{50}$s (gIC50s)

Cells were cultured in appropriate medium in flasks to 80-100% confluency. Cells were harvested, counted and plated at a pre-determined optimal seeding density ranging from 50 cells per well to 4000 cells per well depending on the growth characteristics of individual cell lines in 384-well tissue culture plates (Greiner #781090). Plates were then incubated overnight at 37° C., 5% CO$_2$. Cells were treated with compound using a 20 point 1:2 fold dilution scheme with a final concentration of 0.15% DMSO. One column per plate contained cells treated with 0.15% DMSO only, and one column contained no cells to serve as background. Plates were incubated at 37° C., 5% CO$_2$ for 6 days. A time zero (t0) reading was taken on the day of compound addition. To develop the plates, 25 μL of Cell Titer Glo (Promega #G7572) was added to each well and incubated at room temperature for 12 minutes. Luminescence was measured on the Tecan Safire2.

Data were analyzed using Assay Client software. Dose response curves were generated based on percent of growth compared to t0. Growth IC50 values were calculated using a 4 parameter logistic model.

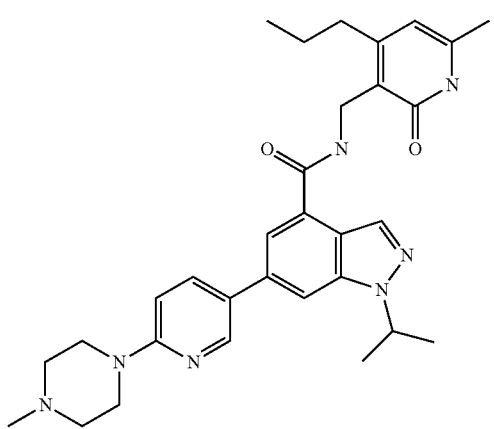

Compound A is an EZH2 inhibitor

Figure 1:
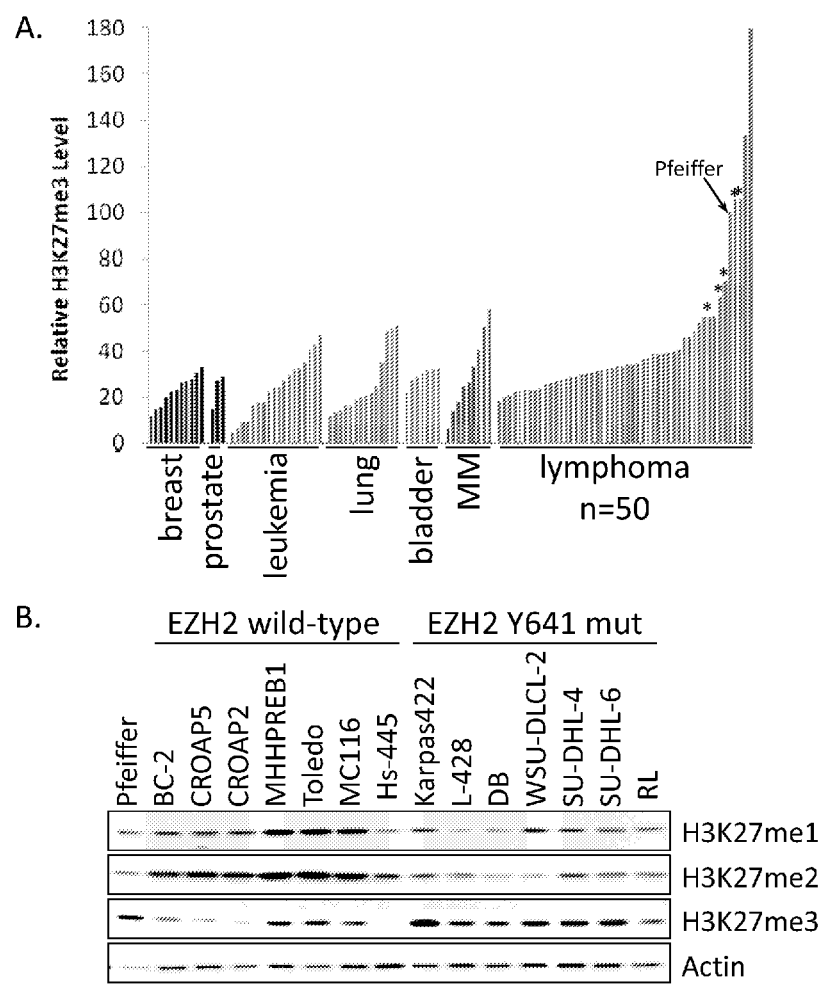
FIG. 1. A subset of lymphoma cell lines exhibit grossly elevated H3K27me3 levels. (A) Global H3K27me3 levels (normalized to total H3) were determined for 111 cancer cell lines from 7 different cancer types. Lymphoma cell lines harboring Y641 mutations are indicated by asterisks. (B) Western blot analysis of global H3K27me3 and H3K27me1 in protein lysates from a panel of lymphoma cell lines.

Example 10: Aberrantly Elevated H3K27me3 Levels in Y641 Wild-Type Lymphoma Cell Line A variety of activating and inactivating mutations of EZH2 have been described in primary tumors derived from GCB DLBCL, FL, and myelodysplastic syndrome (MDS) (1-3, 24-26). The end result of these mutations is increased or decreased methylation of H3K27 (14, 15, 24, 26). In order to characterize alterations of H3K27me3 in human cancer cell lines, we quantified global H3K27me3 and total histone H3 levels by ELISA in 111 cell lines from 7 unique tumor types (FIG. 1A). Each of the tumor types examined exhibited a range of H3K27me3 levels with several lymphoma cell lines possessing H3K27me3 levels 2-3 fold higher than the highest non-lymphoma cell lines. Further analysis of protein lysates from several of these cell lines revealed an apparent imbalance between the methylation states of H3K27 (FIG. 1B). Overall, H3K27me3 levels were increased at the expense of H3K27me1 which were reduced relative to lymphoma cell lines with lower global H3K27me3 levels.

Example 11: Mutation of the A677 Residue of EZH2 to Glycine in a Lymphoma Cell Line with Aberrantly Elevated H3K27me3

Based upon recent findings demonstrating a hyper-trimethylation phenotype for H3K27 in lymphoma cells harboring mutation of the Y641 residue of EHZ2 to either phenylalanine (F), asparagine (N), serine (S), or histidine (H), we hypothesized that the lymphoma cell lines with the highest levels of H3K27me3 may have activating mutations at Y641. Sanger sequencing of all cell lines for the Y641 codon revealed activating mutations for 6 of the top 7 lymphomas when ranked by global H3K27me3 levels.

The one cell line with high H3K27me3 levels that was not mutated at Y641 was Pfeiffer. The Pfeiffer cell line was established in 1992 from the pleural effusion of a patient in the leukemic phase of DLBCL (27). Sanger sequencing of genomic DNA for all EZH2 coding exons revealed a heterozygous C to G mutation at nucleotide 2045 leading to a non-synonymous mutation of the A677 residue to a glycine (A677G) (FIG. 2A). Sequence analysis of cDNA revealed that both wild-type and mutant alleles are expressed (data not shown). This residue falls within the catalytic SET domain of EZH2 and is located 2 exons downstream of the Y641 residue in exon 18 (FIG. 2B). This residue is highly conserved across multiple species and multiple histone methyltransferases (FIG. 2C) indicating that it may play an essential role in the function of EZH2.

Example 12: Occurrence of the A677G EZH2 Mutation in Primary Lymphoma Samples To establish whether the mutation identified in the Pfeiffer cell line occurs in primary human lymphomas, this residue was sequenced in a panel of 41 lymphoma specimens. This panel consisted of 30 DLBCLs, 6 FL, 1 extra nodal marginal zone B-cell lymphoma of mucosa associated lymphoid tissue (MALT), 1 mantle cell lymphoma (MCL), 1 splenic marginal zone lymphoma (SMZL), and 2 Waldenstrom's macroglobulinemia or lymphoplasmacytic lymphomas (WM) (Table 2). In addition to 4 occurrences of Y641 mutation, non-synonymous missense mutations were observed for P488 and A677. The A677 mutation was heterozygous and occurred in a stage IIE DLBCL obtained from a 74 year old female (FIG. 2A; Table 2). This mutation was expressed as both alleles were detected in cDNA (data not shown). These data demonstrate that the A677G mutation occurs in primary human lymphoma and is not simply an artifact of cell culture.

Figure 3:
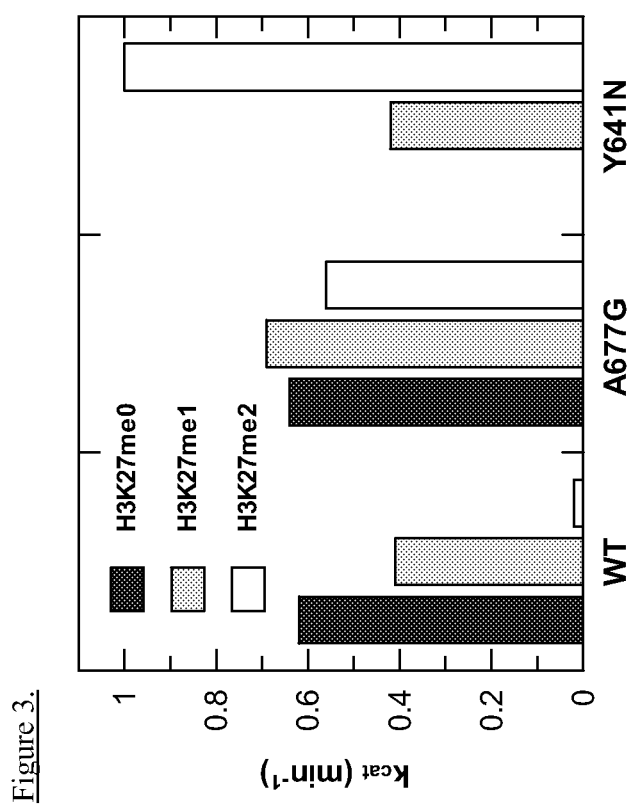
FIG. 3. The A677G EZH2 mutant exhibits activity for all H3K27 methylation states. $k_{cat}$ (min$^{-1}$) for wild type, A677G, and Y641N EZH2 using H3K27me0 (black bars), H3K27me1 (gray bars), or H3K27me2 (white bars) as substrates.

Example 13: The EZH2 A677G Mutation Confers Biochemical Activity Independent of H3K27 Methylation State EZH2 Y641 mutations affect substrate specificity resulting in a preference for H3K27me2 over the unmodified and mono-methylated forms (FIG. 2B) (3, 14). To further investigate the effect of the A677G mutation on substrate preference, we characterized the steady state kinetics of wild-type and mutant EZH2 complexes using peptide substrates containing H3K27me0, H3K27me1, or H3K27me2. When comparing turnover with the three peptide substrates (as either $k_{cat}$ or $k_{cat}/K_m$), wild type EZH2 loses activity when progressively more methyl groups are incorporated into H3K27 (i.e. H3K27me0>H3K27me1>H3K27me2) (FIG. 3, Table 1). In contrast, all Y641 mutant enzymes that were evaluated displayed the opposite trend with the H3K27me2 peptide being utilized most efficiently (i.e. H3K27me2>H3K27me1>H3K27me0) (FIG. 3, Table 1). The A677G EZH2 complex, on the other hand, displayed a profile different from both wild-type and Y641 mutants. A677G EZH2 utilized all three substrates with nearly equal efficiency and at a rate comparable with the best turnover found with the wild type enzyme ($k_{cat}$=0.64 s$^{-1}$ vs 0.62 s$^{-1}$, respectively) (FIG. 3, Table 1). When nucleosomes purified from HeLa cells were evaluated, the activity of A677G EZH2 was higher than wild type EZH2 and the Y641 mutants ($k_{cat}$=0.17 s$^{-1}$ vs 0.10 s$^{-1}$ for wild-type and 0.11 s$^{-1}$ for Y641S). This observation is likely the result of the ability of the A677G EZH2 complex to act upon a greater proportion of the histones which are heterogeneously modified at H3K27.

Example 14: Expression of A677G EZH2 is Sufficient to Drive Hyper-Trimethylation of H3K27

Figure 4:
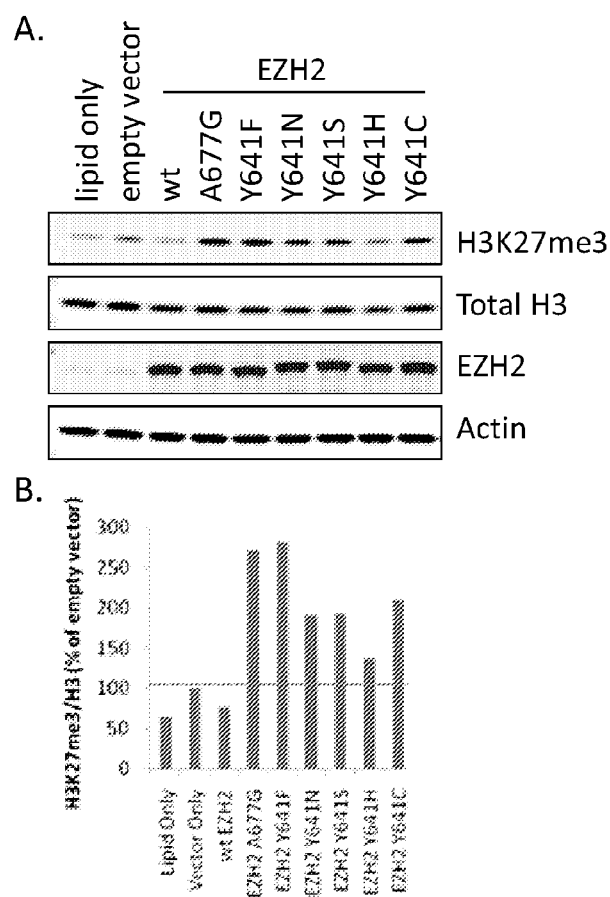
FIG. 4. Exogenous expression of A677G EZH2 stimulates trimethylation of H3K27. MCF-7 breast cancer cells were transiently transfected with expression constructs encoding either wild-type or mutant forms of EZH2. (A.) Western blot analysis of H3K27me3, total H3, and EZH2. Actin serves as a loading control. (B.) H3K27me3 levels normalized to histone H3 as a percentage of cells transfected with the empty vector.

To explore the effect of the A677G and Y641 EZH2 mutants on histone methylation levels, wild-type and mutant versions of EZH2 were transiently expressed in cells prior to evaluation of H3K27me1 and H3K27me3 levels. MCF-7 cells were selected for this analysis as they exhibit relatively low levels of H3K27me3 (26% of Pfeiffer H3K27me3 levels; FIG. 1A) and are easily transfected. Indeed, exogenous expression of either A677G or Y641 mutant EZH2 was capable of inducing a 2-3-fold increase in H3K27me3 bringing the global level of this mark to a level similar to that observed in Pfeiffer cells (FIG. 4). These data demonstrate that expression of the A677G is sufficient to induce a global hyper-trimethylation of the H3K27 residue.

Example 15: Structural Rationale for the Substrate Preference and Product Specificity of A677G Mutant EZH2

Figure 5:
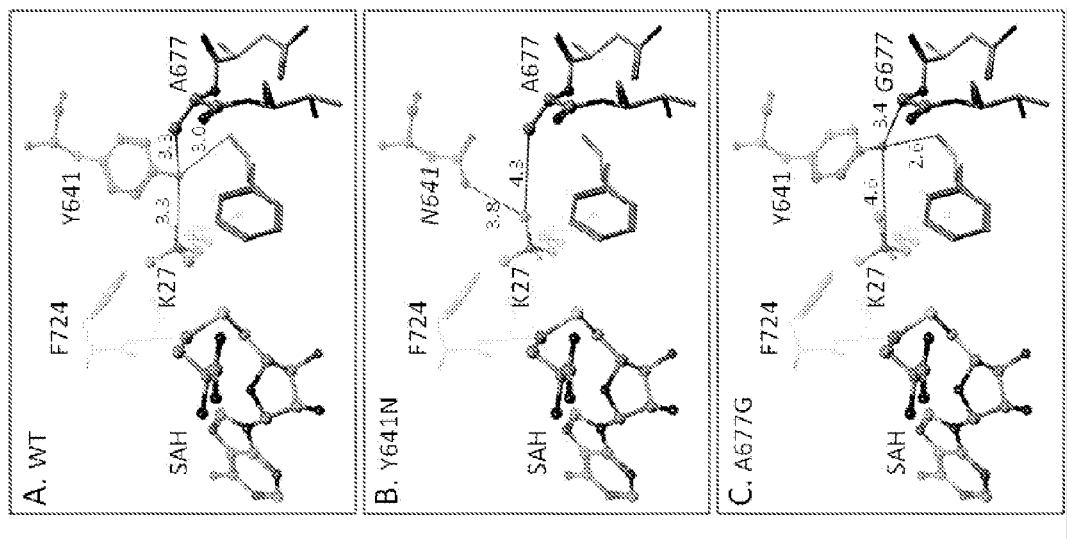
FIG. 5. The A677G EZH2 mutation alters the lysine binding pocket through effects on Y641. A homology model of wild type EZH2 was generated using the crystal structure of GLP/EHMT1 bound to an H3K9me2 peptide substrate. Modeled structure of the active site region in (A) wild-type, (B) Y641N, and (C) A677G EZH2.

In the absence of an EZH2 crystal structure, a homology model was constructed based on the protein sequence of wild-type EZH2 and a crystal structure of GLP/EHMT1 bound to a histone H3 peptide substrate containing H3K9me2 (FIG. 5A). This model is consistent with the biochemical data demonstrating that wild-type EZH2 primarily catalyzes mono- and di-methylation, but not tri-methylation, of H3K27. Similar to other methyltransferases such as Set7/9, the highly conserved EZH2 Y641 residue appears to orient the unmethylated and mono-methylated forms of H3K27 for optimal methyl transfer through hydrogen bonds with the lysine ε-amine group (28, 29). In addition, the presence of a conserved phenylalanine residue (F724) instead of a tyrosine at the Phe/Tyr switch position results in the loss of a hydrogen bond to a structurally conserved water molecule (not depicted in FIG. 5) which has been shown to further orient the un-methylated lysine (28). Since the conserved water lacks the additional hydrogen bond, it is presumably more weakly bound and therefore more easily displaced by the mono-methylated lysine when it rotates into position for the second methyl transfer. Thus, this model supports EZH2 functioning efficiently as a mono- and di-methyltransferase. However, there is very little room for a di-methylated lysine to rotate into position to accept a third methyl group with only 3.3 Å between the hydroxyl oxygen of Y641 and the ε-amine group of H3K27me2. Thus, the Y641 residue of EZH2 has a dual purpose participating in the orientation of unmethylated and mono-methylated lysine while at the same time sterically restricting tri-methylation.

This model predicts that mutation of Y641 to a smaller residue such as asparagine (Y641N) results in both loss of a critical hydrogen bond and generation of a larger lysine tunnel (FIG. 5B). The larger lysine tunnel and loss of proper hydrogen bonding presumably hinder stabilization of an unmodified or mono-methylated lysine which is highly flexible. On the other hand, replacing Y641 with smaller residues, such as asparagine, generates a larger tunnel (H3K27me2 methyl carbon to N641 side chain distance=3.8 Å) which permits rotation of the di-methylated lysine into position for a third methyl transfer. Presumably the two methyl groups of H3Kme2 also make advantageous hydrophobic interactions in the lysine tunnel that help to further orient the di-methylated lysine. This interpretation is consistent with data presented by us and others demonstrating that Y641 mutants do not efficiently utilize an unmethylated lysine, yet have acquired robust activity with di-methylated substrates.

Interestingly, while the structural model for wild-type EZH2 suggests that the highly conserved A677 residue does not interact directly with either SAM or H3K27, it is in close proximity to the hydroxyl oxygen of Y641 (3.3 Å) (FIG. 5A). It is therefore predicted that mutating A677 to a smaller glycine residue permits Y641 to adopt an alternative conformation which generates additional space within the lysine tunnel allowing the di-methylated substrate to rotate into an orientation suitable for methyl transfer (FIG. 5C). This alternative Y641 conformation has sufficient space (3.1 Å) between the hydroxyl oxygen of Y641 and the closest methyl carbon of H3K27me2 even when the lysine tail is rotated into position for a third methyl transfer. Thus, this model suggests that the retention of the Y641 residue combined with the alternative Y641 orientation contributes to the efficient methylation of unmodified, mono-, and di-methylated substrate.

Example 16: Cell Line Sensitivity to EZH2 Inhibitors in Proliferation Assay (Assay 1)

Figure 6:
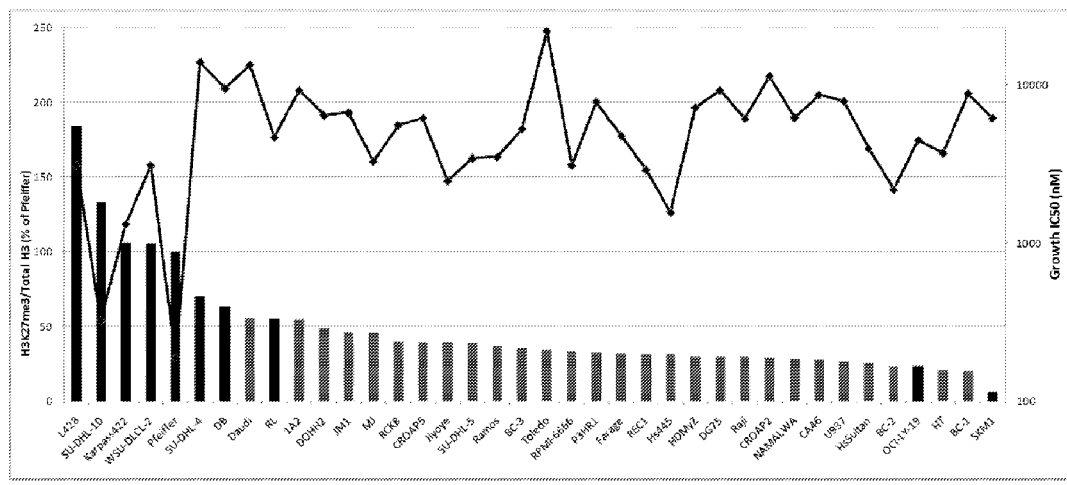
FIG. 6. High levels of H3K27me3 and EZH2 mutation status predict sensitivity to EZH2 inhibition. Lymphoma cell lines were grown in the presence of the EZH2 inhibitor Compound A for 6 days. The concentration of Compound A at which a 50% inhibition in growth occurred is indicated as the growth IC50 and is represented as a line. The H3K27me3 levels are represented as a percentage of the H3K27me3 level obtained with the cell line Pfeiffer (bar graph). Cell lines which have a mutation in EZH2 either at Y641 or A677 are indicated as black bars while those that are wildtype at these positions are indicated as grey bars.

To evaluate the effects of EZH2 mutations and H3K27me3 levels on the sensitivity to EZH2 inhibition, 38 lymphoma cell lines were evaluated in a 6 day proliferation assay (assay 1) using an EZH2 inhibitor indicated as compound A. As shown in Table 5 in FIG. 24 and FIG. 6, cell lines which possess a mutation in EZH2 and have high H3K27me3 (≥100% of Pfeiffer) are sensitive to EZH2 inhibition. EZH2 mutation status alone does not predict sensitivity to EZH2 inhibition under these conditions as there are number cell lines (e.g. SUDL-4, DB, OC1-LY-19 & SKM1) with an EZH2 mutation are resistant or weakly sensitive to EZH2 inhibition. In addition, further optimization of the EZH2 inhibition assay Example 17: Discussion of EZH2 Mutations, Cancer, and Treatment with EZH2 Inhibitors Elevated levels of EZH2 is a hallmark of many cancers and appears to be required for the proliferation of some lymphoma cells as knockdown of EZH2 in the SU-DHL-4 DLBCL cell line results in growth arrest at the G1/S transition (30). Recent studies have identified mutations in EZH2 at Y641 in lymphoma which result in H3K27 hyper-trimethylation (1, 3, 14, 15). Herein, we have reported the identification and characterization of a novel EZH2 mutation capable of increasing global H3K27me3 in human lymphoma cells and demonstrate that lymphoma cell lines with elevated levels of H3K27me3 and harboring either a Y641 or A677 mutation in EZH2 are sensitive to inhibition of EZH2.

While the EZH2 Y641 mutation occurs in 22% of GCB DLBCL and 7% of FL (3), our study indicates that mutation of the EZH2 A677 to glycine is a fairly rare event. We observed this mutation in 1 of 50 lymphoma cell lines and 1 of 41 primary lymphoma samples. In addition, Morin et al recently observed a single case of DLBCL (63 yo female stage 1AE) with the A677G mutation among 127 samples that were assessed by RNA-seq, exome-seq, and/or genome-seq (1). Thus, while a more extensive study with focused genotyping of the A677 codon will be required to establish the true incidence of this alteration, these initial data suggest that the frequency of this mutation is likely below 2-3%.

Considering that the end result (i.e. increased H3K27me3) of these two mutations may be quite similar, it is at first somewhat surprising that these mutations occur at such different rates. However, this discrepancy might be explained in large part by the spectrum of possible activating mutations at each site. To date, mutation of Y641 to any of 5 different residues (F, N, S, C, or H) has been reported to increase activity with an H3K27me2 substrate ((1, 3, 14, 15) and this study). This increased activity has been attributed to the exchange of Y641 for smaller residues which permit the larger H3K27me2 substrate to rotate into a position for methyl transfer. The A677G mutation appears to similarly increase the dimensions of the lysine tunnel through exchange of alanine for a smaller amino acid; however, since alanine is already the second smallest amino acid, it may only be exchanged for a glycine. At the nucleotide level, only 1 of 9 single nucleotide mutations within the A677 codon will achieve a glycine residue, whereas 5 of 9 achieve an activating mutation at Y641. Thus, the apparently low incidence of the EZH2 A677G mutation may simply be due to the extremely limited number of possible alterations for this particular site.

The fact that the SET domain is highly conserved across orthologous and homologous methyltransferases readily permits translation of findings from one methyltransferase to another. For example, the effect of changes at the Y641 residue of EZH2 are predictable based on mutational analyses of other SET domain methyltransferases whose biochemical properties have been more extensively studied. The human SET7/9 methyltransferase normally mono-methylates H3K4, however, when the SET7/9 Y245 residue (the equivalent of EZH2 Y641) is mutated to alanine, the mutant can no longer modify a H3K4me0 substrate, but instead gains the ability to di- and tri-methylate an H3K4me1 peptide substrate (31). An additional study with the H3K9 methyltransferase G9a demonstrated that mutation of Y1067 to phenylalanine converts the enzyme from a mono- and di-methyltransferase to a tri-methyltransferase (32).

Example 18: EZH2 A677 Mutant, e.g. EZH2 A677G is a Novel Biomarker for Use in Therapy To the best of our knowledge, this study is the first report to examine the biochemical and cellular activity of the A677 residue of EZH2 which is conserved across multiple PKMTases. Interestingly, however, the structurally related SET domain containing DIM-5 from N. crassa has a glycine at the equivalent position (FIG. 2C) and has been reported to perform all three methylation events on its H3K9 substrate (33, 34). Thus, it appears that the alanine at residue 677 of EZH2, and likely equivalent residues in other SET domain methyltransferase, plays an important role in the regulation of substrate specificity without being in direct contact with the substrate. This interplay between Y641 and A677 in EZH2 highlights just one of the many important mechanisms that have likely evolved to regulate the substrate and product specificities of lysine methyltransferases.

Example 19: Overview of EZH2 Inhibitor Compound B Treatment in EZH2 Mutants In Vitro and In Vivo In eukaryotes, epigenetic post-translational modification of histones is critical for regulation of chromatin structure and gene expression. EZH2 is the catalytic subunit of the Polycomb Repressive Complex 2 (PRC2) and is responsible for repressing gene expression through methylation of histone H3 on lysine 27 (H3K27). EZH2 over-expression is implicated in tumorigenesis and correlates with poor prognosis in multiple tumor types (21, 36-39). Additionally, somatic heterozygous mutations of Y641 and A677 residues within the catalytic SET domain of EZH2 occur in diffuse large B-cell lymphoma (DLBCL) and follicular lymphoma (FL) (1, 3, 40-42). The Y641 residue is the most frequently mutated residue, with up to 22% of GCB (Germinal Cell B-cell) DLBCL and FL harboring mutations at this site. These lymphomas exhibit increased H3K27 tri-methylation (H3K27me3) due to altered substrate preferences of the mutant enzymes (14, 15, 41, 43). However, it is unknown whether specific, direct inhibition of EZH2 methyltransferase activity will be effective in treating EZH2 mutant lymphomas. Herein, we demonstrate that GSK126, a potent, highly-selective, S-adenosyl-methionine (SAM)-competitive, small molecule inhibitor of EZH2 methyltransferase activity, decreases global H3K27me3 levels and reactivates silenced PRC2 target genes. GSK126 effectively inhibits the proliferation of EZH2 mutant DLBCL cell lines and dramatically inhibits the growth of EZH2 mutant DLBCL xenografts in mice. Together, these data demonstrate that pharmacological inhibition of EZH2 activity may provide a promising treatment for EZH2 mutant lymphoma.

Compound B (GSK126) is an EZH2 inhibitor. Compound B has the formula:

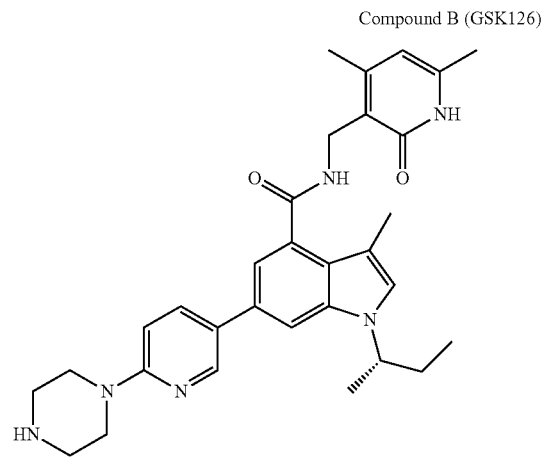 [SMILES: CC[C@H](C)n1cc(C)c2c(C(=O)NCc3c(C)cc(C)[nH]c3=O)cc(-c3ccc(N4CCNCC4)nc3)cc21]

Compound B (GSK126)

Example 20 High Throughput Screen to Identify Compound B (GSK126) as a Potent Inhibitor of EZH2 Methyltransferase Activity To identify inhibitors of EZH2 methyltransferase activity, a high-throughput biochemical screen with a 5-member PRC2 protein complex was performed (44). This work identified a small molecule EZH2 inhibitor with a $K_i^{app}=700$ nM. Extensive optimization of this compound through medicinal chemistry generated GSK126 (FIG. 7A). GSK126 potently inhibits both WT and mutant EZH2 methyltransferase activity with similar potencies ($K_i^{app}=0.5$-3 nM) independent of substrate utilized, and is competitive with SAM and non-competitive with peptide substrates (FIG. 7B, data not shown). GSK126 is highly selective against other methyltransferases and protein classes (Data not shown). In particular, GSK126 is >1,000-fold selective for EZH2 versus 20 other human methyltransferases, including both SET domain and non-SET domain containing methyltransferases (45). Even EZH1, which is 96% identical to EZH2 within the SET domain, and 76% identical overall, is inhibited >150-fold less potently ($K_i^{app}=89$ nM). Utilizing an EZH2 homology model (41), combined with enzyme mechanism-of-action and inhibitor structure-activity relationship data, in silico docking revealed the SAM binding pocket as the most plausible docking site for GSK126. Here it is predicted to make extensive contacts with the post-SET domain which forms one side of the SAM binding pocket (FIG. 8a-d) Interestingly, within 10 Å of the predicted GSK126 binding site 4 of the 6 residue differences between EZH2 and EZH1 lie within the post-SET domain and these may contribute to the loss of potency for EZH1.

Example 21 Compound B (GSK126) Induces Loss of H3K27me3

Figure 7:
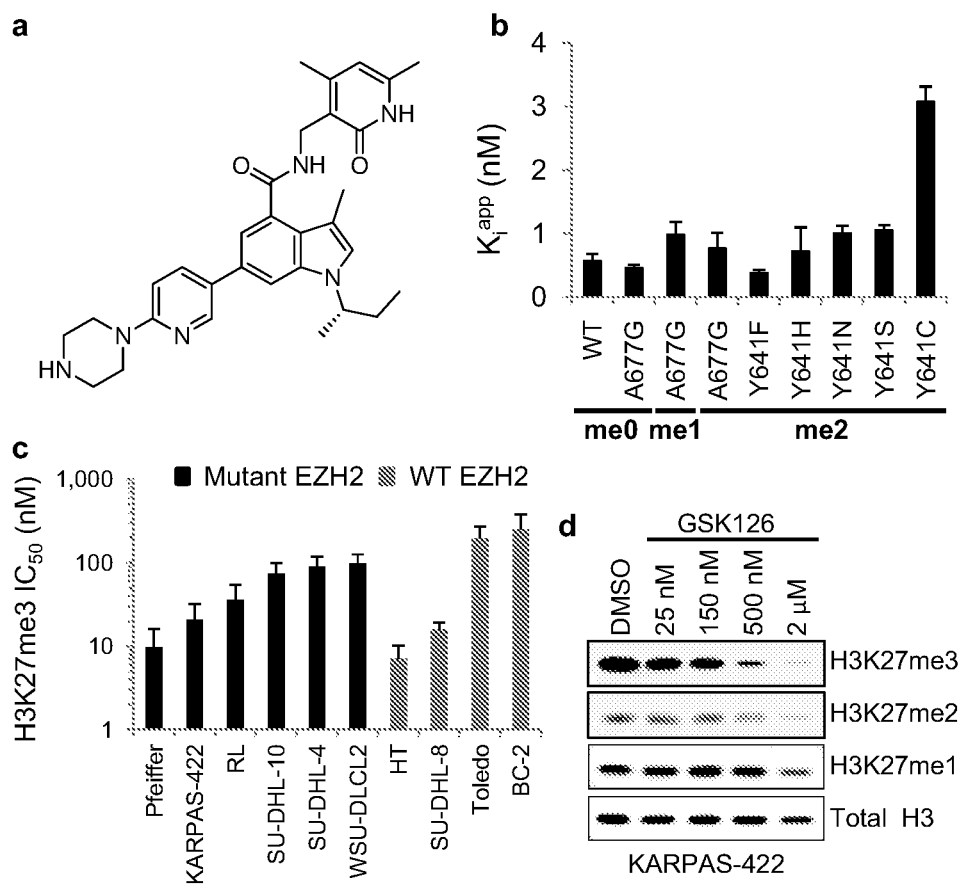
FIG. 7 Biochemical and cellular mechanistic activity of GSK126. (A) Structure of GSK126. (B) Potency of GSK126 against WT and mutant EZH2. Histone H3 peptides (21-44) with K27me0, K27me1 or K27me2 were used as substrates (n=2; mean values±s.d. are shown). (C) Effect of GSK126 on H3K27me3 in lymphoma cell lines treated with GSK126 for 48 hours. $IC_{50}$ values were determined using an H3K27me3 ELISA (n≥2; mean values±s.d. are shown). (D) Evaluation of H3K27me3/2/1 in KARPAS-422 following treatment for 72 hours. Total histone H3 is shown as a loading control.

The altered substrate preferences of EZH2 mutants lead to an imbalance in cellular H3K27 methylation states (FIG. 9a) (14, 41). Nonetheless, GSK126 induced loss of H3K27me3 in both EZH2 WT and mutant DLBCL cell lines with $IC_{50}$ values ranging from 10-252 nM independent of EZH2 mutation status (T-test, p=0.27) (FIG. 7c). Further analyses demonstrated that inhibition of H3K27me3 began before 24 hours and potency was maximal after 2 days (FIG. 9b). GSK126 most potently inhibited H3K27me3, followed by H3K27me2, and H3K27me1 was only weakly reduced at the highest inhibitor concentration (FIG. 7, and FIG. 9c). Total histone H3 and PRC2 components were not affected by GSK126 (FIGS. 9c and 10), thus reduction of H3K27 methylation is due to direct inhibition of EZH2 methyltransferase activity and not degradation of histone H3 or PRC2. This is in contrast to 3-deazaneplanocin A (DZNep), an inhibitor of S-adenosyl-L-homocysteine (SAH) hydrolase that promotes degradation of the PRC2 complex and indirectly inhibits EZH2 through effects on intracellular SAH concentrations (46).

Example 22: Compound B Inhibits Growth of B Cell Lymphoma Cells

We evaluated the effect of Compound B (GSK126) on cell proliferation in a panel of B-cell lymphoma cell lines, using an improved proliferation assay as compared to that used for Compound A (Assay 1 was used for Compound A treatment, above.). Thus, Example 22 and Table 6 in FIG. 25 better reflect the inhibition of HZH2 inhibitors on cell lines, e.g. the lymphoma cell lines. DLBCL cell lines were the most sensitive to EZH2 inhibition (FIG. 11a). Six of the seven most sensitive DLBCL cell lines harbored Y641N, Y641F, or A677G EZH2 mutations (growth $IC_{50}$=28-861 nM) (FIG. 11a, Table 6 in FIG. 25, and FIG. 12). The exception was HT which is WT for EZH2 (growth $IC_{50}$=516 nM). Interestingly, HT harbors a mutation in UTX (R1111C), a H3K27 demethylase frequently inactivated in multiple tumor types (19). Only 2 of the 11 remaining DLBCL cell lines harbored EZH2 mutations suggesting that, in most cases, DLBCL cell lines with mutant EZH2 are dependent on EZH2 activity for cell growth; however, in some situations co-occurring alterations may override the cell's dependence on EZH2 activity making it less sensitive to EZH2 inhibition. Among EZH2 mutant cell lines, sensitivity to GSK126 is independent of BCL2 translocation or p53 mutation, common alterations found within DLBCL (Table 6 in FIG. 25). There was a modest correlation between inhibition of H3K27me3 and cell growth (Pearson, r=0.62), but there was no correlation between sensitivity to GSK126 and EZH2 protein levels (FIG. 13a-c). Interestingly, two of the most sensitive DLBCL cell lines, WSU-DLCL2 and KARPAS-422, are derived from patients with refractory disease (47, 48) suggesting that DLBCL cells that are resistant to standard-of-care may be sensitive to EZH2 inhibition. Burkitt (BL) and Hodgkin's (HL) lymphoma cell lines were generally less sensitive to EZH2 inhibition (growth $IC_{50}$>1.3 μM) with the exception of Jiyoye (growth $IC_{50}$=0.23 M), a BL cell line with WT EZH2. Evaluation of GSK126 in additional lymphoma cell lines and extensive genomic and epigenomic characterization will be required to fully elucidate the determinants of sensitivity among lymphoma subtypes.

Both cytostatic and cytotoxic responses were observed among the most sensitive cell lines (Table 6 in FIG. 25); therefore, the timing of GSK126-induced effects on proliferation and cell death was examined in detail in two of the most sensitive cell lines. In Pfeiffer, potent inhibition of cell proliferation was observed after 2 days (FIG. 11b) and net decreases in cell number were evident after 3 days (FIG. 11c). This cell death appears to be driven by caspase-mediated apoptosis as indicated by the increase in the sub-$G_1$ population (FIG. 11d) and dose-dependent induction of caspase activity (FIG. 11e). The response in KARPAS-422 was slower with 6-7 days required for maximal potency (FIG. 11b). Furthermore, a primarily cytostatic effect was observed in KARPAS-422 as demonstrated by CTG values remaining above day 0 levels, a $G_1$ arrest (43% and 77% of cells in $G_1$ with DMSO and 500 nM GSK126, respectively) with little sub-$G_1$ content, and minimal caspase activity with <1 μM GSK126 (FIG. 11f-h). Consistent with these observations, shRNA-mediated knockdown of EZH2 led to profound cytotoxic and apoptotic responses in Pfeiffer, and decreased cell proliferation, and no caspase activation in KARPAS-422 demonstrating that the phenotypic effects observed with GSK126 are due to inhibition of EZH2 (FIG. 14a-c).

Example 23 the Effect of Compound B on Gene Expression

Since EZH2 is associated with transcriptional repression, we evaluated the effect of GSK126 on gene expression in DLBCL cell lines with a range of sensitivity to GSK126. Robust transcriptional activation was noted in the most sensitive cell lines (FIG. 15a, FIG. 16a, and data not shown). Not surprising, considering the repressive nature of H3K27me2/3, the majority of transcriptional changes involved up-regulation. The high degree of similarity between gene expression changes observed with GSK126 treatment and EZH2 knockdown in KARPAS-422 and Pfeiffer cells suggests that these transcriptional changes are due to loss of EZH2 activity and not off-target effects (data not shown Additionally, analysis of ChIP-seq data for the 3 most responsive cell lines revealed that prior to treatment up-regulated genes exhibited broad enrichment of H3K27me3 suggesting these genes are EZH2 targets marked by H3K27me3 (FIG. 15b and FIG. 17a-c).

In contrast to the response observed in the sensitive cell lines, minimal transcriptional changes occurred with GSK126 treatment in Toledo, a cell line with WT EZH2 whose growth is not affected by EZH2 inhibition (FIG. 15a, FIG. 16b). Even at 2 μM GSK126, very few transcriptional changes were observed in Toledo (23 up-regulated and 10 down-regulated probe sets), despite a near complete loss of H3K27me3 at this dose and time (FIG. 9c and data not shown). Likewise, qRT-PCR performed for two H3K27me3-enriched genes revealed dose-responsive increases in gene expression with as little as 25 nM GSK126 in Pfeiffer and KARPAS-422, but no transcriptional changes in Toledo with up to 1 μM GSK126 (FIG. 15c, data not shown). Interestingly, even in the most sensitive WT EZH2 cell line, HT, the transcriptional response was less pronounced when compared to EZH2 mutant DLBCL cell lines with similar sensitivity (FIG. 15a). Relaxing the transcriptional fold-change criteria from 2.0 to 1.5 revealed additional modest transcriptional changes in HT cells (FIG. 16b). This muted transcriptional response in EZH2 WT and less sensitive mutant cell lines suggests that other compensatory mechanisms (such as H3K9, H4K20, or DNA methylation) may exist in these cell lines to dampen the transcriptional response.

Figure 26:
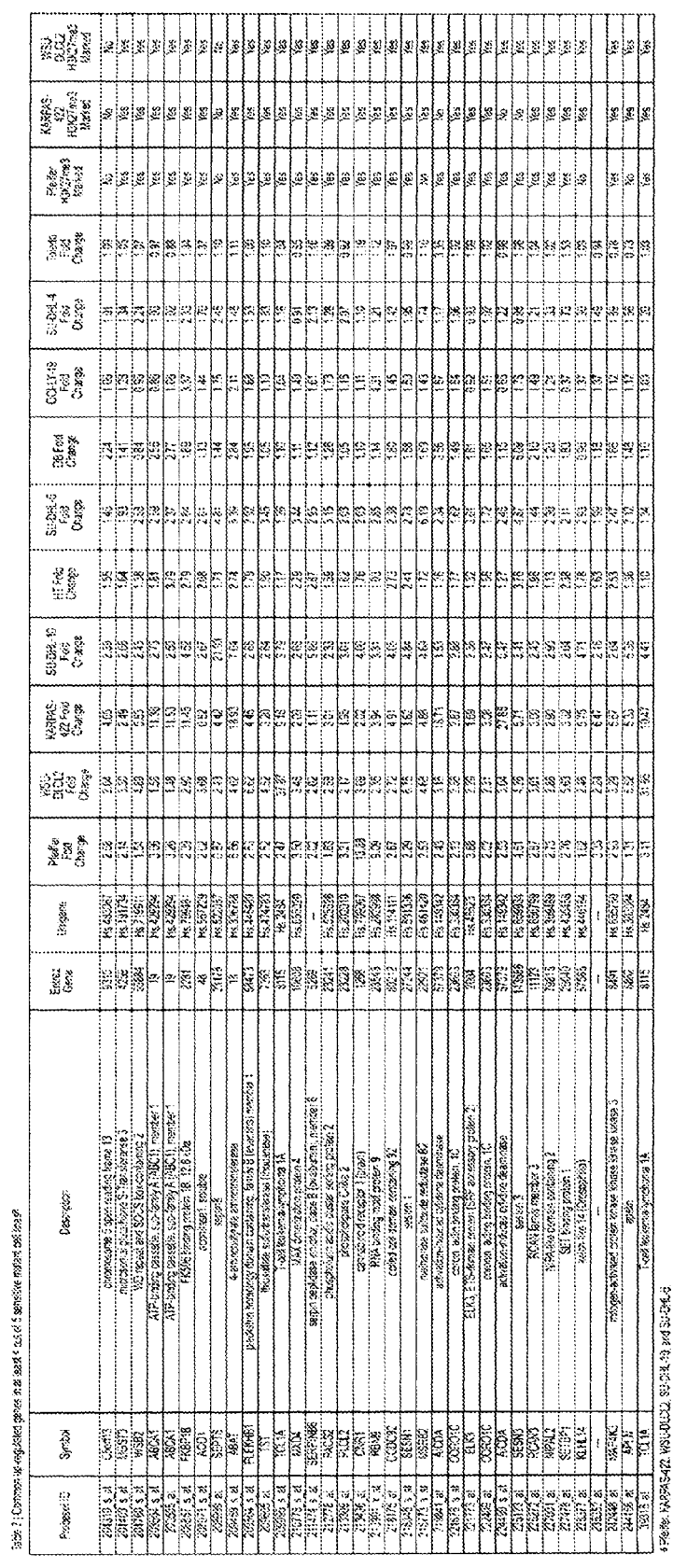

Among the EZH2 mutant cell lines, global H3K27me3 levels were statistically higher in transcriptionally-responsive lines (T-test, p=0.019) suggesting that EZH2 mutation status together with global H3K27me3 levels may be a better predictive biomarker than mutation status alone (FIG. 16c). While the five most sensitive EZH2 mutant cell lines exhibited a preponderance of up-regulated gene expression changes (69-95%), little overlap was observed among the differentially-regulated probe sets using 2-fold or 1.5-fold significance criteria (FIG. 15d and FIG. 16d). Only 35 up-regulated probe sets were common to at least 4 of these 5 mutant cell lines (Table 7 in FIG. 26). Examination of these commonly up-regulated probe sets revealed that many are enriched for H3K27me3 (32/35) (Table 7 in FIG. 26 and data not shown). Additionally, many of these probe sets are induced, albeit weakly, in the other cell lines suggesting that additional time or chromatin factors may be required for complete gene activation in these settings (FIG. 15e and Table 7 in FIG. 26). Lastly, while no single pathway or process was significantly enriched among the limited set of genes commonly up-regulated, gene ontology enrichment analysis of regulated gene sets in each cell line individually revealed several common processes including cell cycle regulation, cell death, and regulation of biological/cellular processes (FIG. 18 and data not shown). These data demonstrate that the global loss of H3K27me3 following inhibition of EZH2 with GSK126 is associated with transcriptional activation of EZH2 target genes that correlates well with sensitivity and that mutant EZH2 de-regulates H3K27me3 in a global, rather than targeted, manner. The significant variation between the up-regulated gene sets of sensitive cell lines is a surprising observation that likely highlights the complexity and uniqueness of the epigenome in each cell line, and the diversity of selective pressures during the development of individual lymphomas.

Example 24 Compound B Inhibits Tumor Growth In Vivo

Based upon the potent effects in cell culture, we evaluated GSK126 in mice using subcutaneous xenografts of KARPAS-422 and Pfeiffer. Following 10 days of once-daily (QD) dosing of GSK126, global H3K27me3 decreased and gene expression increased in a dose-dependent fashion consistent with observations from cell culture (FIG. 19a,b). Although GSK126 was initially cleared rapidly from the blood, there was an extended terminal phase where drug elimination from blood and tumor was slower (FIG. 20a,b). With daily 50 mg/kg dosing, complete tumor growth inhibition was observed in both KARPAS-422 and Pfeiffer models (FIG. 19c, and FIG. 21a). When higher dosing regimens were examined with KARPAS-422 xenografts, marked tumor regression was observed (FIG. 19c). Upon cessation of dosing, tumors in the 50 mg/kg QD group exhibited tumor stasis while complete tumor eradication was observed in the 150 mg/kg QD and 300 mg/kg twice/week groups. Tumor growth inhibition also correlated with statistically significant increased survival of mice bearing the more aggressive KARPAS-422 tumors, where spontaneous deaths occurred in vehicle-treated animals (FIG. 19d). Based upon these striking observations, intermittent dosing regimens with lower doses of GSK126 given weekly or with a 1 week drug holiday were examined in KARPAS-422 tumor xenografts with large tumors (FIG. 21b). All schedules demonstrated tumor growth inhibition (91-100%, T-test, p values=0.0008 to 0.0024). These results indicate that the response to GSK126 is durable and that intermittent dosing schedules may be effective in a clinical setting even in advanced tumors.

GSK126 was well tolerated at the doses and schedules examined as measured by little to no decrease in body weight, normal grooming and behavior, and vastly improved survival in mice carrying KARPAS-422 xenografts (FIG. 22a-c and FIG. 19d). Given the role of EZH2 in normal hematopoiesis and the identification of EZH2 loss-of-function mutations in myeloid malignancies (49-52), we investigated the effects of GSK126 treatment on peripheral blood of immunocompetent mice. Complete blood count analysis revealed no significant changes in any blood cell types at doses and times where efficacy was observed in tumor xenografts (FIG. 22d).

Over the past decade, the development of targeted agents that specifically inhibit oncoproteins with activating somatic alterations has provided profound clinical benefit for cancer patients (53, 54). The data herein provide compelling evidence that inhibition of EZH2 methyltransferase activity may be a viable strategy for the treatment of DLBCL and non-indolent FL harboring activating mutations in EZH2. GSK126 also provides a means to evaluate whether EZH2 activity is required for the survival of tumors where EZH2 over-expression has been linked to poor prognosis (36-39), and tumors harboring loss-of-function mutations in UTX (19, 50, 55). While we do not expect GSK126 to be effective in treating myeloid malignancies bearing loss-of-function mutations in EZH2 (50-52), GSK126 should be an important tool to assess the role of EZH2 in normal myeloid development and to understand the oncogenic role of EZH2 in myeloproliferative neoplasms. Lastly, the identification of a selective EZH2 inhibitor which does not lead to degradation of the PRC2 complex provides a useful tool to understand the role of EZH2 methyltransferase activity versus its scaffolding role in development, tumorigenesis, and tumor progression that could not be elucidated through conventional genetic manipulation studies.

Example 25: Methods Summary for Examples Disclosing GSK126 (Compound B)

Biochemical assays utilized the 5-member PRC2 complex (human Flag-EZH2, EED, SUZ12, AEBP2, RbAp48) containing either WT or mutant EZH2, [$^3$H-]SAM and the indicated peptide substrate; reactions were incubated for 30 minutes. Global histone modification levels were determined by ELISA or western blot methods using antibodies specific for total histone H3, H3K27me1, H3K27me2, or H3K27me3. Cell proliferation and Caspase-3/7 activity were assessed using CellTiter-Glo and Caspase-Glo 3/7 (Promega), respectively. Gene expression profiling was conducted using Affymetrix Human Genome U133 Plus 2.0 microarrays. Differentially-expressed probe sets were determined by fitting the data to a linear model using the limma statistical package (http://www.bioconductor.org) and carrying out pair-wise contrasts of treated versus control. Significant probe sets were filtered for detection (log 2 signal threshold of 8), an average fold-change>2 or <−2, or >1.5 or <−1.5, where indicated, with p-values adjusted for multiple testing correction by FDR (Benjamini Hochberg)<0.1. H3K27me3 ChIP reads were aligned using Bowtie (56). H3K27me3 enrichment peaks were identified using SICER (57) with optimized parameters. A custom PERL script was utilized to quantify the average basal H3K27me3 ChIP-seq tag density across gene sets. All in vivo studies were conducted after review by the Institutional Animal Care and Use Committee at GSK and in accordance with the GSK Policy on the Care, Welfare and Treatment of Laboratory Animals. GSK126 and vehicle were administered to mice intraperitoneally. Two-tailed t-tests were conducted assuming two samples of equal variance.

Determination of $K_i^{App}$ Values for GSK126 Inhibition of WT and Mutant EZH2.

The 5 member PRC2 complex (Flag-EZH2, EED, SUZ12, AEBP2, RbAp48) containing either WT or mutant (A677G, Y641N, Y641C, Y641H, Y641S, or Y641F) EZH2 was prepared as previously described (41). GSK126 was dissolved in DMSO and tested at concentrations of 0.6 nM to 300 nM with a final DMSO concentration of 2.5%. In contrast to wild-type EZH2 which prefers H3K27me0 as a substrate in vitro, EZH2 Y641 mutants prefer H3K27me2 and have little activity with H3K27me0 or H3K27me1. The A677G mutant is distinct from both the wild-type and Y641 mutant forms of EZH2 in that it efficiently methylates H3K27me0, H3K27me1, and H3K27me2; therefore, histone H3 peptides (residues 21-44; 10 µM final) with either K27me0 (WT, A677G EZH2), K27me1 (A677G EZH2), or K27me2 (A677G, Y641N, Y641C, Y641H, Y641S, and Y641F EZH2) were used as methyltransferase substrates. GSK126 was added to plates followed by addition of 6 nM EZH2 complex and peptide. As the potency of GSK126 is at or near the tight binding limit of an assay run at [SAM]=$K_m$, we used a method where $IC_{50}$ values were measured at a high concentration of the competitive substrate SAM relative to its $K_m$ (7.5 µM SAM where the SAM $K_m$ is 0.3 µM). Under these conditions, the contribution from the enzyme concentration becomes relatively small (see EQ 1) and accurate estimates of $K_i$ can be calculated (58). Reactions were initiated with [$^3$H-]SAM, incubated for 30 minutes, quenched with the addition of 500-fold excess unlabeled SAM, and the methylated product peptide was captured on phosphocellulose filters according to the vendor supplied protocol for MSPH Multiscreen plates (EMD Millipore, Billerica, Mass., USA). Plates were read on a TopCount after adding 20 µL of Microscint-20 cocktail (both from PerkinElmer, Waltham, Mass. USA). Apparent $K_i$ values+/−s.d. were calculated using the Cheng-Prusoff relationship (59) for a competitive inhibitor (n=2).

$$IC_{50}=K_i*(1+[S]/K_m)+[E]/2. \quad \text{EQ1:}$$

Mechanism of GSK126 Inhibition of EZH2.

$IC_{50}$ values were determined for GSK126 inhibition of EZH2 at several SAM concentrations ranging from 0.1 µM to 15 µM and then separately at several peptide concentrations ranging from 16 µM to 60 µM using the assay conditions described above. The resulting $IC_{50}$ values were plotted against the [SAM]/$K_m$ ratio or the [peptide]/$K_m$ ratio respectively.

Cell Culture and Immunoblotting.

Cell lines were obtained from the American Type Culture Collection or the Deutsche Sammlung von Mikroorganismen und Zellbulturen and maintained in the recommended cell culture media at 37° C. in 5% $CO_2$. Cells were lysed with radioimmunoprecipitation (RIPA) buffer (ThermoScientific) and western blot analysis was conducted as previously described (41). Antibodies were obtained as previously described (41) or from Cell Signaling Technology (SUZ12, 3737), or Santa Cruz Biotechnology (EED, sc-28701).

H3K27 Methylation Status and PRC2 Components Following GSK26 Treatment.

Cells (2×10$^5$/well) were seeded into six-well tissue culture plates in the appropriate cell culture media 24 hours before treatment. Cells were then exposed to 0.1% DMSO or varying concentrations of GSK126 (range=25 nM-2 µM) for 24, 72, or 144 hours.

ELISA-Based Quantitation of Total Histone H3 and H3K27me3 Levels.

Following tissue homogenization, tumor tissue lysates were prepared using the Epigentek Histone Extraction kit (OP-0006). Alternatively, cells were seeded at 2,000 cells/well in a 96-well plate and were treated with a 10-point 3-fold dilution series of GSK126 (dose range=2 nM-38 µM) for 48 hours. Cells were lysed with 0.2N HCl for 30 minutes to extract histones, the acid-insoluble portion was pelleted by centrifugation, and the supernatant was neutralized with neutralization buffer (1M $Na_2HPO_4$, pH 12.5; ActiveMotif) containing protease inhibitors (Roche). Lysates were added to Maxisorp ELISA plates (Nunc) in duplicate on each of two plates plus blocking buffer (1% BSA). Plates were incubated for 1 hour, washed 4 times with imidazole buffered saline containing Tween-20 (Kirkegaard & Perry Laboratories), incubated with primary antibodies for H3K27me3 or total H3, washed, incubated with HRP-linked secondary anti-rabbit IgG antibody, and washed again. Luminata Forte substrate (Millipore) was added 5 minutes before chemiluminescence was quantified with an EnVision multi-label plate reader (PerkinElmer). H3K27me3 levels were normalized to total H3 values and $IC_{50}$ values were determined using a 4-parameter curve fit.

Cell Proliferation Assay.

The optimal cell seeding was determined empirically for all cell lines by examining the growth of a wide range of seeding densities in a 384-well format to identify conditions that permitted proliferation for 6 days. Cells were then plated at the optimal seeding density 24 hours prior to treatment (in duplicate) with a 20-point 2-fold dilution series of GSK126 or 0.15% DMSO. Plates were incubated for 6 days at 37° C. in 5% $CO_2$. Cells were then lysed with CellTiter-Glo (Promega) and chemiluminescent signal was detected with a TECAN Safire2 microplate reader. In addition, an untreated plate of cells was harvested at the time of compound addition ($T_0$) to quantify the starting number of cells. CTG values obtained after the 6 day treatment were expressed as a percent of the $T_0$ value and plotted against compound concentration. Data were fit with a 4-parameter equation to generate a concentration response curve and the concentration of GSK126 required to inhibit 50% of growth ($gIC_{50}$) was determined.

Caspase 3/7 Assay.

For detection of caspase-3/7 activity, cells were cultured in 96-well plates, treated with a 10-point 3-fold dilution series of GSK126 (range 0.03 nM to 5 µM) and evaluated using Caspase-Glo 3/7 (Promega) as per the manufacturer's instructions. Values were normalized to CellTiter Glo (Promega) levels at each time point and expressed as a percentage of vehicle treated control. Data represent an average of n=4.

Cell Cycle Analysis.

Cell cycle phase distribution was examined by flow cytometry. Twenty-four hours after seeding cells in a 6-well culture plate, cells were treated with GSK126 or 0.1% DMSO (vehicle) for 3 days. Cells were washed with PBS, pelleted in BD buffer solution, flash frozen, and stored at −80° C. CycleTest™ PLUS DNA reagent kit (Becton Dickinson, 340242) was used according to the manufacturer's instructions to prepare and stain nuclei with propidium iodide. Samples were evaluated using a FACSCalibur flow cytometer (Becton Dickinson) and data were analyzed using FlowJo software (Tree Star).

Gene Expression Profiling.

Cells ($2\times10^5$/well) were seeded into six-well tissue culture plates in the appropriate cell culture media 24 hours before treatment. Duplicate wells were then exposed to 0.1% DMSO, 500 nM, or 2 µM GSK126 for 72 hours. Cells were collected into Trizol reagent (Invitrogen) and total RNA was isolated via phenol:chloroform extraction and the RNeasy kit (Qiagen) according to the manufacturer's instructions. Total RNA was labeled and hybridized to Affymetrix Human Genome U133 Plus 2.0 oligonucleotide microarrays arrays according to the manufacturer's instructions (Affymetrix, Santa Clara, Calif., USA) at Expression Analysis (Durham, N.C.). These data are accessible through GEO via accession number GSE40972. Principal component and correlation analysis were used to confirm data reproducibility (FIG. 16).

Affymetrix Gene Chip Data Analysis.

CEL files, corresponding to individual samples, were processed by the Micro Array Suite 5.0 (MAS5) algorithm (http://www.affymetrix.com/support/index.affx) where signal values were scaled to a target intensity of 500 and log 2 transformed. Differentially expressed probe sets were determined by fitting the data to a linear model and carrying out pair-wise contrasts of treated versus control. Significant probe sets were filtered for detection (log 2 signal threshold of 8), an average fold-change>2 or <-2, or >1.5 or <-1.5, where indicated, with p-values adjusted for multiple testing correction by FDR (Benjamini Hochberg)<0.1. Statistical analyses were performed using the limma package from Bioconductor (http://www.bioconductor.org/). Functional analyses of differentially expressed probe sets were performed using DAVID (http://david.abcc.ncifcrf.gov/). Significantly over-represented GO Biological Process (BP) and Molecular Function (MF) terms (levels 3-5) were filtered for EASE p-value<0.01.

qRT-PCR.

Cells were treated for 72 hours with 0.1% DMSO or a range of concentrations of GSK126 (range=25 nM-1 µM) and total RNA was isolated as described above. RNA (2.8 µg) was reverse transcribed with MultiScribe Reverse Transcriptase (Applied BioSystems) according to the manufacturer's recommendations. The resulting cDNA was diluted and used along with TaqMan gene expression assays (Applied Biosystems; GAPDH, Hs03929097_g1; TNFRSF21, Hs00205419_m1; TXNIP, Hs00197750_m1). TaqMan Gene Expression Master Mix (Applied BioSystems), and a ViiA 7 Real-Time PCR System (Applied BioSystems) according to the manufacturer's recommendations to quantify gene expression.

ChIP-Seq.

Cells ($5\times10^7$) were maintained in the appropriate cell culture media for 24 hours prior to fixation. Cells were fixed for 15 minutes at room temperature with freshly prepared formaldehyde solution (final concentrations 1% formaldehyde, 10 mM NaCl, 0.1 mM EDTA pH 8.0, 5 mM HEPES pH 7.9) followed by the addition of glycine to 125 mM. Fixed cells were rinsed twice in PBS containing 0.5% Igepal CA-630 (Sigma) and cell pellets were flash frozen. ChIP assays were performed using a custom assay protocol at ActiveMotif Inc. (San Diego, Calif.). H3K27me3 ChIP and input libraries were prepared for 35 nucleotide single-end sequencing on an Illumina GAIIx sequencer according to manufacturer's instructions. These data are accessible through GEO via accession number GSE40970. Reads were assessed for quality (base quality<20 were excluded) and aligned to human reference sequence (hg19 build) using the Bowtie[27] algorithm allowing for up to 2 mismatches. Only uniquely mapped reads were utilized for subsequent analyses.

ChIP-seq Analysis.

The average basal H3K27me3 ChIP-seq tag count was quantified across genes that were up-regulated, down-regulated, or unchanged following treatment with GSK126 using a custom PERL script. In addition to the gene body, a region encompassing 10 kb upstream of the transcription initiation site and 10 kb downstream of the transcription termination site were evaluated. All genes were oriented by strand, and the variable length of gene bodies were standardized to 10,000 bins. After averaging the numbers of sequence tags at each base pair the values were normalized to the total number of mapped sequence tags per ChIP. A 500 base pair centered moving average was then applied to highlight larger trends and smooth out short-range fluctuations. MultiExperiment Viewer (http://www.tm4.org/mev/) was used to evaluate enrichment across individual genes. Peaks of H3K27me3 enrichment were identified using the peak calling software SICER[28] with the following parameters: fragment size: 250 bp; effective genome size fraction: 0.86; window size: 750 bp; gap size: 3; redundancy threshold: 1; FDR: 0.001. Statistically significant peaks (FDR<0.001) enriched in the ChIP sample relative to its corresponding input sample were annotated for genomic location and were assigned to genes within +/-10 kb from transcription start site (TSS) to identify target genes: upstream (-10 to 2.5 kb relative to TSS); promoter (-2.5 kb to +2.5 kb); 5'UTR; coding region; 3'UTR. All genes were considered in the 5'→3' orientation. Bedtools was used for manipulation and analysis of data and IGV http://www.broadinstitute.org/igv was used for visualization. Annotation files were downloaded from UCSC. Functional analyses of differentially expressed probe sets were performed using DAVID (http://david.abcc.ncifcrf.gov).

RNA Isolation from Tumor Xenografts.

Qiazol (300 µl/mg tumor) (Qiagen) was added to tumor xenograft tissue. The tumor was lysed and homogenized using the Qiagen TissueLyzer and stainless steel beads. Chloroform was added to the Qiazol lysate. The Qiazol/chloroform homogenate was then added to a Qiagen MaXtract High Density tube (Qiagen). The aqueous phase was transferred to a fresh tube and mixed with an equal volume of 70% EtOH and applied to a Qiagen RNeasy column (Qiagen). The remaining RNA isolation was carried out according to the manufacturer's protocol.

In Vivo Studies.

All studies were conducted after review by the Institutional Animal Care and Use Committee at GSK and in accordance with the GSK Policy on the Care, Welfare and Treatment of Laboratory Animals. For all in vivo studies, GSK126 or vehicle was administered intraperitoneally at a dose volume of 0.2 mL/20 g body weight in 20% captisol adjusted to pH 4-4.5 with 1 N acetic acid. Pfeiffer or KARPAS-422 cells ($1\times10^7$) in 100% matrigel (BD Biosciences) were implanted subcutaneously in female beige SCID mice. Tumors were measured with calipers, block randomized according to tumor size into treatment groups. For efficacy studies, 10 mice were randomized in each treatment group prior to the initiation of dosing and GSK126 treatment was initiated once the tumor volumes were approximately 200 mm$^3$ in the Pfeiffer and KARPAS-422 studies (FIG. 10c and FIG. 21a) and 500 mm$^3$ in the KARPAS-422 intermittent dosing study (FIG. 21b). Mice were weighed and tumors measured with calipers twice weekly. For mouse pharmacokinetic studies, tumor and blood samples were harvested from euthanized mice at the indicated time. Blood and tumor homogenates were flash frozen and subsequently analyzed by HPLC/MS/MS to evaluate the concentration of GSK126. For pharmacodynamic studies, a portion of each tumor was frozen for H3K27me3/H3 ELISAs or placed in RNAlater (Ambion) for RNA isolation. For peripheral blood analyses, blood was harvested via cardiac puncture from euthanized, immunocompetent CD-1 mice (3 mice/group) on day 18. Blood was immediately placed into a Microtainer EDTA tube (BD) and gently mixed by inverting. A complete blood count analysis was conducted using the Advia 2120 hematology analyzer (Siemens Medical Solutions) using multi-species software as per manufacturer's instructions.

REFERENCES

The reference list is cited throughout the text. Each of the references is hereby incorporated by reference in its entirety herein, e.g. to provide additional experimental details. To the extent that the references conflict with the claims, embodiments, or definitions described herein, the instant specification controls.

1. Morin R D, Mendez-Lago M, Mungall A J, et al. Frequent mutation of histone-modifying genes in non-Hodgkin lymphoma. Nature. 476, 298-303 (2011)
2. Bodor C, O'Riain C, Wrench D, et al. EZH2 Y641 mutations in follicular lymphoma. Leukemia; 25:726-9.
3. Morin R D, Johnson N A, Severson T M, et al. Somatic mutations altering EZH2 (Tyr641) in follicular and diffuse large B-cell lymphomas of germinal-center origin. Nat Genet; 42:181-5.
4. Gui Y, Guo G, Huang Y, et al. Frequent mutations of chromatin remodeling genes in transitional cell carcinoma of the bladder. Nat Genet.
5. Fathi A T, Abdel-Wahab O. Mutations in epigenetic modifiers in myeloid malignancies and the prospect of novel epigenetic-targeted therapy. Adv Hematol; 2012: 469592.
6. Stransky N, Egloff A M, Tward A D, et al. The mutational landscape of head and neck squamous cell carcinoma. Science; 333:1157-60.
7. Kuzmichev A, Nishioka K, Erdjument-Bromage H, Tempst P, Reinberg D. Histone methyltransferase activity associated with a human multiprotein complex containing the Enhancer of Zeste protein. Genes Dev 2002; 16:2893-905.
8. Muller J, Hart C M, Francis N J, et al. Histone methyltransferase activity of a *Drosophila* Polycomb group repressor complex. Cell 2002; 111:197-208.
9. Cao R, Wang L, Wang H, et al. Role of histone H3 lysine 27 methylation in Polycomb-group silencing. Science 2002; 298:1039-43.
10. Su I H, Basavaraj A, Krutchinsky A N, et al. Ezh2 controls B cell development through histone H3 methylation and Igh rearrangement. Nat Immunol 2003; 4:124-31.
11. Kamminga L M, Bystrvkh L V, de Boer A, et al. The Polycomb group gene Ezh2 prevents hematopoietic stem cell exhaustion. Blood 2006; 107:2170-9.
12. Majewski I J, Ritchie M E, Phipson B, et al. Opposing roles of polycomb repressive complexes in hematopoietic stem and progenitor cells. Blood; 116:731-9.
13. Simon J A, Lange C A. Roles of the EZH2 histone methyltransferase in cancer epigenetics. Mutat Res 2008; 647:21-9.
14. Sneeringer C J, Scott M P, Kuntz K W, et al. Coordinated activities of wild-type plus mutant EZH2 drive tumor-associated hypertrimethylation of lysine 27 on histone H3 (H3K27) in human B-cell lymphomas. Proc Natl Acad Sci USA; 107:20980-5.
15. Yap D B, Chu J, Berg T, et al. Somatic mutations at EZH2 Y641 act dominantly through a mechanism of selectively altered PRC2 catalytic activity, to increase H3K27 trimethylation. Blood 117:2451-9.
16. Rogenhofer S, Kahl P, Mertens C, et al. Global histone H3 lysine 27 (H3K27) methylation levels and their prognostic relevance in renal cell carcinoma. BJU Int.
17. Chen C, Zhao M, Yin N, et al. Abnormal Histone Acetylation and Methylation Levels in Esophageal Squamous Cell Carcinomas. Cancer Invest.
18. Dalgliesh G L, Furge K, Greenman C, et al. Systematic sequencing of renal carcinoma reveals inactivation of histone modifying genes. Nature; 463:360-3.
19. van Haaften G, Dalgliesh G L, Davies H, et al. Somatic mutations of the histone H3K27 demethylase gene UTX in human cancer. Nat Genet 2009; 41:521-3.
20. Friedman J M, Liang G, Liu C C, et al. The putative tumor suppressor microRNA-101 modulates the cancer epigenome by repressing the polycomb group protein EZH2. Cancer Res 2009; 69:2623-9.
21. Varambally S, Cao Q, Mani R S, et al. Genomic loss of microRNA-101 leads to overexpression of histone methyltransferase EZH2 in cancer. Science 2008; 322:1695-9.
22. Bracken A P, Pasini D, Capra M, Prosperini E, Colli E, Helin K. EZH2 is downstream of the pRB-E2F pathway, essential for proliferation and amplified in cancer. EMBO J 2003; 22:5323-35.
23. Saramaki O R, Tammela T L, Martikainen P M, Vessella R L, Visakorpi T. The gene for polycomb group protein enhancer of zeste homolog 2 (EZH2) is amplified in late-stage prostate cancer. Genes Chromosomes Cancer 2006; 45:639-45.
24. Makishima H, Jankowska A M, Tiu R V, et al. Novel homo- and hemizygous mutations in EZH2 in myeloid malignancies. Leukemia; 24: 1799-804.
25. Nikoloski G, Langemeijer S M, Kuiper R P, et al. Somatic mutations of the histone methyltransferase gene EZH2 in myelodysplastic syndromes. Nat Genet; 42:665-7.
26. Ernst T, Chase A J, Score J, et al. Inactivating mutations of the histone methyltransferase gene EZH2 in myeloid disorders. Nat Genet; 42:722-6.
27. Gabay C, Ben-Bassat H, Schlesinger M, Laskov R. Somatic mutations and intraclonal variations in the rearranged Vkappa genes of B-non-Hodgkin's lymphoma cell lines. Eur J Haematol 1999; 63:180-91.
28. Del Rizzo P A, Couture J F, Dirk L M, et al. SET7/9 catalytic mutants reveal the role of active site water molecules in lysine multiple methylation. J Biol Chem; 285:31849-58.
29. Couture J F, Dirk L M, Brunzelle J S, Houtz R L, Trievel R C. Structural origins for the product specificity of SET domain protein methyltransferases. Proc Natl Acad Sci USA 2008; 105:20659-64.
30. Velichutina I, Shaknovich R, Geng H, et al. EZH2-mediated epigenetic silencing in germinal center B cells contributes to proliferation and lymphomagenesis. Blood; 116:5247-55.
31. Xiao B, Jing C, Wilson J R, et al. Structure and catalytic mechanism of the human histone methyltransferase SET7/9. Nature 2003; 421:652-6.

32. Wu H, Min J, Lunin V V, et al. Structural biology of human H3K9 methyltransferases. PLoS One; 5:e8570.
33. Zhang X, Yang Z, Khan S I, et al. Structural basis for the product specificity of histone lysine methyltransferases. Mol Cell 2003.12:177-85.
34. Tamaru H, Zhang X, McMillen D, et al. Trimethylated lysine 9 of histone H3 is a mark for DNA methylation in *Neurospora crassa*. Nat Genet 2003; 34:75-9.
35. Jiang Y, Schneck J L, Grimes M, et al. Methyltransferases prefer monomer over core-trimmed nucleosomes as in vitro substrates. Anal Biochem; 415:84-6.
36. Varambally, S. et al. The polycomb group protein EZH2 is involved in progression of prostate cancer. Nature 419, 624-629 (2002).
37. Kleer, C. G. et al. EZH2 is a marker of aggressive breast cancer and promotes neoplastic transformation of breast epithelial cells. Proc. Natl. Acad. Sci. U.S.A 100, 11606-11611 (2003).37
38. Wagener, N. et al. Enhancer of zeste homolog 2 (EZH2) expression is an independent prognostic factor in renal cell carcinoma. BMC. Cancer 10, 524 (2010).
39. Takawa, M. et al. Validation of the histone methyltransferase EZH2 as a therapeutic target for various types of human cancer and as a prognostic marker. Cancer Sci. 102, 1298-1305 (2011).
40. Pasqualucci, L. et al. Analysis of the coding genome of diffuse large B-cell lymphoma. Nat. Genet. 43, 830-837 (2011).
41. McCabe, M. T. et al. Mutation of A677 in histone methyltransferase EZH2 in human B-cell lymphoma promotes hypertrimethylation of histone H3 on lysine 27 (H3K27). Proc. Natl. Acad. Sci. U.S.A 109, 2989-2994 (2012).
42. Ryan, R. J. et al. EZH2 codon 641 mutations are common in BCL2-rearranged germinal center B cell lymphomas. PLoS. One. 6, e28585 (2011).
43. Wigle, T. J. et al. The Y641C mutation of EZH2 alters substrate specificity for histone H3 lysine 27 methylation states. FEBS Lett. 585, 3011-3014 (2011).
44. Diaz, E. et al. Development and Validation of Reagents and Assays for EZH2 Peptide and Nucleosome High throughput Screens. J. Biomol. Screen. (2012).
45. Schubert, H. L., Blumenthal, R. M., & Cheng, X. Many paths to methyltransfer: a chronicle of convergence. Trends Biochem. Sci. 28, 329-335 (2003).
46. Miranda, T. B. et al. DZNep is a global histone methylation inhibitor that reactivates developmental genes not silenced by DNA methylation. Mol. Cancer Ther. 8, 1579-1588 (2009).
47. Dyer, M. J., Fischer, P., Nacheva, E., Labastide, W., & Karpas, A. A new human B-cell non-Hodgkin's lymphoma cell line (Karpas 422) exhibiting both t (14; 18) and t(4; 11) chromosomal translocations. Blood 75, 709-714 (1990).
48. Al-Katib, A. M. et al. Bryostatin 1 down-regulates mdr1 and potentiates vincristine cytotoxicity in diffuse large cell lymphoma xenografts. Clin. Cancer Res. 4, 1305-1314 (1998).
49. Chou, R. H., Yu, Y. L., & Hung, M. C. The roles of EZH2 in cell lineage commitment. Am. J. Transl. Res. 3, 243-250 (2011).
50. Jankowska, A. M. et al. Mutational spectrum analysis of chronic myelomonocytic leukemia includes genes associated with epigenetic regulation: UTX, EZH2, and DNMT3A. Blood 118, 3932-3941 (2011).
51. Ernst, T. et al. Inactivating mutations of the histone methyltransferase gene EZH2 in myeloid disorders. Nat. Genet. 42, 722-726 (2010).
52. Makishima, H. et al. Novel homo- and hemizygous mutations in EZH2 in myeloid malignancies. Leukemia 24, 1799-1804 (2010).
53. Chapman, P. B. et al. Improved survival with vemurafenib in melanoma with BRAF V600E mutation. N. Engl. J. Med. 364, 2507-2516 (2011).
54. Kwak, E. L. et al. Anaplastic lymphoma kinase inhibition in non-small-cell lung cancer. N. Engl. J. Med. 363, 1693-1703 (2010).
55. Gui, Y. et al. Frequent mutations of chromatin remodeling genes in transitional cell carcinoma of the bladder. Nat. Genet. 43, 875-878 (2011).
56. Langmead, B., Trapnell, C., Pop, M., & Salzberg, S. L. Ultrafast and memory-efficient alignment of short DNA sequences to the human genome. Genome Biol. 10, R25 (2009).
57. Zang, C. et al. A clustering approach for identification of enriched domains from histone modification ChIP-Seq data. Bioinformatics. 25, 1952-1958 (2009).
58. Tornheim, K. Kinetic applications using high substrate and competitive inhibitor concentrations to determine Ki or Km. Anal. Biochem. 221, 53-56 (1994).
59. Cheng, Y. & Prusoff, W. H. Relationship between the inhibition constant (K1) and the concentration of inhibitor which causes 50 percent inhibition (I50) of an enzymatic reaction. Biochem. Pharmacol. 22, 3099-3108 (1973).

TABLE 1

Steady state kinetic parameters for wild type and mutant EZH2 enzymes.

| Enzyme | Substrate | SAM $K_m$ (µM) | Subtrate $K_m$ (µM) | $k_{cat}$ (min$^{-1}$) | SAM $k_{cat}/K_m$ (µM$^{-1}$ min$^{-1}$) | Substrate $k_{cat}/K_m$ (µM$^{-1}$min$^{-1}$) |
|---|---|---|---|---|---|---|
| wild type | H3K27me0 | 0.34 ± 0.09 | 4.23 ± 0.76 | 0.62 ± 0.04 | 1.82 ± 0.44 | 0.15 ± 0.05 |
|  | H3K27me1 | 0.51 ± 0.10 | 7.44 ± 1.19 | 0.41 ± 0.03 | 0.80 ± 0.34 | 0.06 ± 0.03 |
|  | H3K27me2 | 0.21 ± 0.06 | 2.42 ± 0.45 | 0.016 ± 0.001 | 0.08 ± 0.02 | 0.007 ± 0.002 |
|  | nucleosomes | 0.10 ± 0.02 | 0.08 ± 0.01 | 0.10 ± 0.01 | 0.99 ± 0.33 | 1.22 ± 0.23 |
| A677G | H3K27me0 | 0.34 ± 0.23 | 4.52 ± 0.99 | 0.64 ± 0.06 | 1.89 ± 0.25 | 0.14 ± 0.06 |
|  | H3K27me1 | 0.89 ± 0.16 | 10.95 ± 1.45 | 0.69 ± 0.05 | 0.78 ± 0.29 | 0.06 ± 0.03 |
|  | H3K27me2 | 0.95 ± 0.16 | 5.18 ± 0.84 | 0.56 ± 0.04 | 0.59 ± 0.24 | 0.11 ± 0.05 |
|  | nucleosomes | 0.20 ± 0.04 | 0.06 ± 0.01 | 0.17 ± 0.02 | 0.85 ± 0.50 | 3.04 ± 0.95 |
| Y641N | H3K27me0 | *— | — | — | — | — |
|  | H3K27me1 | 0.64 ± 0.31 | 22.71 ± 6.12 | 0.42 ± 0.07 | 0.66 ± 0.23 | 0.02 ± 0.01 |
|  | H3K27me2 | 0.76 ± 0.09 | 2.72 ± 0.27 | 1.00 ± 0.04 | 1.31 ± 0.48 | 0.37 ± 0.16 |
|  | nucleosomes | 0.06 ± 0.01 | 0.05 ± 0.01 | 0.073 ± 004 | 1.28 ± 0.29 | 1.49 ± 0.35 |
| Y641F | H3K27me0 | 1.19 ± 0.39 | 8.14 ± 2.35 | 0.08 ± 0.01 | 0.07 ± 0.03 | 0.010 ± 0.004 |
|  | H3K27me1 | 0.65 ± 0.19 | 15.10 ± 2.62 | 0.15 ± 0.01 | 0.23 ± 0.07 | 0.010 ± 0.005 |

TABLE 1-continued

Steady state kinetic parameters for wild type and mutant EZH2 enzymes.

| Enzyme | Substrate | SAM $K_m$ (μM) | Subtrate $K_m$ (μM) | $k_{cat}$ (min$^{-1}$) | SAM $k_{cat}/K_m$ (μM$^{-1}$ min$^{-1}$) | Substrate $k_{cat}/K_m$ (μM$^{-1}$ min$^{-1}$) |
|---|---|---|---|---|---|---|
| | H3K27me2 | 0.27 ± 0.06 | 3.93 ± 0.73 | 0.50 ± 0.04 | 1.86 ± 0.63 | 0.13 ± 0.05 |
| | nucleosomes | 0.08 ± 0.02 | 0.05 ± 0.01 | 0.07 ± 0.01 | 0.88 ± 0.25 | 1.46 ± 0.38 |
| Y641S | H3K27me0 | — | — | — | — | — |
| | H3K27me1 | 0.49 ± 0.14 | 3.46 ± 0.74 | 0.21 ± 0.01 | 0.43 ± 0.09 | 0.06 ± 0.02 |
| | H3K27me2 | 0.49 ± 0.08 | 2.66 ± 0.39 | 0.62 ± 0.03 | 1.26 ± 0.41 | 0.23 ± 0.09 |
| | nucleosomes | 0.15 ± 0.03 | 0.07 ± 0.01 | 0.11 ± 0.01 | 0.73 ± 0.27 | 1.55 ± 0.42 |
| Y641H | H3K27me0 | — | — | — | — | — |
| | H3K27me1 | 2.14 ± 0.45 | 6.12 ± 1.44 | 0.14 ± 0.02 | 0.07 ± 0.04 | 0.02 ± 0.01 |
| | H3K27me2 | 0.59 ± 0.11 | 4.05 ± 0.65 | 0.16 ± 0.01 | 0.26 ± 0.10 | 0.04 ± 0.02 |
| | nucleosomes | 0.06 ± 0.01 | 0.04 ± 0.01 | 0.04 ± 0.002 | 0.67 ± 0.20 | 1.00 ± 0.17 |
| Y641C | H3K27me0 | — | — | — | — | — |
| | H3K27me1 | — | — | — | — | — |
| | H3K27me2 | 2.84 ± 0.62 | 11.99 ± 2.72 | 0.58 ± 0.07 | 0.20 ± 0.12 | 0.05 ± 0.03 |
| | nucleosomes | 0.17 ± 0.04 | 0.04 ± 0.01 | 0.03 ± 0.002 | 0.18 ± 0.05 | 0.68 ± 0.21 |

*could not obtain value due to low activity

TABLE 2

Clinical profile and mutations identified in primary lymphomas

| Sample ID | Tumor type | Gender | Age | Nucleotide Change* | AA Change* | Mutation type | Zygosity |
|---|---|---|---|---|---|---|---|
| CD563845 | DLBCL | Male | 54 | G553G/C | D185D/H | Non-synonymous SNP (rs2302427) | Het |
| CD564749 | DLBCL | Female | 66 | G553G/C | D185D/H | Non-synonymous SNP (rs2302427) | Het |
| CD565202 | DLBCL | Female | 65 | G553G/C | D185D/H | Non-synonymous SNP (rs2302427) | Het |
| CD564307 | MCL | Male | 52 | G553G/C | D185D/H | Non-synonymous SNP (rs2302427) | Het |
| CD564609 | WM | Female | 56 | G553G/C | D185D/H | Non-synonymous SNP (rs2302427) | Het |
| CD564308 | DLBCL | Female | 74 | G553G/C; C2045C/G | D185D/H; A677A/G | Non-synonymous SNP (rs2302427); Non-synonymous missense mutation | Het |
| CD564591 | DLBCL | Male | 34 | G553G/C; A1937A/G | D185D/H; Y641Y/C | Non-synonymous SNP (rs2302427); Non-synonymous missense mutation | Het; Het |
| CD563202 | DLBCL | Female | 57 | No Changes | No Changes | WT | — |
| CD563344 | DLBCL | Male | 74 | No Changes | No Changes | WT | — |
| CD563479 | DLBCL | Male | 59 | No Changes | No Changes | WT | — |
| CD563546 | DLBCL | Female | 75 | No Changes | No Changes | WT | — |
| CD563726 | DLBCL | Male | 44 | No Changes | No Changes | WT | — |
| CD563892 | DLBCL | Male | 69 | No Changes | No Changes | WT | — |
| CD564332 | DLBCL | Male | 62 | No Changes | No Changes | WT | — |
| CD564370 | DLBCL | Male | 47 | No Changes | No Changes | WT | — |
| CD564431 | DLBCL | Male | 55 | No Changes | No Changes | WT | — |
| CD564439 | DLBCL | Male | 58 | No Changes | No Changes | WT | — |
| CD564624 | DLBCL | Male | 63 | No Changes | No Changes | WT | — |
| CD564669 | DLBCL | Male | 58 | No Changes | No Changes | WT | — |
| CD564960 | DLBCL | Male | 70 | No changes | No changes | WT | — |
| CD565057 | DLBCL | Male | 65 | No changes | No changes | WT | — |
| CD565083 | DLBCL | Male | 58 | No changes | No changes | WT | — |
| CD565170 | DLBCL | Male | 75 | No changes | No changes | WT | — |
| CD565185 | DLBCL | Male | 56 | No changes | No changes | WT | — |
| CD565213 | DLBCL | Male | 69 | No changes | No changes | WT | — |
| CD565293 | DLBCL | Male | 66 | No changes | No changes | WT | — |
| CD565343 | DLBCL | Male | 61 | No changes | No changes | WT | — |
| CD565361 | DLBCL | Female | 61 | No changes | No changes | WT | — |
| CD563565 | FL | Male | 78 | No changes | No changes | WT | — |
| CD564662 | FL | Female | 58 | No changes | No changes | WT | — |
| CD564711 | FL | Female | 57 | No changes | No changes | WT | — |
| CD565280 | FL | Male | 51 | No changes | No changes | WT | — |
| CD563109 | MALT | Male | 53 | No changes | No changes | WT | — |
| CD563451 | SMZL | Male | 55 | No changes | No changes | WT | — |
| CD564312 | WM | Male | 63 | No changes | No changes | WT | — |
| CD563285 | DLBCL | Male | 49 | C1477C/T; G1731G/A | P488P/S; P572P | Non-synonymous missense mutation; Synonymous SNP (rs41277437) | Het; Hom |
| CD563860 | DLBCL | Female | 76 | G1731G/A | P572P | Synonymous SNP (rs41277437) | Hom |
| CD564738 | DLBCL | Male | 72 | G1731G/A | P572P | Synonymous SNP (rs41277437) | Hom |
| CD564672 | FL | Male | 58 | A1937A/T | Y641Y/F | Non-synonymous missense mutation | Het |

TABLE 2-continued

Clinical profile and mutations identified in primary lymphomas

| Sample ID | Tumor type | Gender | Age | Nucleotide Change* | AA Change* | Mutation type | Zygosity |
|---|---|---|---|---|---|---|---|
| CD564341 | FL | Male | 57 | T1936T/C | Y641Y/H | Non-synonymous missense mutation | Het |
| CD564333 | DLBCL | Male | 65 | T1936T/A | Y641Y/N | Non-synonymous missense mutation | Het |

Diffuse Large B-cell Lymphoma (DLBCL);
Splenic marginal zone lymphoma (SMZL);
Waldenström's macroglobulinemia or lymphoplasmacytic lymphoma (WM);
Follicular lymphoma (FL);
Mantle Cell Lymphoma (MCL);
Extra nodal marginal zone B-cell lymphoma of mucosa assoicated lymphoid tissue (MALT)
Wild-type (WT);
single nucleotide polymorphism (SNP);
Homozygous (Hom);
Heterozygous (Het)
*Nucleotide/amino acid residue numbering based on NM_001203247

TABLE 3

Primers utilized for sequencing of EZH2 gDNA and cDNA.

| Reference | Template type | Location | Primer sequence 5' → 3'; F: forward; R: reverse) |
|---|---|---|---|
| chr7: 148504464-148581441 (hg19 build) | gDNA | Exon 2 | F: GGTGATCATATTCAGGCTGG<br>R: AAACTTATTGAACTTAGGAGGGG |
| | | Exon 3 | F: TTTTGTATTATTTGAATGTGGGAAA<br>R: AAGATGGACACCCTGAGGTC |
| | | Exon 4 | F: ACCCTAAGTAAAAGAAAAGAGAGAA<br>R: GGAAAAGAGTAATACTGCACAGG |
| | | Exon 5 | F: AAATCTGGAGAACTGGGTAAAGAC<br>R: TCATGCCCTATATGCTTCATAAAC |
| | | Exon 6 | F: FAGGCTATGCCTGTTTTGTCC<br>R: AAAAGAGAAAGAAGAAACTAAGCCC |
| | | Exon 7 | F: CTGACTGGCATTCCACAGAC<br>R: AAGTGTAGTGGCTCATCCGC |
| | | Exon 8 | F: CATCAAAAGTAACACATGGAAACC<br>R: TTGTAATAAATGATAGCACTCTCCA |
| | | Exon 9 | F: TCCATTAATTGACTTTTCCAGTG<br>R: ACCTCCACCAAAGTGCAAAG |
| | | Exon 10 | F: TTCTCTTCCATCAAAATGAGTTTTA<br>R: TCCTCACAACACGAACTTTCAC |
| | | Exon 11 | F: GAGTTGTCCTCATCTTTTCGC<br>R: CCAAGAATTTTCTTTGTTTGGAC |
| | | Exon 12 | F: AAGAATGGTTTGCCTAAATAAGAC<br>R: CCTTGCCTGCAGTGTCTATC |
| | | Exon 13 | F: TCTTGGCTTTAACGCATTCC<br>R: CAAATTGGTTTAACATACAGAAGGC |
| | | Exon 14 | F: TGATCGTTTCCATCTCCCTG<br>R: AGGGAGTGCTCCCATGTTC |
| | | Exon 15 | F: GAGAGTCAGTGAGATGCCCAG<br>R: TTTGCCCCAGCTAAATCATC |
| | | Exon 16 | F: TTTGTCCCCAGTCCATTTTC<br>R: TTTCCAATCAAACCCACAGAC |
| | | Exon 17 | F: TTCTGTCAGGCTTGATCACC<br>R: CTCGTTTCTGAACACTCGGC |
| | | Exon 18-19 | F: TGAAGCTGCTTGATTTATTTGC<br>R: AACCTAATTCCCCACTAATGCTC |

TABLE 3-continued

Primers utilized for sequencing of EZH2 gDNA and cDNA.

| Reference | Template type | Location | Primer sequence 5' → 3'; F: forward; R: reverse) |
|---|---|---|---|
| | | Exon 20 | F: TCTCAGCACATGTTGGATGG |
| | | | R: CCCACAGTACTCGAGGTTCC |
| NM_001203247 | cDNA | 176-193 | F: 5' GCGGGACGAAGAATAATC 3' |
| | | 538-555 | R: 5' ATAAAATTCTGCTGTAGG 3' |
| | | 495-516 | F: 5' TGAATGCAGTTGCTTCAGTACC 3' |
| | | 956-977 | R: 5' GGGTACATTCAGGAGGAAGTGC 3' |
| | | 886-905 | F: 5' TCCAGATAAGGGCACAGCAG 3' |
| | | 1397-1420 | R: 5' TTCAGAGGAGCTCGAAGTTTCATC 3' |
| | | 1259-1278 | F: 5' GGACGGCTTCCCAATAACAG 3' |
| | | 1788-1808 | R: 5' CTATCACACAAGGGCACGAAC 3' |
| | | 1693-1715 | F: 5' TGCACACTGCAGAAAGATACAGC 3' |
| | | 2223-2242 | R: 5' TTTGTTACCCTTGCGGGTTG 3' |
| | | 1950-1969 | F: 5' TTACTTGTGGAGCCGCTGAC 3' |
| | | 2455-2477 | R: 5' CTAAGGCAGCTGTTTCAGAGGAG 3' |

TABLE 4

Oligonucleotide sequences used for site-directed mutagenesis of EZH2.

EZH2 A677G sense      5- GAA CAATGA TTT TGT GGT GGATGG AAC CCG CAA GGGTAA CAA AAT TC -3
antisense  5- GAATTT TGT TAC CCT TGC GGGTTC CAT CCA CCA CAA AAT CAT TGT TC -3

EZH2 Y641N sense
antisense

EZH2 Y641F sense      5- GTG CAG AAA AAT GAA TTC ATC TCA GAA TTC TGT GGA GAG ATT ATT TCT CAA GAT G -3
antisense  5- CAT CTT GAG AAATAATCT CTC CAC AGA ATT CTG AGA TGA ATT CAT TTT TCT GCA C -3

EZH2 Y641S sense      5- GAA AAATGA ATT CAT CTC AGA ATC ATGTGG AGA GAT TAT TTC TC -3
antisense  5- GAG AAA TAA TCT CTC CAC ATG ATT CTG AGA TGA ATT CAT TTT TC -3

EZH2 Y641H sense      5- GAA AAA TGA ATT CAT CTC AGA ACA CTG TGG AGA GAT TAT TTC TC -3
antisense  5- GAG AAA TAA TCT CTC CAC AGT GTT CTG AGA TGA ATT CAT TTT TC -3

EZH2 Y641C sense      5- GCA GAA AAA TGA ATT CAT CTC AGA ATG CTG TGG AGA GAT TAT TTC TCA AGA TG -3
antisense  5- CAT CTT GAG AAA TAA TCT CTC CAC AGC ATT CTG AGA TGA ATT CAT TTT TCT GC -3

What is claimed is:

1. A method of treating cancer in a human in need thereof, comprising determining the presence of a mutation at the alanine 677 (A677) residue in Enhancer of Zeste Homolog 2 (EZH2) in a sample from said human; and administering to said human having a sample determined to have a presence of a mutation in A677 in EZH2 an effective amount of an EZH2 inhibitor or a pharmaceutically acceptable salt thereof, wherein the EZH2 inhibitor is a compound of Formula (I):

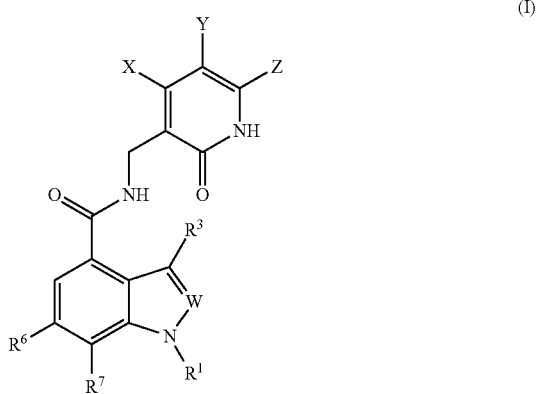

wherein:

W is N or $CR^2$;

X and Z are each independently selected from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, halogen, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is hydrogen or halogen;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C_{10})$bicycloalkyl, unsubstituted or substituted heterocycloalkyl or —$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, or —$CONR^aNR^aR^b$;

When present $R^2$ is hydrogen, $(C_1-C_8)$alkyl, trifluoromethyl, alkoxy, or halogen, in which said $(C_1-C_8)$alkyl may be substituted with one to two groups selected from amino and $(C_1-C_3)$alkylamino;

$R^7$ is hydrogen, $(C_1-C_3)$alkyl, or alkoxy; $R^3$ is hydrogen, $(C_1-C_8)$alkyl, cyano, trifluoromethyl, —$NR^aR^b$, or halogen;

$R^6$ is selected from the group consisting of hydrogen, halo, $(C_1-C_8)$alkyl, $(C_2-C_8)$alkenyl, —$B(OH)_2$, substituted or unsubstituted $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, $(C_1-C_8)$alkyl-heterocycloalkyl, $(C_3-C_8)$cycloalkyl-heterocycloalkyl, halogen, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halogen, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

each $R^c$ is independently $(C_1-C_4)$alkylamino, —$NR^aSO_2R^b$, —$SOR^a$, —$SO_2R^a$, —$NR^aC(O)OR^a$, —$NR^aR^b$, or —$CO_2R^a$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from halogen, hydroxyl, $(C_1-C_4)$alkoxy, amino, $(C_1-C_4)$alkylamino, $((C_1-C_4)$alkyl)$((C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)$((C_1-C_4)$alkyl), —$SO_2(C_1-C_4)$alkyl, —$SO_2NH_2$, —$SO_2NH(C_1-C_4)$alkyl, or —$SO_2N((C_1-C_4)$alkyl)$((C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a pharmaceutically acceptable salt thereof.

2. The method of claim 1, wherein the EZH2 inhibitor is a compound of Formula (I) wherein W is $CR^2$.

3. The method of claim 1, wherein the EZH2 inhibitor is Compound B:

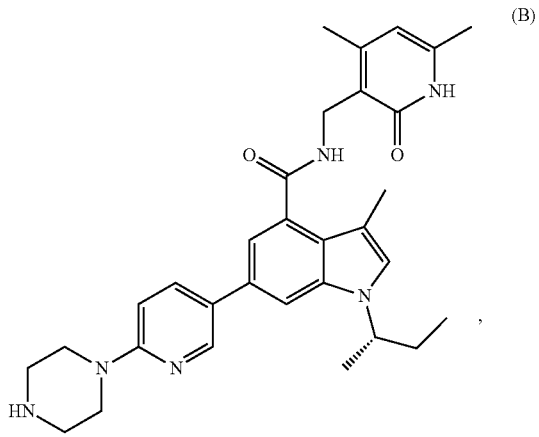 [SMILES: CC[C@H](C)n1cc(C)c2c(C(=O)NCc3c(C)cc(C)[nH]c3=O)cc(-c3ccc(N4CCNCC4)nc3)cc21]

or a pharmaceutically acceptable salt thereof.

4. The method of claim 1, wherein the A677 mutation is A677G.

5. The method of claim 1, wherein the sample comprises at least one cancer cell.

6. The method of claim 1, wherein the cancer is lymphoma.

7. The method of claim 6, wherein the lymphoma is selected from the group consisting of: germinal center B-cell (GCB), Diffuse Large B-cell Lymphoma (DLBCL), Splenic marginal zone lymphoma (SMZL), Waldenström's macroglobulinemia lymphoplasmacytic lymphoma (WM), Follicular lymphoma (FL), Mantle Cell Lymphoma (MCL), and Extra nodal marginal zone B-cell lymphoma of mucosa associated lymphoid tissue (MALT).

8. The method of claim 1, wherein the A677 mutation is a somatic mutation.

9. The method of claim 1, wherein said human has an increased response rate and/or an improved progression free survival when treated with an EZH2 inhibitor compared to a human without an A766 mutation in EZH2.

10. The method of claim 1, further comprising administering one or more additional anti-neoplastic agents.

* * * * *

SEQUENCE LISTING

<160> NUMBER OF SEQ ID NOS: 58

<210> SEQ ID NO 1
<211> LENGTH: 20
<212> TYPE: DNA
<213> ORGANISM: Artificial Sequence
<220> FEATURE:
<223> OTHER INFORMATION: Primer -continued

```
<400> SEQUENCE: 1
ggtgatcata ttcaggctgg                                              20

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
aaacttattg aacttaggag ggg                                          23

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ttttgtatta tttgaatgtg ggaaa                                        25

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aagatggaca ccctgaggtc                                              20

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
accctaagta aagaaaaga gagaa                                         25

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ggaaaagagt aatactgcac agg                                          23

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
aaatctggag aactgggtaa agac                                         24

<210> SEQ ID NO 8
<211> LENGTH: 24
```

```
<212> TYPE: DNA
<213> ORGANISM: Artificial Sequence
<220> FEATURE:
<223> OTHER INFORMATION: Primer

<400> SEQUENCE: 8
tcatgcccta tatgcttcat aaac                                          24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
aggctatgcc tgttttgtcc                                               20

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
aaaagagaaa gaagaaacta agccc                                         25

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
ctgactggca ttccacaga                                                19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aagtgtagtg gctcatccgc                                               20

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
catcaaaagt aacacatgga aacc                                          24

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
```
ttgtaataaa tgatagcact ctcca                                                 25

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tccattaatt gactttcca gtg                                                    23

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
acctccacca aagtgcaaag                                                       20

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
ttctcttcca tcaaaatgag tttta                                                 25

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
tcctcacaac acgaactttc ac                                                    22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gagttgtcct catcttttcg c                                                     21

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ccaagaattt tctttgtttg gac                                                   23

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
aagaatggtt tgcctaaata agac                                          24

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ccttgcctgc agtgtctatc                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tcttggcttt aacgcattcc                                               20

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
caaattggtt taacatacag aaggc                                         25

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tgatcgtttc catctccctg                                               20

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
agggagtgct cccatgttc                                                19

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
gagagtcagt gagatgccca g                                             21

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tttgccccag ctaaatcatc                                            20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tttgtcccca gtccattttc                                            20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
tttccaatca aacccacaga c                                          21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ttctgtcagg cttgatcacc                                            20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ctcgtttctg aacactcggc                                            20

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
tgaagctgct tgatttattt gc                                         22

<210> SEQ ID NO 34
<211> LENGTH: 23
<212> TYPE: DNA
<213> ORGANISM: Artificial Sequence
<220> FEATURE:
<223> OTHER INFORMATION: Primer -continued

<400> SEQUENCE: 34
aacctaattc cccactaatg ctc                                            23

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tctcagcaca tgttggatgg                                                20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cccacagtac tcgaggttcc                                                20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
gcgggacgaa gaataatc                                                  18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
ataaaattct gctgtagg                                                  18

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
tgaatgcagt tgcttcagta cc                                             22

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
gggtacattc aggaggaagt gc                                             22

<210> SEQ ID NO 41

```
<211> LENGTH: 20
<212> TYPE: DNA
<213> ORGANISM: Artificial Sequence
<220> FEATURE:
<223> OTHER INFORMATION: Primer

<400> SEQUENCE: 41
tccagataag ggcacagcag                                                     20

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
ttcagaggag ctcgaagttt catc                                                24

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
ggacggcttc ccaataacag                                                     20

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
ctatcacaca agggcacgaa c                                                   21

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
tgcacactgc agaaagatac agc                                                 23

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
tttgttaccc ttgcgggttg                                                     20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
```

-continued ttacttgtgg agccgctgac                                                    20

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
ctaaggcagc tgtttcagag gag                                                23

<210> SEQ ID NO 49
<211> LENGTH: 47
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 49
gaacaatgat ttgtggtgg atggaacccg caagggtaac aaaattc                       47

<210> SEQ ID NO 50
<211> LENGTH: 47
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 50
gaattttgtt acccttgcgg gttccatcca ccacaaaatc attgttc                      47

<210> SEQ ID NO 51
<211> LENGTH: 55
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 51
gtgcagaaaa atgaattcat ctcagaattc tgtggagaga ttatttctca agatg            55

<210> SEQ ID NO 52
<211> LENGTH: 55
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 52
catcttgaga aataatctct ccacagaatt ctgagatgaa ttcattttc tgcac             55

<210> SEQ ID NO 53
<211> LENGTH: 44
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 53
gaaaaatgaa ttcatctcag aatcatgtgg agagattatt tctc                         44

<210> SEQ ID NO 54
<211> LENGTH: 44
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 54
gagaaataat ctctccacat gattctgaga tgaattcatt tttc          44

<210> SEQ ID NO 55
<211> LENGTH: 44
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 55
gaaaaatgaa ttcatctcag aacactgtgg agagattatt tctc          44

<210> SEQ ID NO 56
<211> LENGTH: 44
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 56
gagaaataat ctctccacag tgttctgaga tgaattcatt tttc          44

<210> SEQ ID NO 57
<211> LENGTH: 53
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 57
gcagaaaaat gaattcatct cagaatgctg tggagagatt atttctcaag atg          53

<210> SEQ ID NO 58
<211> LENGTH: 53
<212> TYPE: DNA
<213> ORGANISM: Artificial Sequence
<220> FEATURE:
<223> OTHER INFORMATION: Oligonucleotide sequences used for
      site-directed mutagenesis of EZH2

<400> SEQUENCE: 58
catcttgaga ataatctct ccacagcatt ctgagatgaa ttcattttc tgc          53